(12) United States Patent
Wells et al.

(10) Patent No.: US 10,857,211 B2
(45) Date of Patent: Dec. 8, 2020

(54) GENOMIC INSTABILITY MARKERS IN FANCONI ANEMIA

(71) Applicant: Children's Hospital Medical Center, Cincinnati, OH (US)

(72) Inventors: Susanne I. Wells, Cincinnati, OH (US); Kenneth D. R. Setchell, Cincinnati, OH (US); Lindsey Romick-Rosendale, Cincinnati, OH (US); Wujuan Zhang, Cincinnati, OH (US); Xueheng Zhao, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 394 days.

(21) Appl. No.: 15/358,620

(22) Filed: Nov. 22, 2016

(65) Prior Publication Data

US 2017/0100462 A1      Apr. 13, 2017

Related U.S. Application Data

(63) Continuation-in-part of application No. PCT/US2015/032204, filed on May 22, 2015.

(60) Provisional application No. 62/140,844, filed on Mar. 31, 2015, provisional application No. 62/001,686, filed on May 22, 2014.

(51) Int. Cl.
| | | |
|---|---|---|
| *A61K 38/46* | (2006.01) | |
| *A61K 47/26* | (2006.01) | |
| *C12N 15/113* | (2010.01) | |
| *A61K 31/445* | (2006.01) | |
| *A61K 31/451* | (2006.01) | |
| *C12Q 1/6886* | (2018.01) | |
| *G01N 33/574* | (2006.01) | |
| *G01N 33/92* | (2006.01) | |

(52) U.S. Cl.
CPC .......... *A61K 38/465* (2013.01); *A61K 31/445* (2013.01); *A61K 31/451* (2013.01); *A61K 47/26* (2013.01); *C12N 15/113* (2013.01); *C12Q 1/6886* (2013.01); *G01N 33/57426* (2013.01); *G01N 33/92* (2013.01); *C12N 2310/14* (2013.01); *G01N 2800/22* (2013.01)

(58) Field of Classification Search
CPC .............. C12N 15/113; C12N 2310/14; A61K 31/451; A61K 31/445; A61K 47/26; A61K 38/465; G01N 2800/22; G01N 33/92; G01N 33/57426; C12Q 1/6886
See application file for complete search history.

(56) References Cited

U.S. PATENT DOCUMENTS

| | | |
|---|---|---|
| 5,817,513 A | 10/1998 | Lopez et al. |
| 2009/0081237 A1 | 3/2009 | D'Andrea et al. |
| 2010/0210023 A1 | 8/2010 | Wong et al. |
| 2012/0157324 A1 | 6/2012 | Lizardi et al. |
| 2012/0270780 A1 | 10/2012 | Lee |
| 2013/0157875 A1 | 6/2013 | Shuber |
| 2014/0087397 A1 | 3/2014 | Romick-Rosendale |

OTHER PUBLICATIONS

PCT, International Preliminary Report on Patentability, International Application No. PCT/US2015/032204; dated Dec. 1, 2016, 8 pages.
Adamo et al.: Preventing Nonhomologous End Joining Suppresses DNA Repair Defects of Fanconi Anemia. Molecular Cell 2010, 39:25-35.
Alpi et al.: Mechanistic Insight Into Site-Restricted Monoubiquitination of FANCD2 by Ube2t, FANCL, and FANCI. Molecular Cell 2008, 32:767-77.
Alter et al.: Cancer in Fanconi Anemia. Blood 2003, 101:2072-2073.
Alter: Cancer in Fanconi Anemia, 1927-2001. American Cancer Society 2003, 97:425-440.
Alter: Fanconi's Anemia and Malignancies. American Journal of Hematology 1996, 53:99-110.
Ashe et al.: Iminosugar-Based Inhibitors of Glucosylceramide Synthase Increase Brain Glycosphingolipids and Survival in a Mouse Model of Sandhoff Disease. Plos ONE 2011, 6:e21758-e21758.
Bolot et al.: Analysis of Glycosphingolipids of Human Head and Neck Carcinomas with Comparison to Normal Tissue. Biochemistry and Molecular Biology International 1998, 46:125-35.
Bosch et al.: The Causal Relation Between Human Papillomavirus and Cervical Cancer. Journal of Clinical Pathology 2002, 55:244-65.
Broussard et al.: Desmosome Regulation and Signaling in Disease. Cell Tissue Research 2015, 360:501-512.
Caron et al.: Identification of Two Distinct Mechanisms of Phagocytosis Controlled by Different Rho GTPases. Science 1998, 282:1717-21.
Chan et al.: Autophosphorylation of the DNA-Dependent Protein Kinase Catalytic Subunit Is Required for Rejoining of DNA Double-Strand Breaks. Genes & Development 2002, 16:2333-8.
Chandra et al.: A Rapid Method for Retrovirus-Mediated Identification of Complementation Groups in Fanconi Anemia Patients. Molecular Therapy: The American Society of Gene Therapy 2005, 12:976-84.
Chen et al.: Cell Cycle Dependence of DNA-dependent Protein Kinase Phosphorylation in Response to DNA Double Strand Breaks. The Journal of Biological Chemistry 2005, 280:14709-15.
Chlon et al. Overcoming Pluripotent Stem Cell Dependence on the Repair of Endogenous DNA Damage. Stem Cell Reports, 2016, 6:44-54.
Corry et al.: Optimising the Therapeutic Ratio in Head and Neck Cancer. Lancet Oncol 2010, 11:287-91.
De Araujo et al: Fanconi's Anemia: Clinical and Radiographic Oral Manifestations. Oral Diseases 2007, 13:291-5.

(Continued)

*Primary Examiner* — Kortney L. Klinkel
*Assistant Examiner* — William Y Lee
(74) *Attorney, Agent, or Firm* — Thompson Hine LLP

(57) ABSTRACT

Markers for genomic instability in Fanconi Anemia (FA) and other pathologies for therapeutic and diagnostic uses. In one embodiment, glycosphingolipid metabolism is altered in the FA deficient squamous cell carcinoma (SCC) cells, based on analysis of a metabolomics/lipidomics platform. The data indicated ganglioside metabolism was important in FA patients' susceptibility to SCC progression.

12 Claims, 77 Drawing Sheets
(37 of 77 Drawing Sheet(s) Filed in Color)

(56) References Cited

OTHER PUBLICATIONS

De Kerviler et al: The Clinical and Radiological Features of Fanconi's Anaemia. Clinical Radiology 2000, 55:340-5.
Del Pozo et al.: Integrins Regulate Rac Targeting by Internalization of Membrane Domains. Science 2004, 303:839-42.
Douglas et al.: The DNA-Dependent Protein Kinase Catalytic Subunit is Phosphorylated In Vivo on Threonine 3950, a Highly Conserved Amino Acid in the Protein Kinase Domain. Molecular and Cellular Biology 2007, 27:1581-91.
Etienne-Manneville et al.: Rho GTPases in Cell Biology. Nature 2002, 420:629-35.
Evers et al.: Rho Family Proteins in Cell Adhesion and Cell Migration. European Journal of Cancer 2000, 36:1269-74.
Fakhry, et al.: Clinical Implications of Human Papillomavirus in Head and Neck Cancers. Journal of Clinical Oncology: Official Journal of the American Society of Clinical Oncology 2006, 24:2606-11.
Filho et al. Glycosphingolipid Expression in Squamous Cell Carcinoma of the Upper Aerodigestive Tract. Brazillian Journal of Otorhinolaryngology. 2006, 72:25-30.
Gammon et al.: Stem Cell Characteristics of Cell Sub-Populations in Cell Lines Derived From Head and Neck Cancers of Fanconi Anemia Patients. Journal of Oral Pathology & Medicine 2011, 40:143-52.
Gao et al.: Rational Design and Characterization of a Rac GTPase-Specific Small Molecule Inhibitor. Proceedings of the National Academy of Sciences of the United States of America 2004, 101:7618-23.
Giangreco et al.: Necl2 Regulates Epidermal Adhesion and Wound Repair. Development 2009, 136:3505-3514.
Gillison: Current Topics in the Epidemiology of Oral Cavity and Oropharyngeal Cancers. Head & Neck 2007, 29:779-792.
Goodpaster et al.: Statistical Significance Analysis of Nuclear Magnetic Resonance-Based Metabonomics Data. Analytical Biochemistry 2010, 401:134-43.
Gschwind et al. Lysophosphatidic Acid-Induced Squamous Cell Carcinoma Cell Proliferation and Motility Involves Epidermal Growth Factor Receptor Signal Transactivation. Cancer Research 2002, 62:6329-6323.
Guo et al.: Rac1 Controls Schwann Cell Myelination Through cAMP and NF2/merlin. The Journal of Neuroscience 2012, 32:17251-17261.
Hanenberg et al.: Phenotypic Correction of Primary Fanconi Anemia T Cells with Retroviral Vectors as a Diagnostic Tool. Exp Hematol 2002, 30:410-20.
Hattersley et al.: Lipid Composition of Membrane Rafts, Isolated With and Without Detergent, from the Spleen of a Mouse Model of Gaucher Disease. Biochemical and Biophysical Research Communications 2013, 442:62-7.
Hoskins et al.: Coordinate Regulation of Fanconi Anemia Gene Expression Occurs Through the Rb/E2F Pathway. Oncogene 2008, 27:4798-808.
Hoskins et al.: Fanconi Anemia Deficiency Stimulates HPV-Associated Hyperplastic Growth in Organotypic Epithelial Raft Culture. Oncogene 2009, 28:674-685.
Hoskins et al.: The Fanconi Anemia Pathway Limits Human Papillomavirus Replication. Journal of Virology 2012, 86:8131-8138.
Huang et al.: Human GM3 Synthase Attenuates Taxol-Triggered Apoptosis Associated with Downregulation of Caspase-3 in Ovarian Cancer Cells. Journal of Cancer Therapy 2012, 3:504-510.
Janich et al.: GM1 and GM3 Gangliosides Highlight Distinct Lipid Microdomains Within the Apical Domain of Epithelial Cells. FEBS Letters 2007, 581:1783-1787.
Karalis et al.: Dermatological Manifestations of Inherited Cancer Syndromes in Children. The British Journal of Dermatology 2011, 164:245-256.
Kee et al.: Molecular Pathogenesis and Clinical Management of Fanconi Anemia. The Journal of Clinical Investigation 2012, 122:3799-806.
Kennedy et al.: The Fanconi Anemia/BRCA Pathway: New Faces in the Crowd. Genes & Development 2005, 19:2925-40.
Kim et al.: Regulation of Multiple DNA Repair Pathways by the Fanconi Anemia Protein SLX4. Blood 2013, 121:54-63.
Kutler et al.: A 20-year Perspective on the International Fanconi Anemia Registry (IFAR). Blood 2003, 101:1249-56.
Kutler et al.: High Incidence of Head and Neck Squamous Cell Carcinoma in Patients With Fanconi Anemia. Archives of Otolaryngology Head & Neck Surgery 2003, 129:106-12.
Lacko et al.: Genetic Susceptibility to Head and Neck Squamous Cell Carcinoma. International Journal of Radiation Oncology, Biology, Physics 2014, 89:38-48.
Li et al.: Protein Phosphatase 2A and DNA-Dependent Protein Kinase are Involved in Mediating Rapamycin-Induced Akt Phosphorylation. The Journal of Biological Chemistry 2013, 288:13215-24.
Liu et al. Identification of Plasma Metabolomic Profiling for Diagnosis of Esophageal Squamous-Cell Carcinoma Using an UPLC/TOF/MS Platform. International Journal of Molecular Sciences 2013, 14:8899-8911.
Lombardi ,et al.: Acquisition of Relative Interstrand Crosslinker Resistance and PARP Inhibitor Sensitivity in Fanconi Anemia Head and Neck Cancers. Clinical Cancer Research: An Official Journal of the American Association for Cancer Research 2015, 21:1962-72.
Machida et al.: UBE2T is the E2 in the Fanconi Anemia Pathway and Undergoes Negative Autoregulation. Molecular Cell 2006, 23:589-596.
Meetei et al.: A Multiprotein Nuclear Complex Connects Fanconi Anemia and Bloom Syndrome. Molecular and Cellular Biology 2003, 23:3417-26.
Meetei et al.: A Novel Ubiquitin Ligase is Deficient in Fanconi Anemia. Nature Genetics 2003, 35:165-70.
Michaely et al.: Polarized Distribution of Endogenous Rac1 and RhoA at the Cell Surface. The Journal of Biological Chemistry 1999, 274:21430-6.
Miller et al.: Liposome-Mediated Delivery of Iminosugars Enhances Efficacy Against Dengue Virus In Vivo. Antimicrobial Agents and Chemotherapy 2012, 56:6379-86.
Milsom et al.: Fanca−/− Hematopoietic Stem Cells Demonstrate a Mobilization Defect Which can be Overcome by Administration of the Rac Inhibitor NSC23766. Haematologica 2009, 94:1011-15.
Moissoglu et al.: Regulation of Rac1 Translocation and Activation by Membrane Domains and Their Boundaries. Journal of Cell Science 2014, 127:2565-76.
Morrison et al.: Targeting the Human Papillomavirus E6 and E7 Oncogenes Through Expression of the Bovine Papillomavirus Type 1 E2 Protein Stimulates Cellular Motility. Journal of Virology 2011, 85:10487-98.
Nakahara et al.: Human Papillomavirus Type E1-E4 Contributes to Multiple Facets of the Papillomavirus Life Cycle. Journal of Virology 2005, 79:13150-65.
Nassar et al.: Structure-Function Based Design of Small Molecule Inhibitors Targeting Rho Family GTPases. Current Topics in Medicinal Chemistry 2006, 6:1109-16.
Nietupski et al.: Iminosugar-Based Inhibitors of Glucosylceramide Synthase Prolong Survival but Paradoxically Increase Brain Glucosylceramide Levels in Niemann-Pick C Mice. Molecular Genetics and Metabolism 2012, 105:621-8.
Nikolovski et al.: Barrier Function and Water-Holding and Transport Properties of Infant Stratum Corneum Are Different From Adult and Continue to Develop Through the First Year of Life. The Journal of Investigative Dermatology 2008, 128:1728-36.
Osmani et al.: Remodeling of Keratin-Coupled Cell Adhesion Complexes. Current Opinion in Cell Biology 2015, 32:30-8.
Pace et al.: Ku70 Corrupts DNA Repair in the Absence of the Fanconi Anemia Pathway. Science 2010, 329:219-23.
Park et al.: High Incidence of HPV-Associated Head and Neck Cancers in FA Deficient Mice is Associated With E7's Induction of DNA Damage Through its Inactivation of Pocket Proteins. PloS One 2013, 8:e75056.
Parkin et al.: Fifty Years of Cancer Incidence: CI5 I-IX. International Journal of Cancer Journal International 2010, 127:2918-27.

(56) References Cited

OTHER PUBLICATIONS

Piboonniyom et al.: Abrogation of the Retinoblastoma Tumor Suppressor Checkpoint During Keratinocyte Immortalization is not Sufficient for Induction of Centrosome-Mediated Genomic Instability. Cancer Research 2003, 63:476-83.

Platt et al.: Extensive Glycosphingolipid Depletion in the Liver and Lymphoid Organs of Mice Treated With N-Butyldeoxynojirimycin. The Journal of Biological Chemistry 1997, 272:19365-72.

Portoukalian et al.: Tumor Size-Dependent Elevations of Serum Gangliosides in Patients With Head and Neck Carcinomas. Biochemistry International 1989, 18:759-65.

Privette Vinnedge et al.: The Human DEK Oncogene Stimulates β-Catenin Signaling, Invasion and Mammosphere Formation in Breast Cancer. Oncogene 2011, 30:2741-52.

Resnik et al.: Desmosome Assembly and Cell-Cell Adhesion are Membrane Raft-Dependent Processes. The Journal of Biological Chemistry 2011, 286:1499-507.

Romick-Rosendale et al.: Identification of Urinary Metabolites That Distinguish Membranous Lupus Nephritis From Proliferative Lupus Nephritis and Focal Segmental Glomerulosclerosis. Arthritis Research & Therapy 2011, 13:R199, (10 pages).

Romick-Rosendale et al.: NMR-Based Metabonomics Analysis of Mouse Urine and Fecal Extracts Following Oral Treatment With the Broad-Spectrum Antibiotic Enrofloxacin (Baytril). Magnetic Resonance in Chemistry: MRC 2009, 47 Suppl 1:S36-46.

Romick-Rosendale et al.: The Fanconi Anemia Pathway: Repairing the Link Between DNA Damage and Squamous Cell Carcinoma. Mutation Research 2013, 743-744:78-88.

Rosenberg et al.: Cancer Incidence in Persons With Fanconi Anemia. Blood 2003, 101:822-6.

Rosenberg et al: Cancer Risks in Fanconi Anemia: Findings from the German Fanconi Anemia Registry. Haematologica 2008, 93:511-7.

Rossman et al.: GEF Means Go: Turning on RHO Gtpases With Guanine Nucleotide-Exchange Factors. Nature Reviews Molecular Cell Biology 2005, 6:167-80.

Schurr et al.: Clinical Evaluation of NIKS-Based Bioengineered Skin Substitute Tissue in Complex Skin Defects: Phase I/IIa Clinical Trial Results. Advances in Wound Care 2012, 1:95-103.

Singh et al.: BLAP18/RMI2, a Novel OB-Fold-Containing Protein, is an Essential Component of the Bloom Helicase-Double Holliday Junction Dissolvasome. Genes and Development 2008, 22:2856-68.

Smith et al.: Inactivation of the Tumor Suppressor Genes Causing the Hereditary Syndromes Predisposing to Head and Neck Cancer Via Promoter Hypermethylation in Sporadic Head and Neck Cancers. ORL; Journal for Otolaryngology-Heand and Neck Surgery 2010, 72:44-50.

Smogorzewska et al.: Identification of the FANCI Protein, a Monoubiquitinated FANCD2 Paralog Required for DNA Repair. Cell 2007, 129:289-301.

Stransky et al: The Mutational Landscape of Head and Neck Squamous Cell Carcinoma. Science 2011, 333:1157-60.

Taniguchi et al.: S-Phase-Specific Interaction of the Fanconi Anemia Protein, FANCD2, with BRCA1 and RAD51. Blood 2002, 100:2414-20.

Tischkowitz et al.: Fanconi Anaemia and Leukaemia—Clinical and Molecular Aspects. British Journal of Haematology 2004, 126:176-91.

Tu et al.: DNA-Dependent Protein Kinase Catalytic Subunit (DNA-PKcs)-SIN1 Association Mediates Ultraviolet B (UVB)-Induced Akt Ser-473 Phosphorylation and Skin Cell Survival. Molecular Cancer 2013, 12:172 (12 pgs).

Wang et al.: Ganglioside GM3 Depletion Reverses Impaired Wound Healing in Diabetic Mice by Activating IGF-1 and Insulin Receptors. The Journal of Investigative Dermatology 2014, 134:1446-55.

Wong et al.: A Role of DNA-PK for the Metabolic Gene Regulation in Response to Insulin. Cell 2009, 136:1056-72.

Wreesmann et al.: Downregulation of Fanconi Anemia Genes in Sporadic Head and Neck Squamous Cell Carcinoma. ORL; Journal for Oto-Rhino-Laryngology and its Related Specialties 2007, 69:218-25.

Wu, et al.: Cancer Stem Cells Are Enriched in Fanconi Anemia Head and Neck Squamous Cell Carcinomas. International Journal of Oncology 2014, 45:2365-72.

Yamashita et al.: Enhanced Insulin Sensitivity in Mice Lacking Ganglioside GM3. Proceedings of the National Academy of Sciences of the United States of America 2003, 100:3445-9.

Zhang et al.: Mechanism and Regulation of Incisions During DNA Interstrand Cross-Link Repair. DNA Repair 2014, 19:135-42.

Zhu et al.: An EGFR/PI3K/AKT Axis Promotes Accumulation of the Rac1-GEF Tiam1 that is Critical in EGFR-Driven Tumorigenesis. Oncogene 2015, pp. 1-12.

Metabolomics studies of normal FA keratinocytes

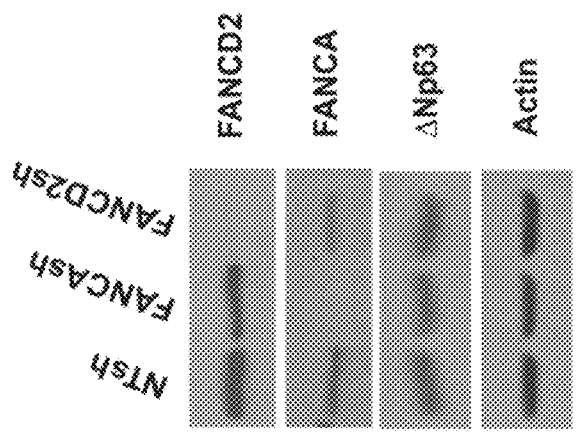
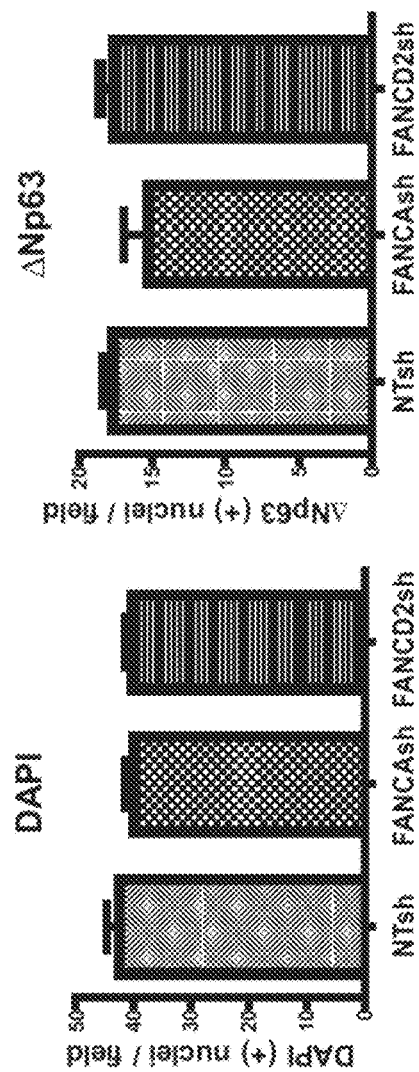
FIG. 2C
FIG. 2B
FA alters the MS metabolome

FA alters the MS metabolome b)

An increased level of lysophosphatidylcholines in FA plasma.

GENOMIC INSTABILITY MARKERS IN FANCONI ANEMIA

This application is a continuation-in-part of application No. PCT/US2015/032204 filed May 22, 2015, which claims priority to U.S. Ser. No. 62/140,844 filed Mar. 31, 2015 and 62/001,686 filed May 22, 2014, each of which is expressly incorporated by reference herein in its entirety.

This invention was made with government support under CA 102357 awarded by the National Institutes of Health. The government has certain rights in the invention.

Fanconi Anemia (FA) is a chromosome instability syndrome whose clinical manifestations typically present during childhood. FA patients are extremely susceptible to cancers including head and neck and other squamous cell carcinomas (SCC). Clinical management of this tumor type in FA remains dismal with two year survival below 50%. Molecular and chemical mechanisms underlying FA SCC pathogenesis are poorly understood, limiting effective treatment.

Other genetic instability disorders include ataxia telangiectasia (AT) and AT-like disorder (ATLD), Nijmegen breakage syndrome (NBS), Werner's syndrome, Bloom's syndrome, Rothmund-Thompson syndrome, xeroderma pigmentosa (XP), and Cockayne's syndrome (CS). Neurological disorders with a link to defective DNA repair include XP, CS, trichothiodystrophy, Down syndrome, AT, ATLD, NBS, Alzheimer's disease, Parkinson's disease, Huntington's disease, several spinocerebellar ataxias, Friedreich's ataxia, myotonic dystrophy types 1 and 2, spinocerebellar ataxia with axonal neuropathy-1, Triple-A syndrome, and amyotrophic lateral sclerosis (ALS).

Ganglioside metabolism is an important factor in FA susceptibility to SCC progression. Use of an unbiased metabolomics/lipodomics platform in FA knockdown systems revealed that glycosphingolipid metabolism was altered in the FA deficient SCC cells and in a non-tumorigenic human keratinocyte cell line, i.e. human near diploid immortalized keratinocytes that form skin (NIKS) and normal oral keratinocytes (NOKS). GM3 (NeuAC$\alpha$2-3Gal$\beta$1-4Glc$\beta$1-1ceramide), a monosialodihexosylganglioside, was identified as a class of differentially regulated metabolites that was significantly up-regulated in FA deficient SCC and NIKS cells along with other downstream gangliosides. Targeted analysis by ultra-performance liquid chromatography coupled with triple quadrupole mass spectrometry (UPLC-MS/MS) confirmed the identities and quantities of a wide range of gangliosides and their biosynthetic precursor, lactosylceramides, were elevated in FA deficient cells. Functional studies of these gangliosides revealed important activities in induction of advanced SCC tumor phenotypes.

The genomic markers are used in methods of diagnosing and treating FA. Gangliosides up-regulation in a patient indicates an increased evaluation and/or treatment for FA. In one embodiment, measuring gangliosides allows monitoring of FA progression in a patient. Gangliosides quantitations indicate dosing or type of treatments for patients with FA. A patient with FA may be treated with ganglioside inhibitor; the particular ganglioside may be a monosialodihexosylganglioside, GM3, or a metabolic precursor or metabolic product of GM3.

An untargeted metabolomics correlation network analysis revealed overall perturbed phospholipid pathways in FA cells. Patients with FA experience DNA repair defects with early bone marrow failure, leukemia and solid tumors. A metabolomics approach is disclosed to understand broader pathogenic mechanisms, and identify markers and therapeutic targets for this disease. High throughput analysis of immortalized keratinocytes with either FANCA or FANCD2 gene knockdown was conducted with ultra-high performance liquid chromatography (UPLC) coupled to quadruple time-of-flight (QTOF) mass spectrometry. To model and describe this highly multivariate dataset, network analyses were conducted to extract meaningful associations between metabolites. Weighted correlation network analysis (WGCNA) is an unsupervised approach to visualize patterns in genome level datasets. By measuring connection strength with topological overlap and hierarchical clustering of highly similar correlated features, metabolites are grouped into modules responsive to each clinical trait. The clustering of co-expressed metabolites extrapolates information from known to unknown nodes through "guilt by association". Using WGCNA, unsigned networks were constructed from metabolomics data that consisted of 61 metabolites. A module that was positively associated with loss function of FANCA and FANCD2 cells consisted of phosphatidylglycerol, phosphatidylinositol, and N-methyl-phosphatidylethanolamine. A module that was negatively associated with FA knockdown consisted of phosphatidylcholine, phosphatidylethanolamine, glycosylceramides, and phosphatidic acid. These modules suggest perturbed glycerophospholipid and sphingolipid metabolisms among the key mechanisms in FA deficiency metabolism. The results are consistent with urinary metabolomics study from FA patients, which also indicated a lipid signature associates with FA patient compared to unaffected siblings. Network analysis results are further examined with targeted methods monitoring the above pathways.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2B shows quantification of DAPI (left) and $\Delta$Np63 (right) in cells utilized for raft generation in FIG. 2A.

FIG. 2C shows a western blot confirming knockdown of FANCD2 and FANCA and equivalent expression of $\Delta$Np63 in the sporadic HNC cell line.

FIG. 3A shows normal immortalized human keratinocyte lines (NIKS) with non-targeting shRNA (NTsh) vs FANCA mutation;

FIG. 3B shows normal immortalized human keratinocyte lines (NIKS) with non-targeting shRNA (NTsh) vs FANCD2 mutation.

FIG. 22A shows Western-blot analysis of SCC1 cells knocked down with FANCA, FANCJ, FANCD2, or non-targeting/control (NT) lentiviral shRNA vectors. FIG. 22B shows SCC1 cells were knocked down for FANCD2 (vs untreated), treated with melphalan (or not), and then subjected to flow cytometry-based cell-cycle analysis. Percentages of cells in G2/M are indicated. FIG. 22C shows SCC1 cells were knocked down for FANCD2 (vs untreated) and BrdU incorporation assessed by. FIG. 22D shows SCC1 cells were knocked down for FANCD2 and examined under phase contrast. IF staining with the cholesterol probe filipin reveals sterol-rich membrane domains. Images were taken at the same magnification and exposure. FIG. 22E shows SCC1 cells were knocked down for FANCD2 or FANCJ, immunostained for phalloidin, and intercellular projections quantified in three independent experiments. Errors bars represent standard deviation;  $p<0.001$; * $p<0.0001$ (ANOVA). FIG. 22F shows FANCD2sh- and NTsh-treated SCC1 cells were cultured for 16 days as organotypic epithelial rafts, as described (15, 44) and then fixed, embedded, sectioned, and stained with hematoxylin and eosin (H&E).

FIG. 23A shows representative images of invasive SCC1 cells.

FIG. 24A shows Western blot analysis of NTsh-, FANCD2sh- and FANCJsh-treated SCC1 cells that were subjected to a 30-minute pulse of bleomycin to stimulate DNA damage signaling, and then treated with 10 uM NU7026 or DMSO.

FIG. 24B shows NTsh- and FANCD2sh-treated SCC1 cells that were plated in Matrigel-coated transwells with or without NU7026. After 22 hours, invasive cells were quantified. Representative images are shown. Experiments were carried out in duplicate, and standard deviation calculated.

FIG. 24C shows a Western blot of a Rac1-GTP pulldown assay performed on FANCJ-treated SCC1 cells.

FIG. 24D shows NTsh-, FANCD2sh- and FANCJsh-treated SCC1 cells that were treated with NSC23766 or DMSO, stained for phalloidin, and intercellular projections quantified as in FIG. 1E.

FIG. 23E shows a transwell invasion assay using cells treated with NSC23766 or DMSO over the course of the assay.

FIG. 23F shows FANCD2sh-treated SCC1 cells that were cultured for 48 hours in the presence of NSC23766 or DMSO.

FIG. 26A shows Keratinocytes, cultured from the skin of three FANCA patients, were immortalized with the HPV16 E6/E7 oncogenes, and then transduced to correct for the FANCA gene vs control.

FIG. 26B shows HNSCC cells cultured from the primary tumor of a FANCA patient, and then either control transduced of complemented with FANCA.

FIG. 26C shows FANCA-knockdown UM-SCC1 cells vs. control (FIG. 1A). Score plots are 2D representations of the principal component analysis (PCA), with each point representing a separate cellular NMR spectrum; multiple points of the same color represent experimental replicates. Solid oval lines indicate 90% confidence intervals for the two clusters of data points in each case.

FIG. 27A shows PCA analysis of 7480 features from SCC1 cells (n=6) and 7541 features from NIKS cells (n=5).

FIGS. F, G and H show Quantification of the targeted ganglioside detection. Two-tailed t test P values: *<0.05; <0.01; *<0.001; ****<0.0001.

Figure 27A:
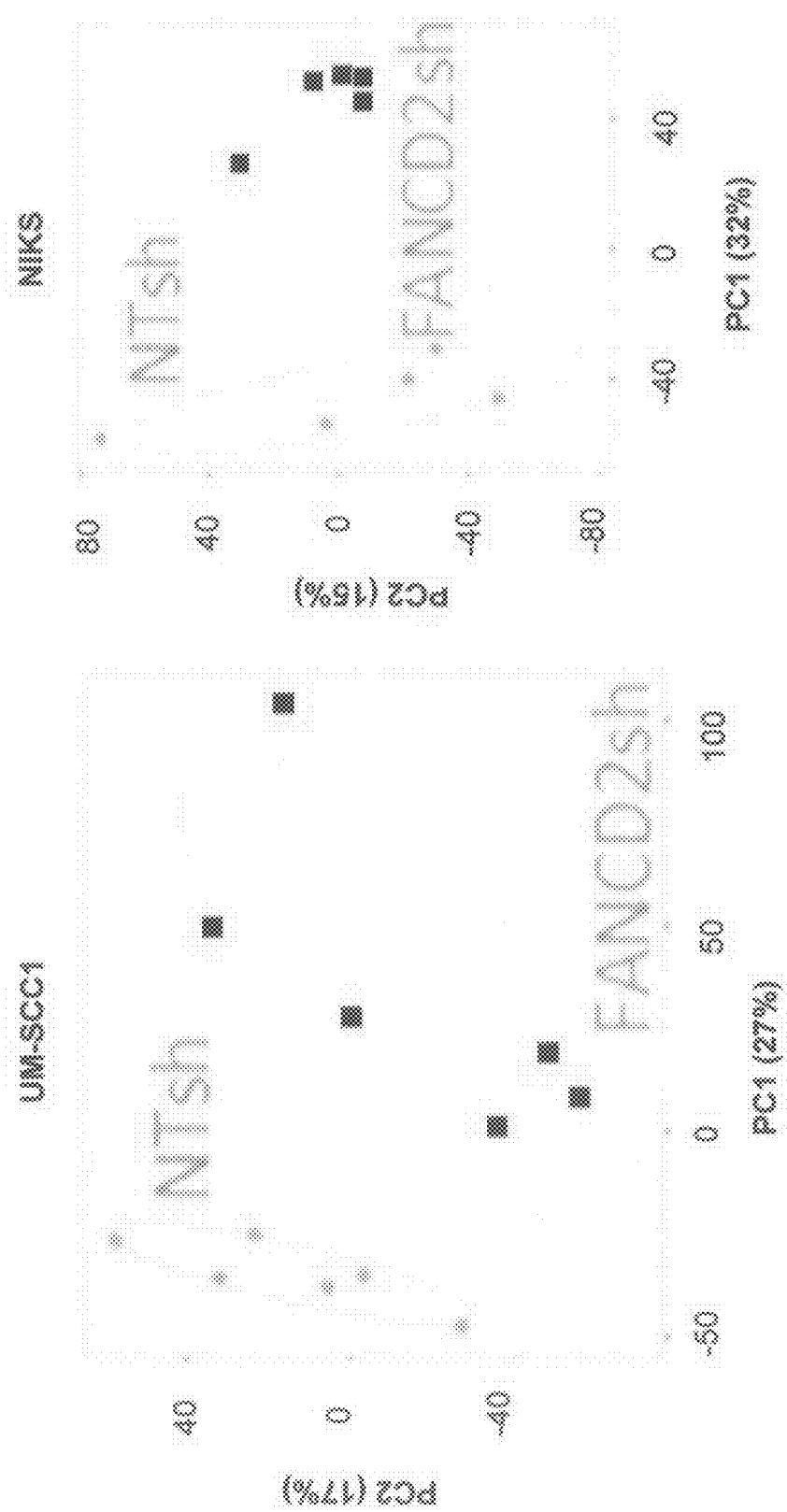
FIG. 27A to FIG. K show FANCD2 loss stimulates ganglioside biosynthesis. FANCD2sh versus NTsh UM-SCC1 Pellets from $10^6$ cells were extracted and normalized by cell number upon reconstitution for unbiased metabolomics analysis performed on a Xevo G2-S quadruple time-of-flight (Q-TOF) mass spectrometer interfaced with an ACQUITY ultra-high performance liquid chromatography (UPLC) system. An Acquity CSH C18 UPLC column was used for separation. Deconvolution, peak alignment, and preliminary normalization were conducted on raw metabolomics data with commercially available software (Progenesis QI). Each compound ion feature (i.e., a deconvoluted peak in the mass chromatogram) was annotated by elution time with m/z. Raw data were normalized by total compound ion intensity. Accurate molecular mass (based on m/z) was used for searches of the Human Metabolome Database (HMDB) and an in-house lipid database to identify candidate metabolite ions. Putative FA-specific metabolites were further confirmed by targeted UPLC-MS/MS methods using authentic standards. Univariate data analysis was applied in parallel on all compound ions from the unbiased metabolomics data. The parametric, two-sample t-test and non-parametric, Mann-Whitney-Wilcoxon test were applied to discover features significantly altered in FANCD2sh- versus NTsh-treated cells. Bonferroni and false discovery rate (FDR) corrections were used to control family-wise error in multiple hypothesis testing. All statistical analyses were conducted in the R environment for statistical computing.
Figure 27B:
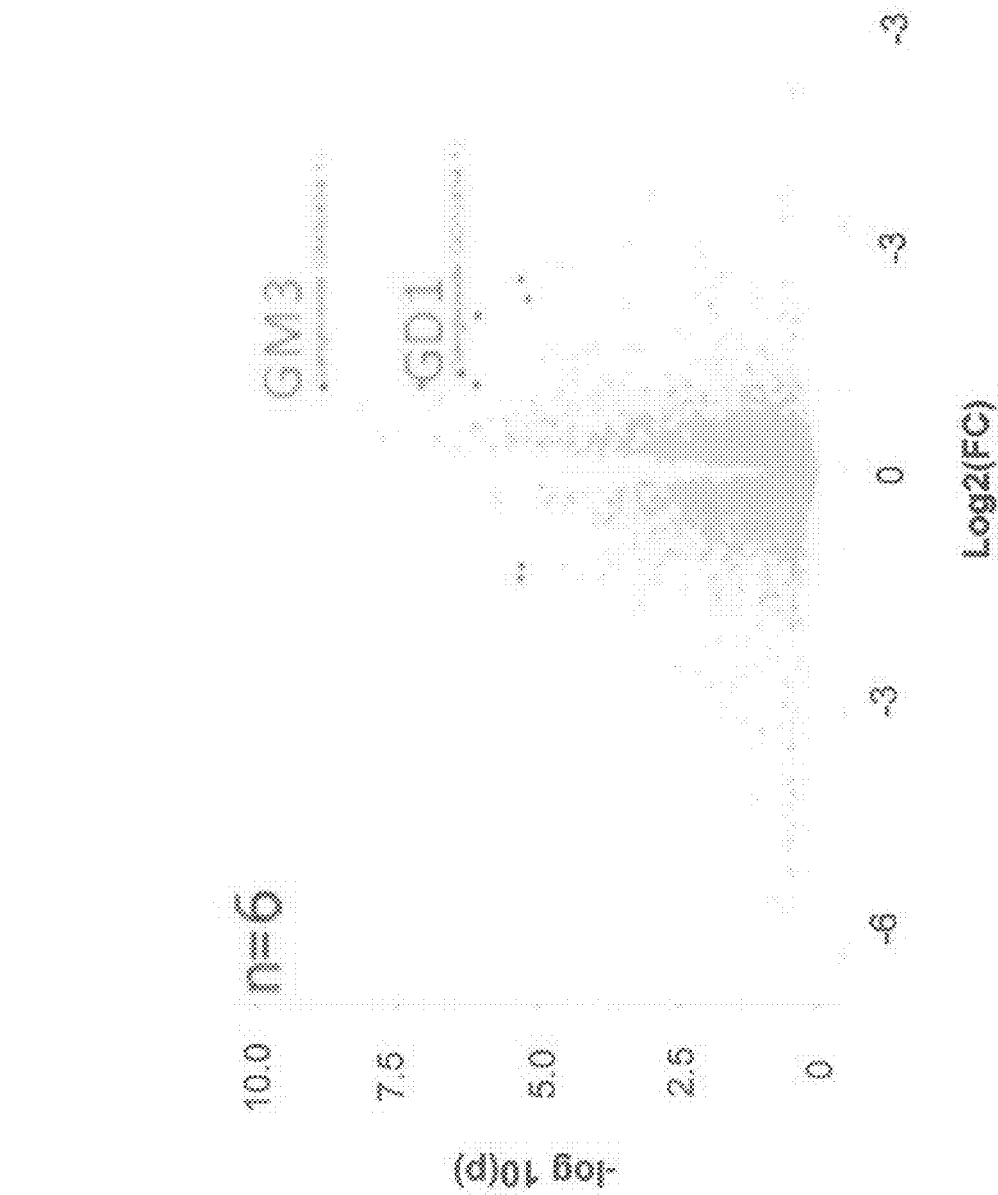
FIG. 27B shows Metabolites in a volcano plot; p-value calculated by parametric analysis with Bonferroni correction: Bonferroni adjusted p-value<0.05, fold change>2.
Figure 27C:
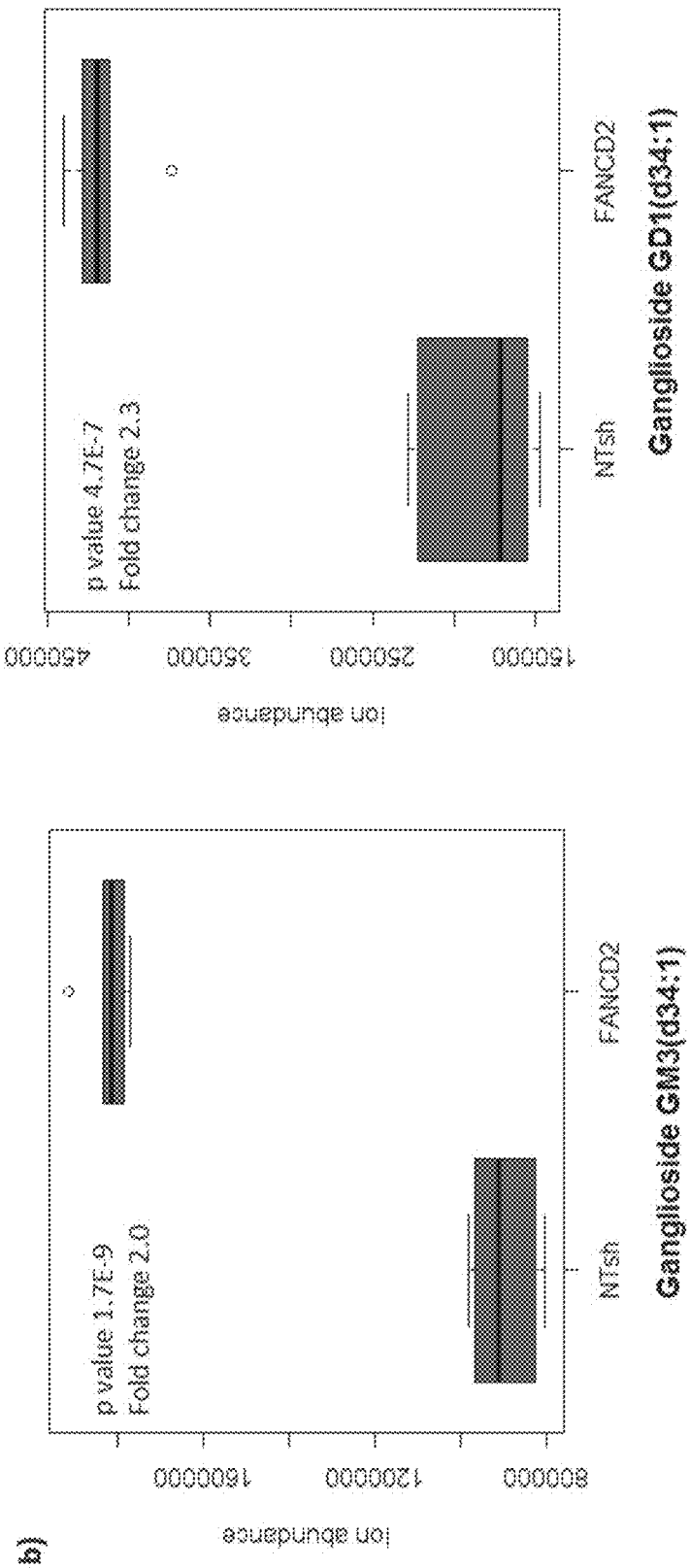
FIG. 27C shows a Box-and-whisker plot.
Figure 27D:
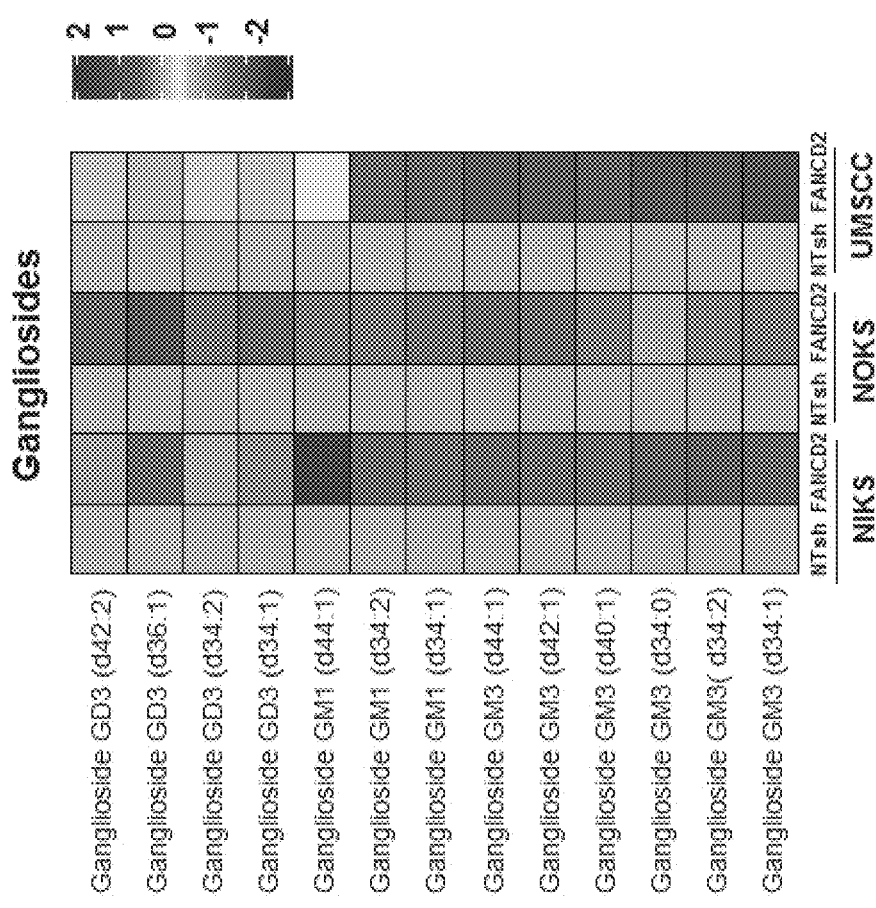
FIG. 27D shows a Heatmap of fold changes in metabolite concentrations within each group of gangliosides in the biosynthesis pathway with FANCD2sh- vs NTsh-treated NIKS and SCC1 cells. Grey darkness coding reflects fold changes of gangliosides in FANCD2sh normalized to NTsh cells (analytical replicates: n=6 in SCC1 cells, n=5 in NIKS cells), concentration (pmol/million cells) was treated with log 2 transformation.
Figure 27E:
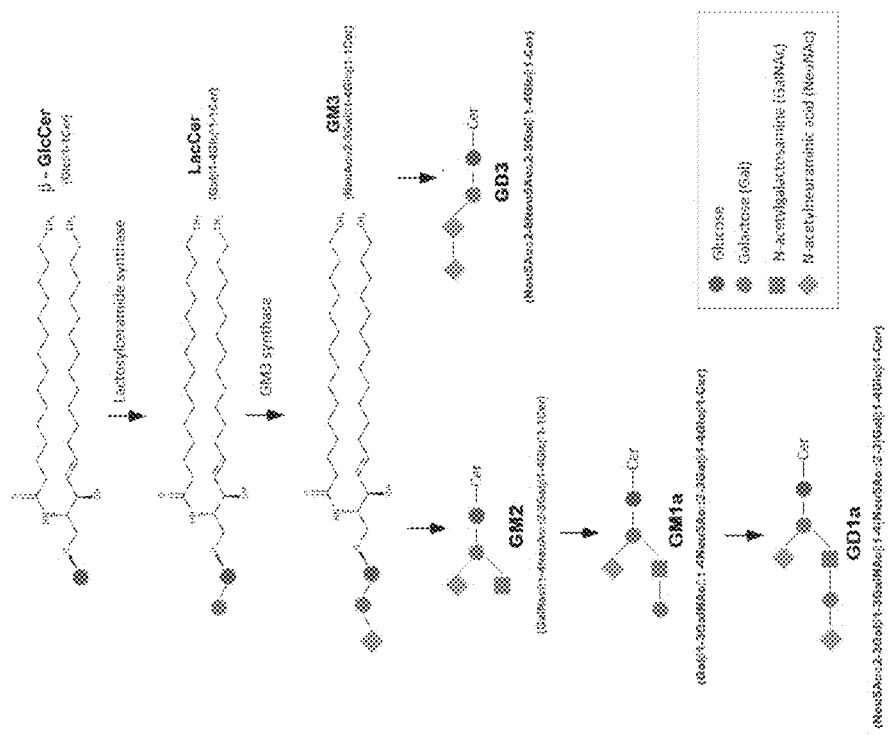
FIG. 27 E shows a Schematic of ganglioside biosynthesis.
Figure 27F:
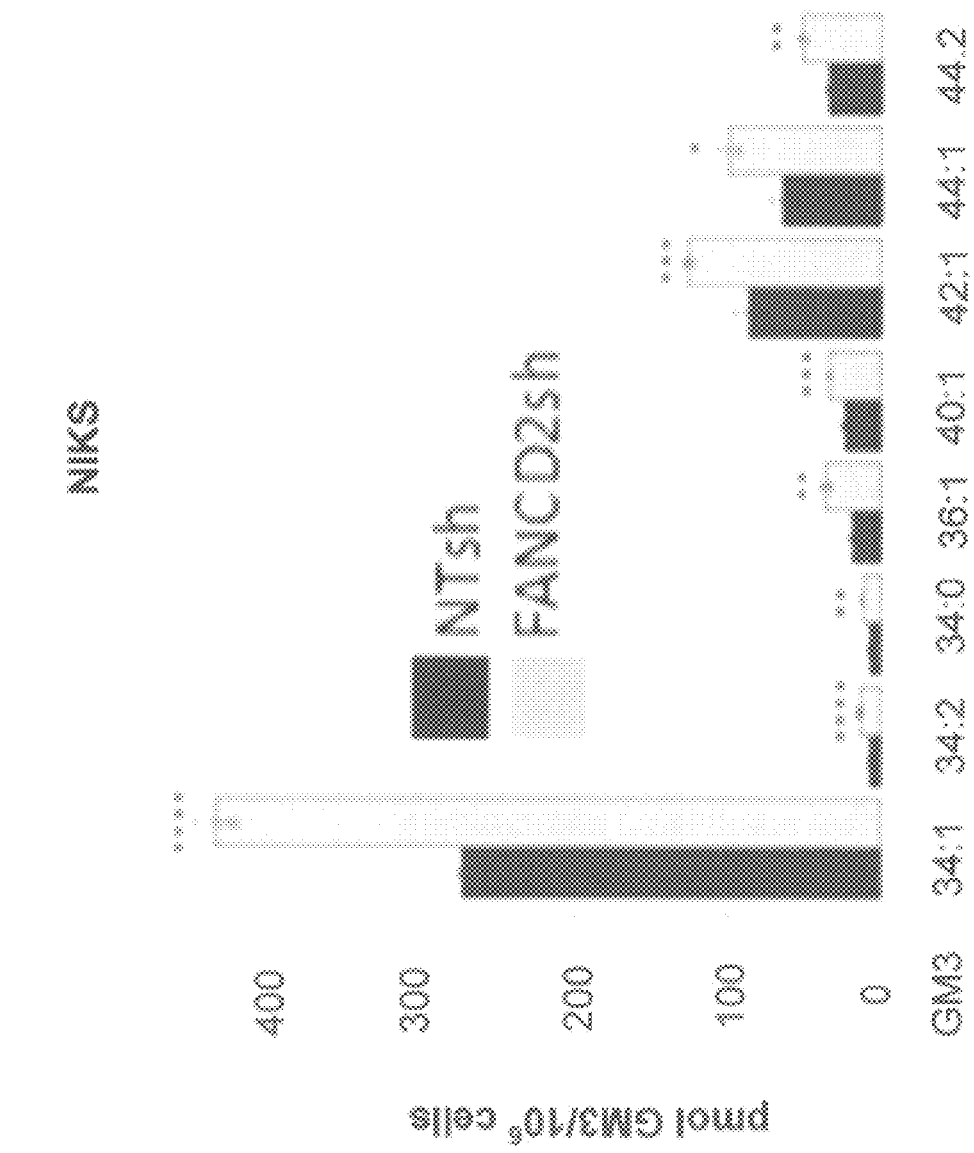
Figure 27G:
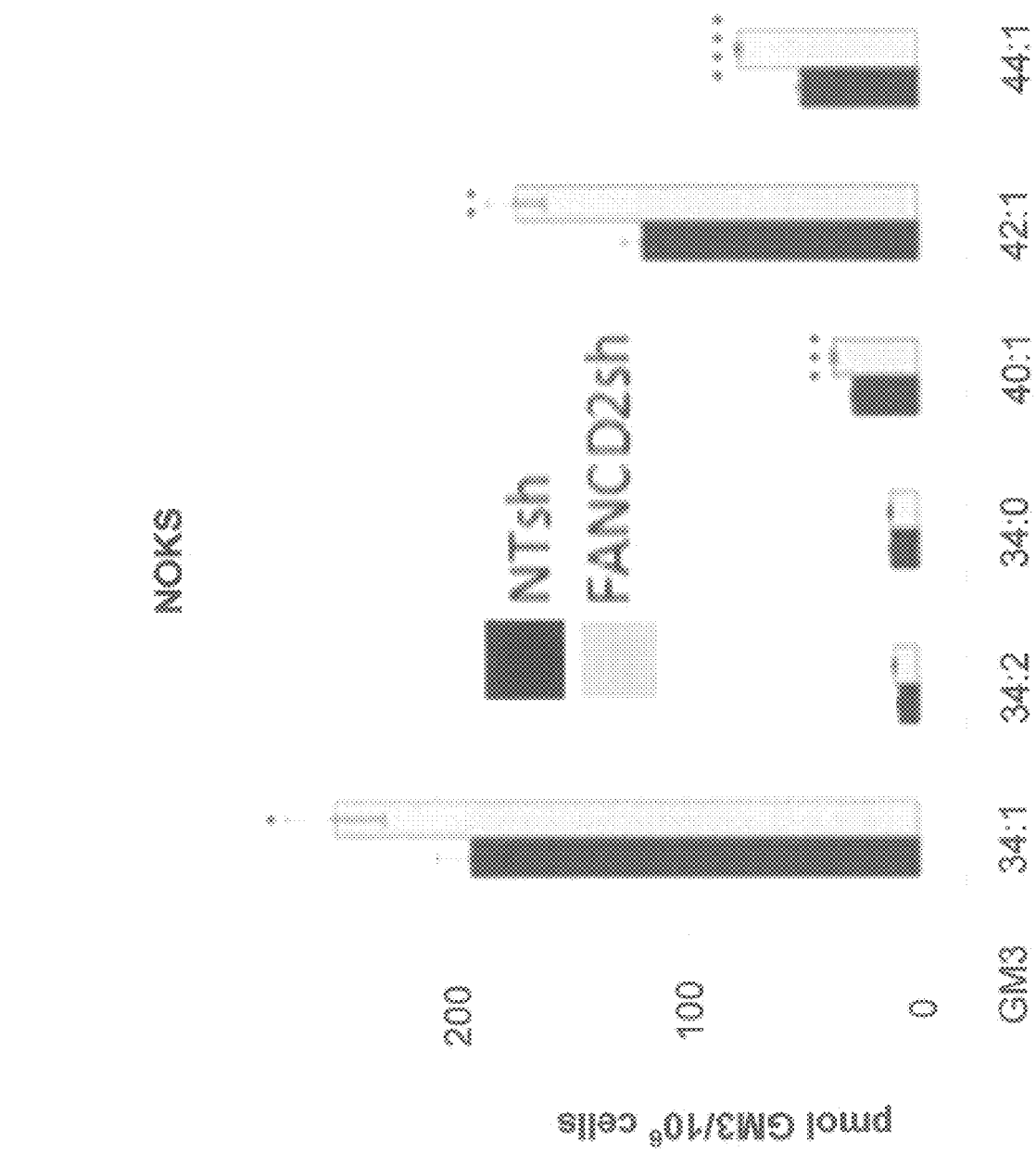
Figure 27H:
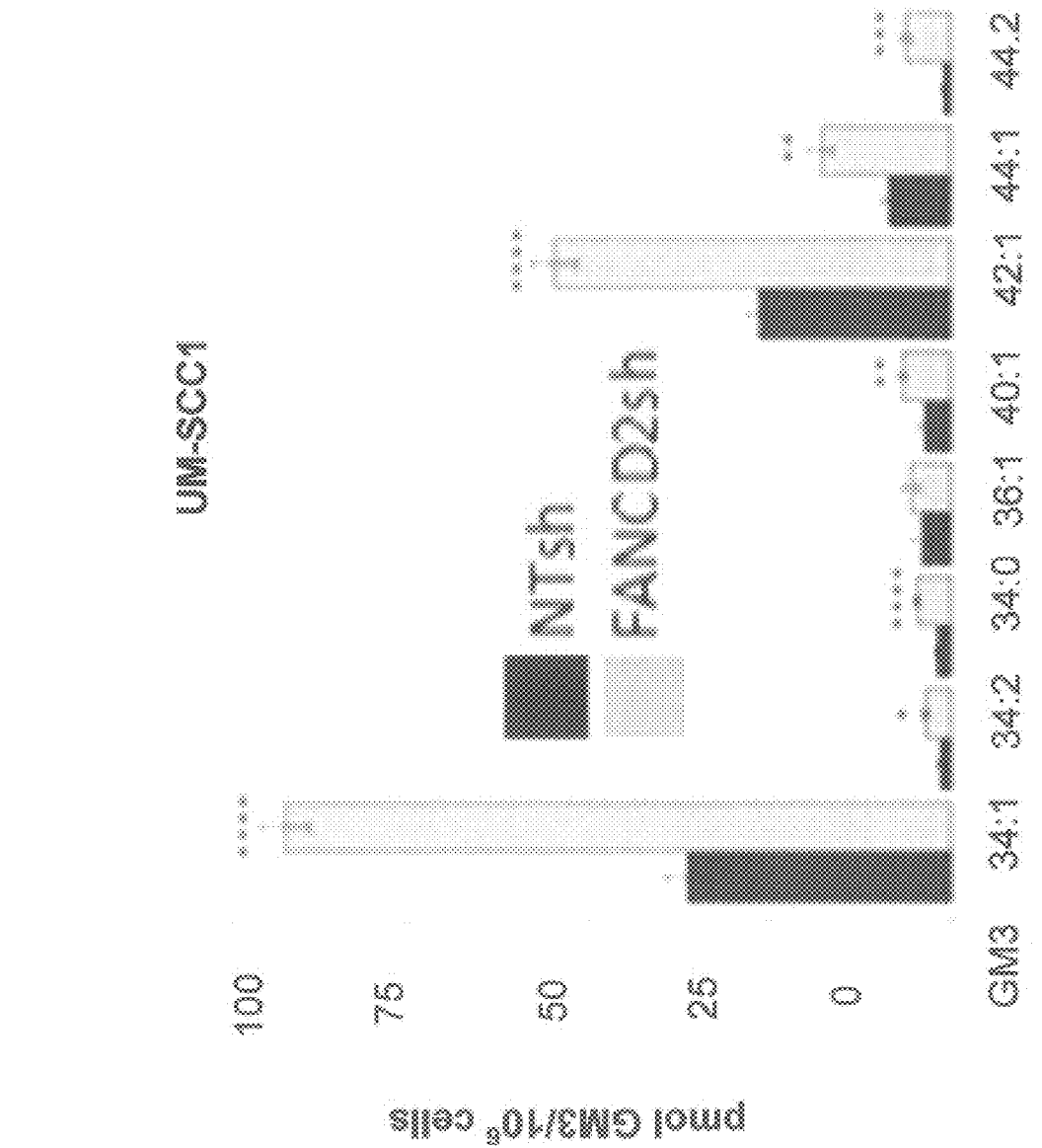
Figure 27I:
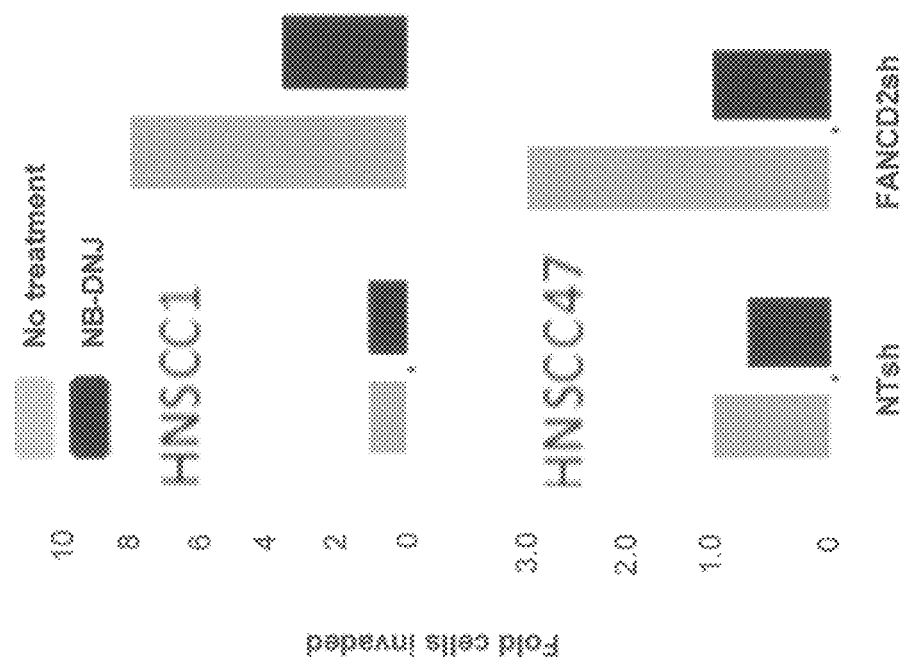
Figure 27J:
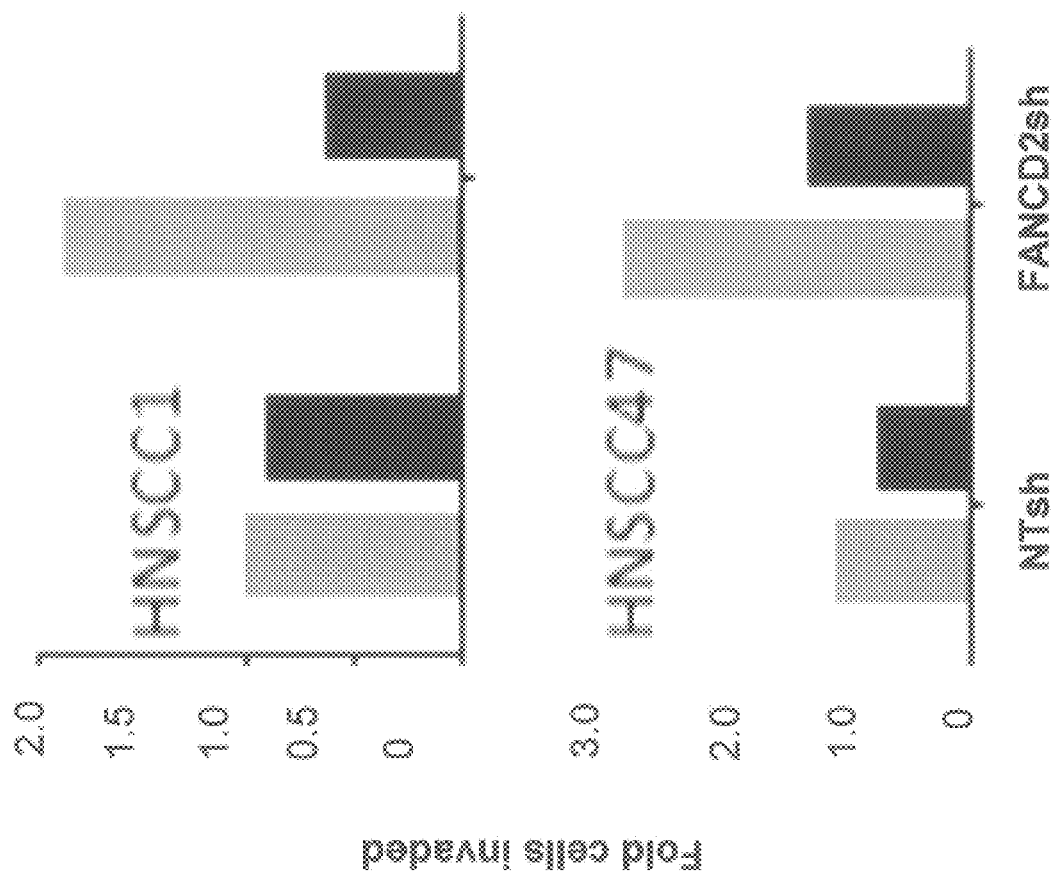

FIGS. 27I and J show NTsh-, FANCD2sh- and FANCJsh-treated SCC1 and SCC47 cells were cultured for 48 hrs in 100 uM NB-DNJ.

Figure 27K:
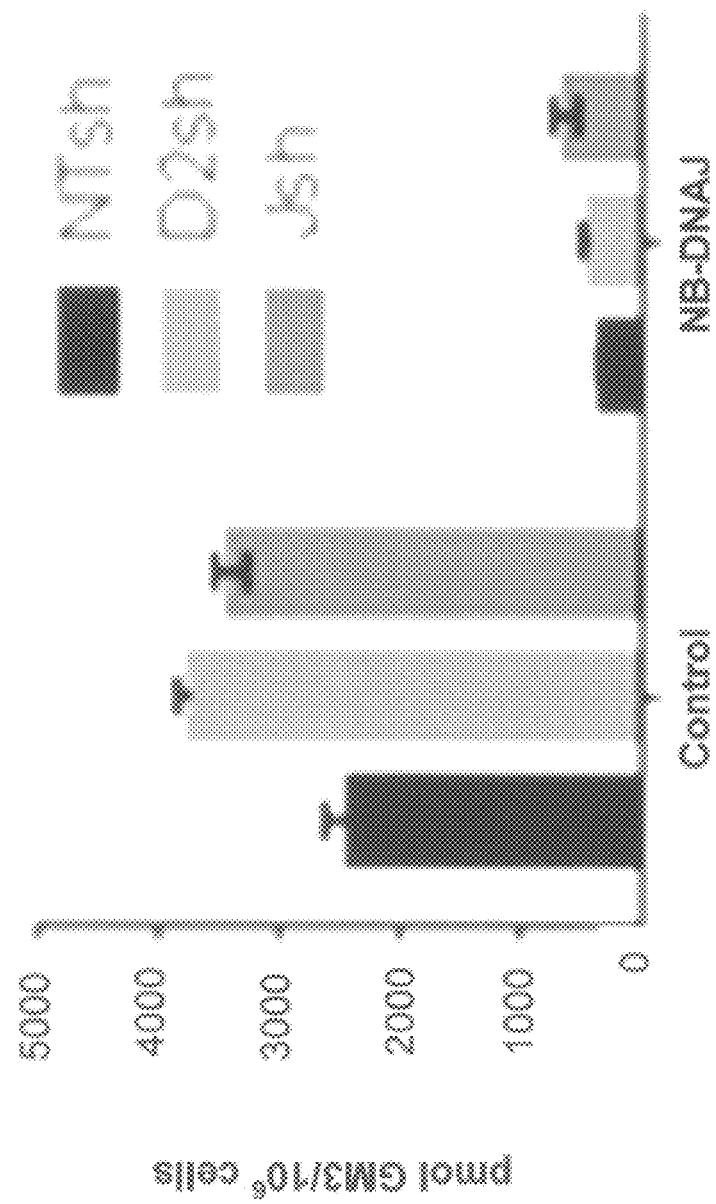

FIG. 27K shows GM3 repression in NB-DNAJ treated cells was verified by targeted MS.

Figure 28:
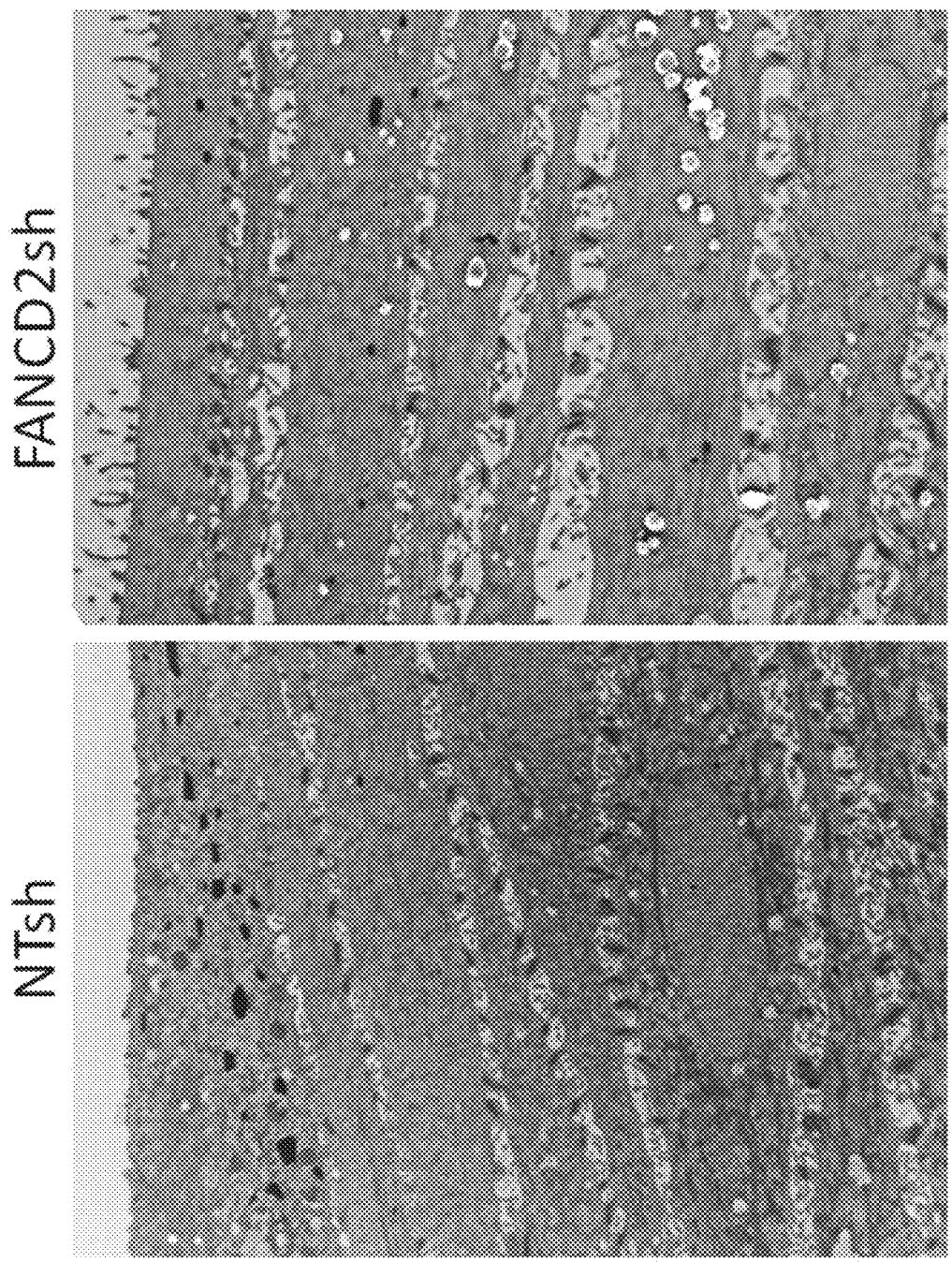

FIG. 28 shows FANCD2 deficient organotypic epithelial rafts harbor perturbations in membrane and adhesion characteristics. Organotypic epithelial rafts were generated from NTsh and FANCD2sh NIKS. EM images show tissue morphology at 4000× magnification.

Figure 29:
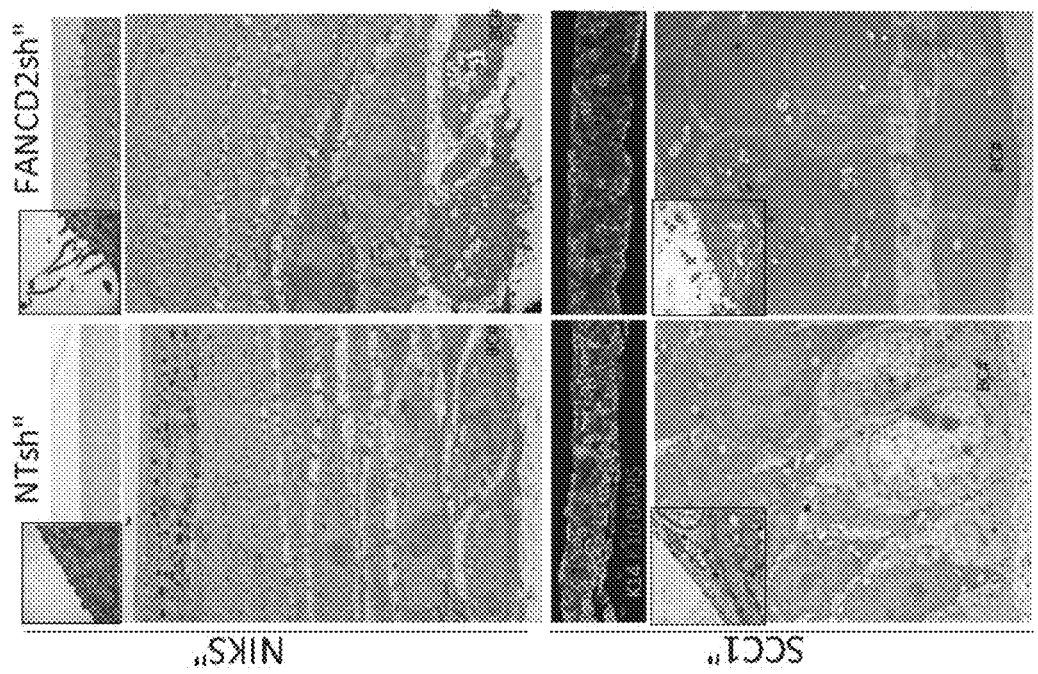

FIG. 29 shows FANCD2 deficient organotypic normal and tumor rafts harbor perturbations in differentiation and integrity. Organotypic rafts were generated from NTsh and FANCD2sh NIKS (top 2 panels) and NTsh and FANCD2sh deficient SCC1 head and neck cancer cell lines (bottom 2 panels). Top: protrusions and vesicles observed on the apical surface of the FANCD2 rafts (shown in FIG. 29) are enlarged at 40,000× (left insets). Basal cell adhesion abnormalities with intracellular vesicles were also observed. Bottom: immunofluorescence analysis indicated differentiation alterations in the FANCD2sh tumor rafts with increased accumulation of K10 positive differentiated cells. Abnormal differentiation, apical vesicle formation and basal cell adhesion defects are also observed by EM.

Figure 30:
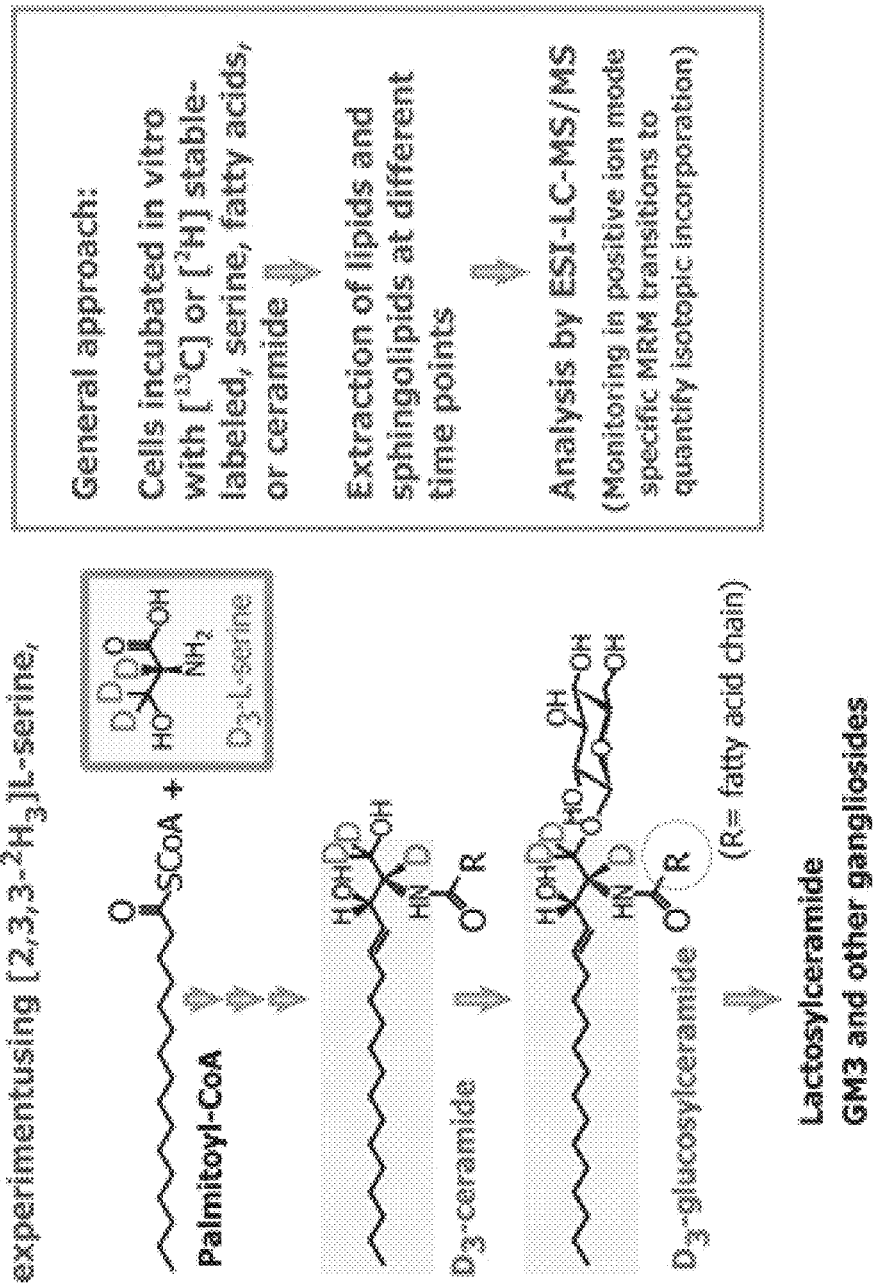

FIG. 30 shows use of stable isotope tracers to define the FA-pathway-dependent regulation of ganglioside metabolism.

Figure 31:
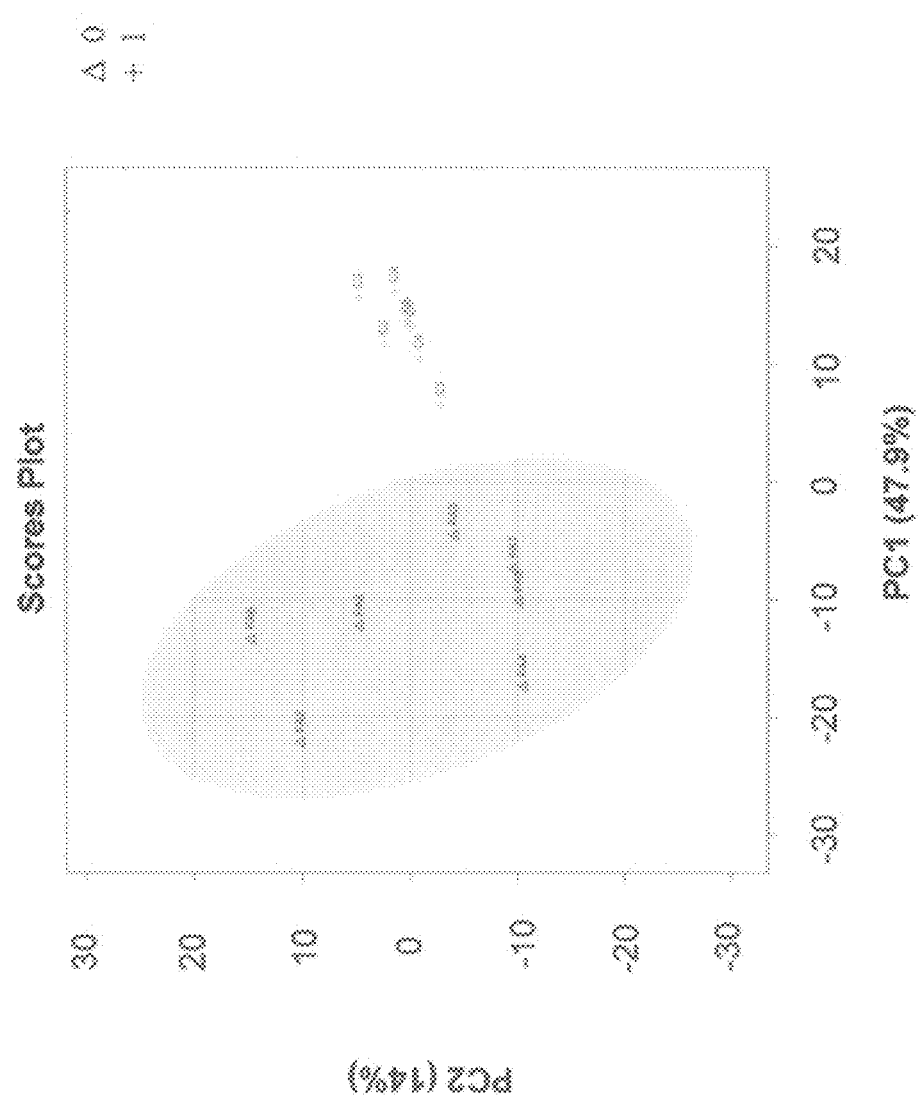

FIG. 31 shows mass spectrometry based untargeted metabolomics/lipidomics study of FA patient plasma along with age, gender matched controls showed clear separation by multivariate analysis, principle component analysis. Paired principle component analysis (PCA) plot based on 436 compounds acquired through MS metabolomics platform. Control (n=7, labeled C1-C7) are clustered (in lighter gray) and FA patients (n=7, labeled FA1-FA7) are clustered (in darker gray). Altered lipid class in FA include phospholipids, sphingolipids and sterols. Particularly, lysophospholipid including lysophosphocholine (LPC), lysophosphoethanoamine (LPE), and lysophosphatidic acid (LPA) showed consistent significant accumulation in FA plasma compared to control group.

Figure 32:
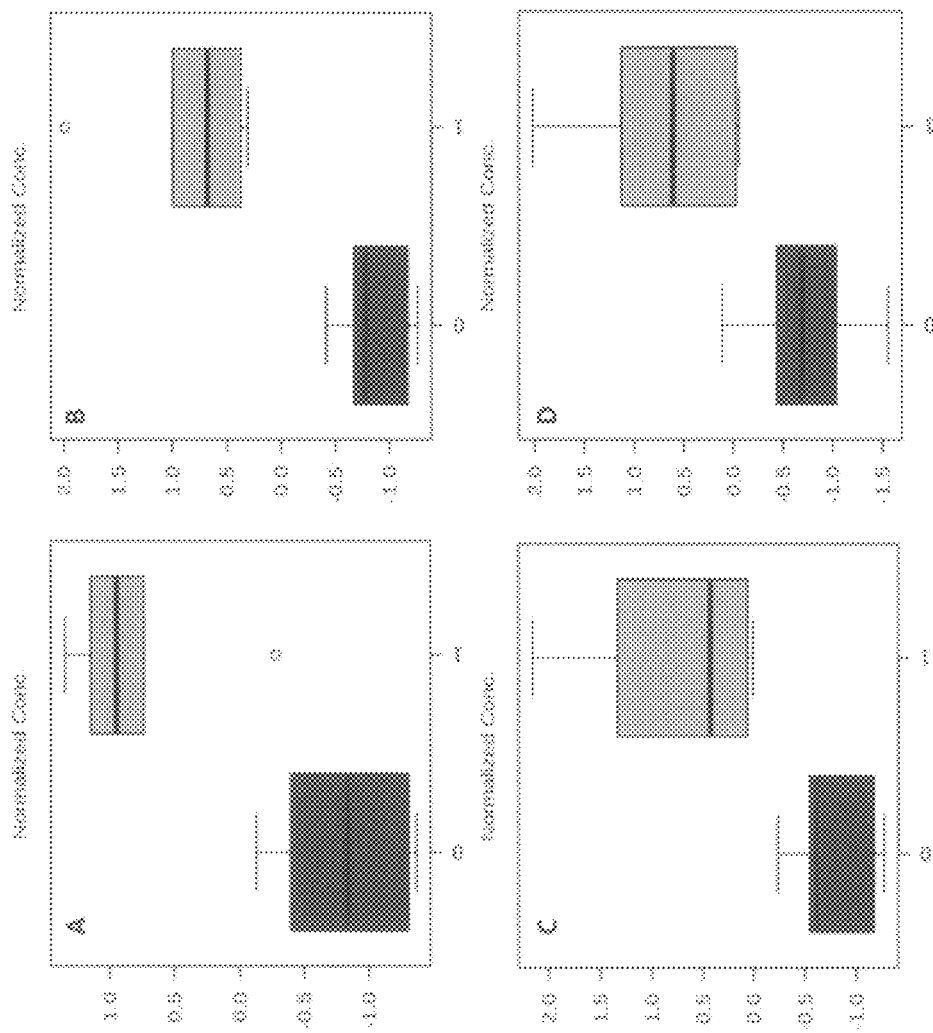

FIG. 32 shows an increased level of lysophosphatidylcholines in FA plasma. Data were based on quantitative analysis of each subspecies of lysophosphatidylcholines and T-test was done in pair wise fashion. Darker gray bar is for control group (n=7) and lighter graybar for FA group (n=7). (A) 18:0 LPC; (B) 16:0 LPC; (C) Total LPC; (D) 18:1 LPC. Lysophospholipid include both ester bond and ether bond linked species. Chain length include 14:0/14:1/16:0/16:1/18:0/18:1/18:2/18:3/20:3/20:4/22:5/22:6. The accumulation of lysophospholipid are projected to have anti-apoptosis effect through LPA mediated LPA2 and G protein activation.

Figure 33:
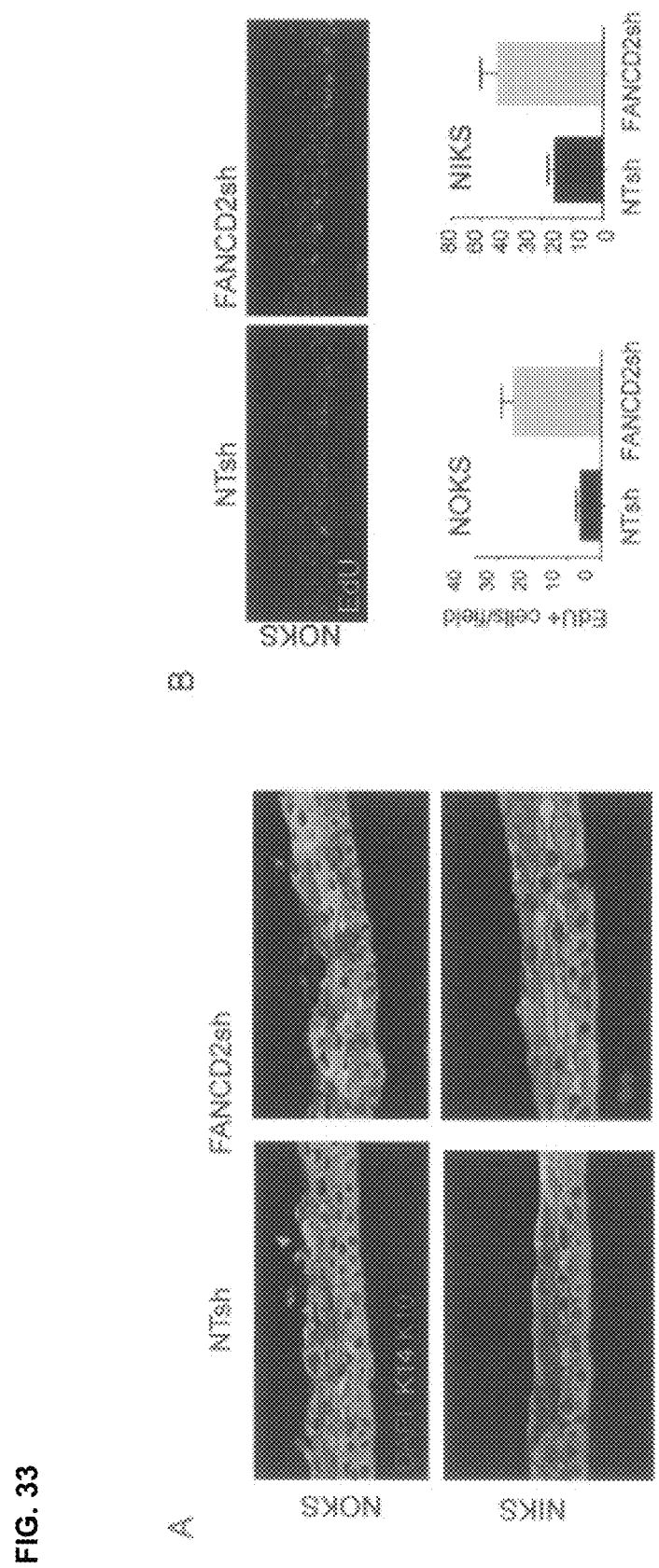

FIG. 33 shows loss of the FA pathway stimulates epidermal proliferation. A. Normal oral keratinocytes (NOKS) and normal skin keratinocytes (NIKS) were subjected to organotypic raft culture and sections stained by immunofluorescence (IF) for basal (K14) and differentiated (K10) cell markers. B. Edu incorporation was carried out for IF detection of proliferating cells. Quantitation for both NOKS and NIKS is shown.

Figure 34:
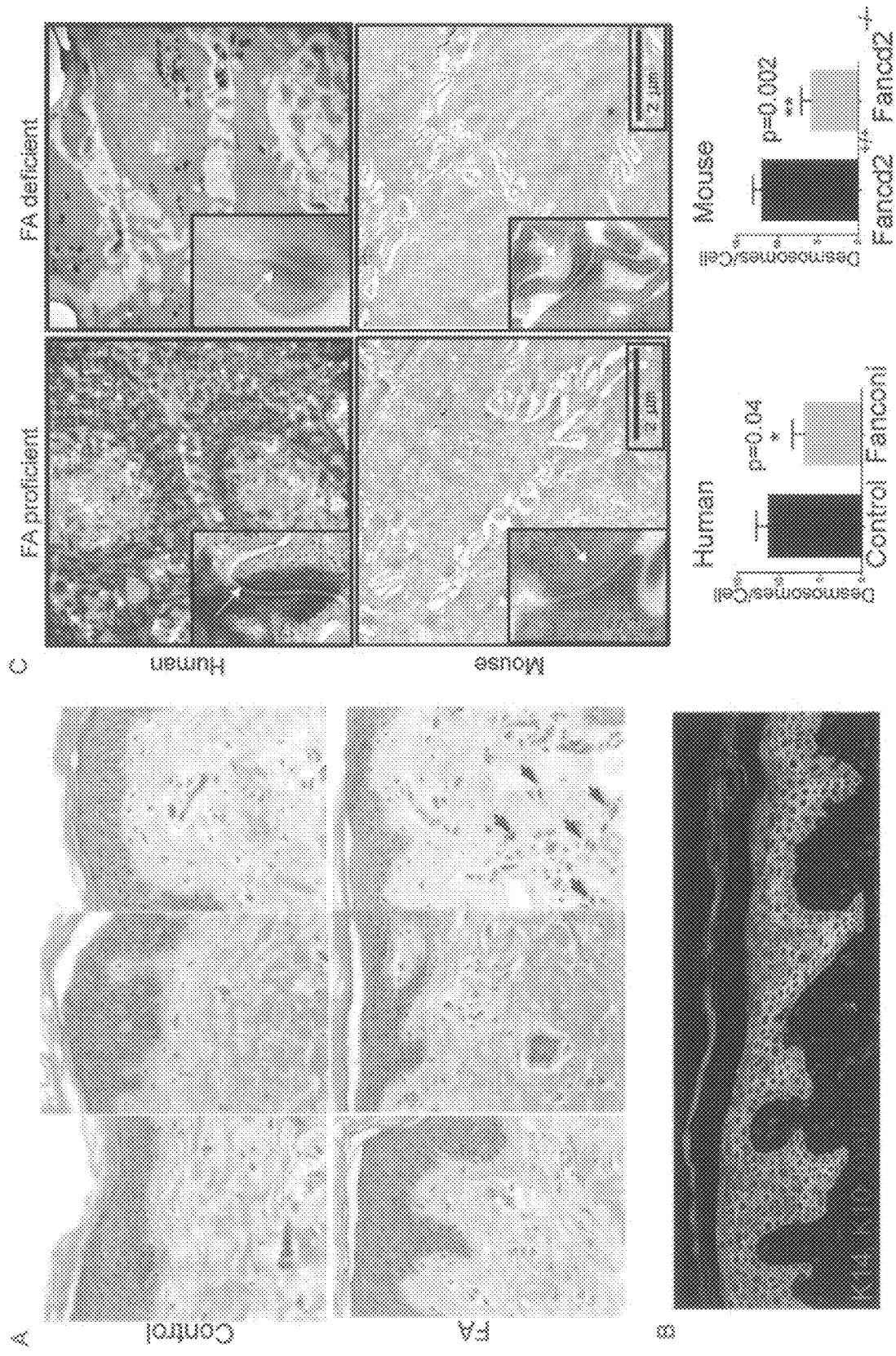

FIG. 34 shows ultrastructural adhesion abnormalities in the skin of individuals with FA. A. Skin punch biopsies from normal control versus FA subjects were fixed, sections and used for H&E staining. These were morphologically normal but exhibited pigment incontinence in 3/6 subjects in FA only which could not be explained by race and is consistent with basal cell injury. B. Skin-punch biopsy tissue, sectioned and immunostained for K14, K10 and DAPI.C. Representative EM images of skin-punch biopsies from 9 FA patients (no bone marrow transplant) and 5 controls (top), and tongue (mucosal) epidermis from 2 FancD2 knockout and 2 wild-type mice (bottom). Biopsies were processed and analyzed by EM. Desmosome counts were cell were significantly reduced.

Figure 35:
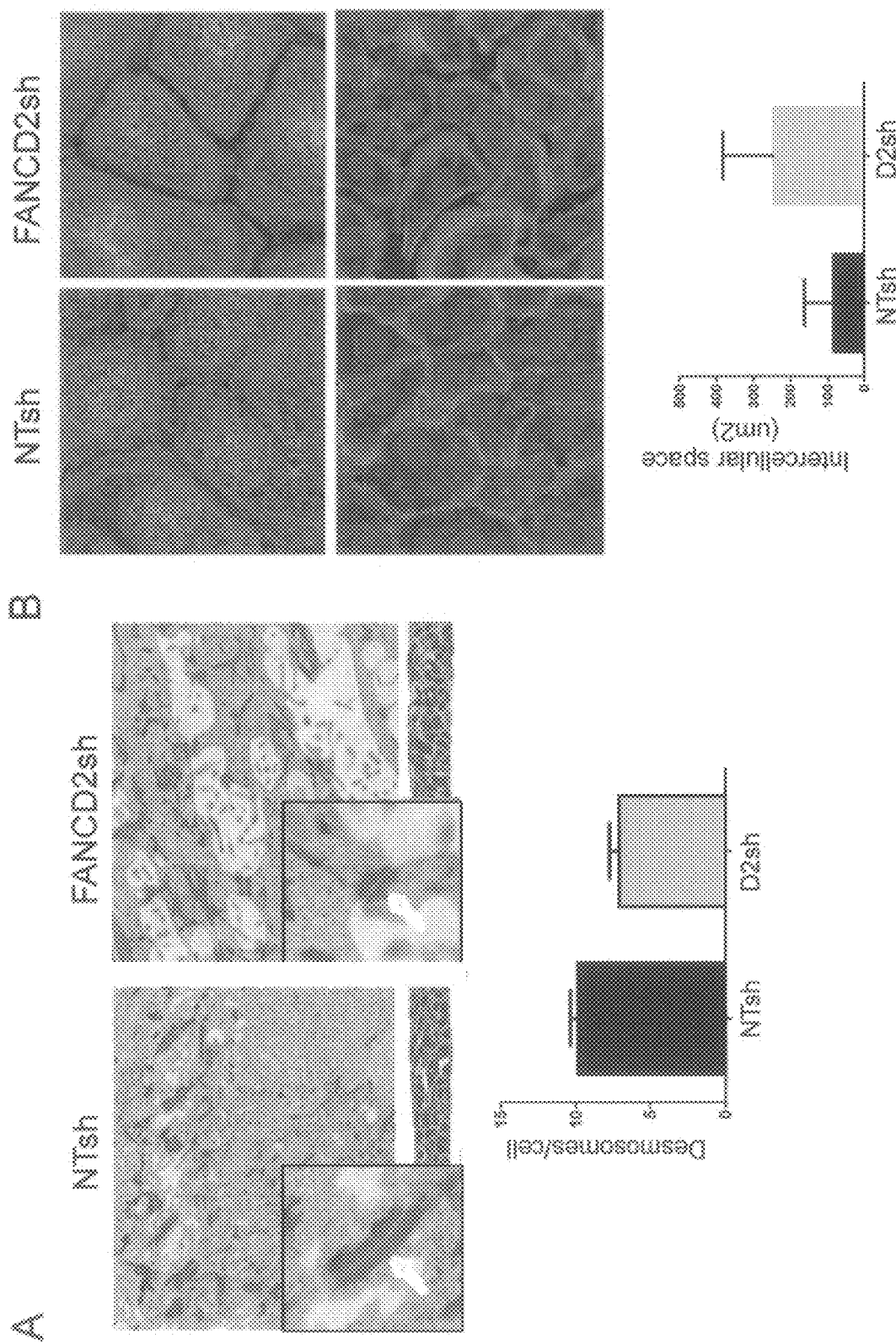

FIG. 35 shows the following: A. Representative EM images of NIKS-derived organotypic epithelial rafts independently transduced with either NTsh (n=2) or FANCD2sh (n=2). B. confocal microscopy of monolayer cells from A. NIKS in monolayer culture were immunostained for K14 (green), phalloidin (red) and DAPI and subjected to confocal microscopy to visualize intercellular gaps. Images of immunostained cytoskeletal elements were acquired on a Nikon A1 confocal using a 100×NA 1.45 objective, nyquist sampling, and a 1.2 A.U. pinhole. Z-stacks were acquired through the thickness of the cell layer (~7 um) using a 150 nm step size to allow for sufficient overlap of optical sections for 3D reconstruction. Intercellular spaces were quantified from 7 images each, using Nikon Elements General Analysis software. Binary thresholds were set to create a binary mask on phalloidin-low intensity gaps between cells. The area of this binary mask was quantified. Preliminary quantitation suggests more pronounced intercellular gaps.

Figure 36:
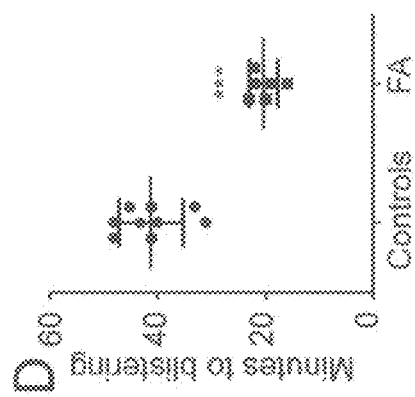

FIG. 36 shows time to blister formation in FA patients compared to age- and gender-matched control subjects.

Figure 37:
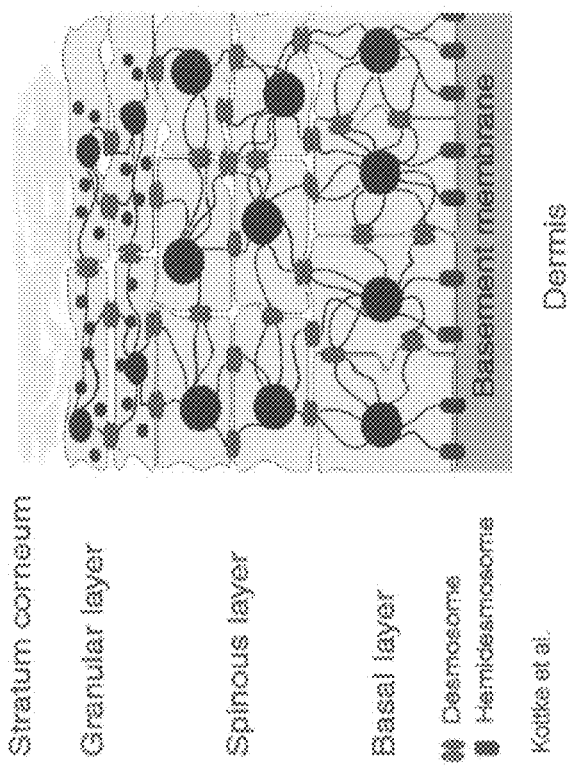

FIG. 37 shows a schematic of skin epidermis.

Figure 38:
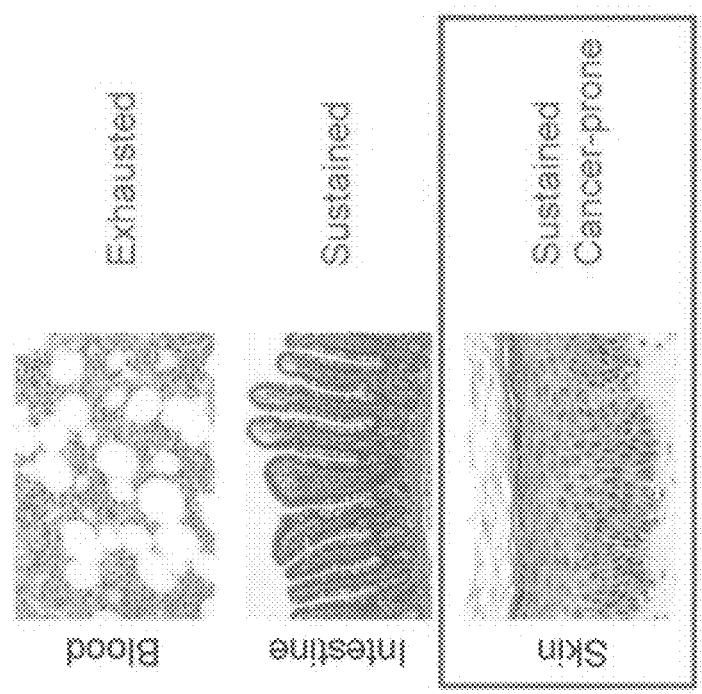
Figure 38:
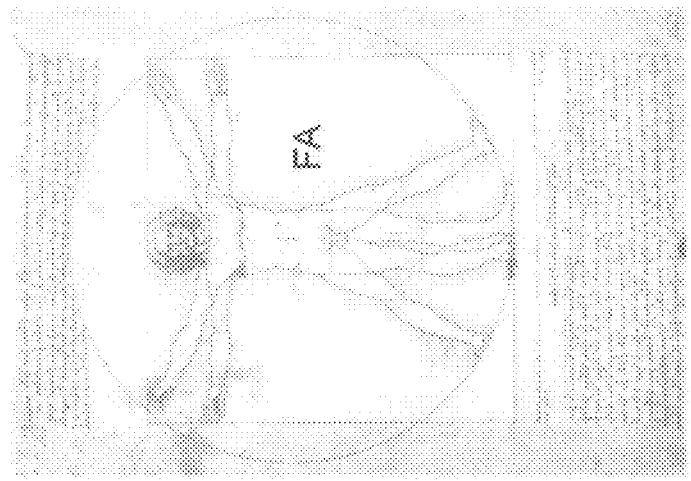
Figure 38:
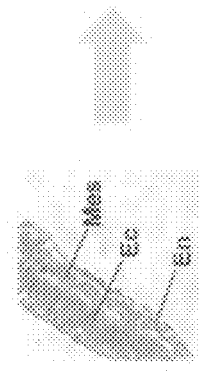

FIG. 38 shows a schematic of the 3 germ layers (ectoderm, mesoderm, endoderm) from which all organs derive.

Figure 39:
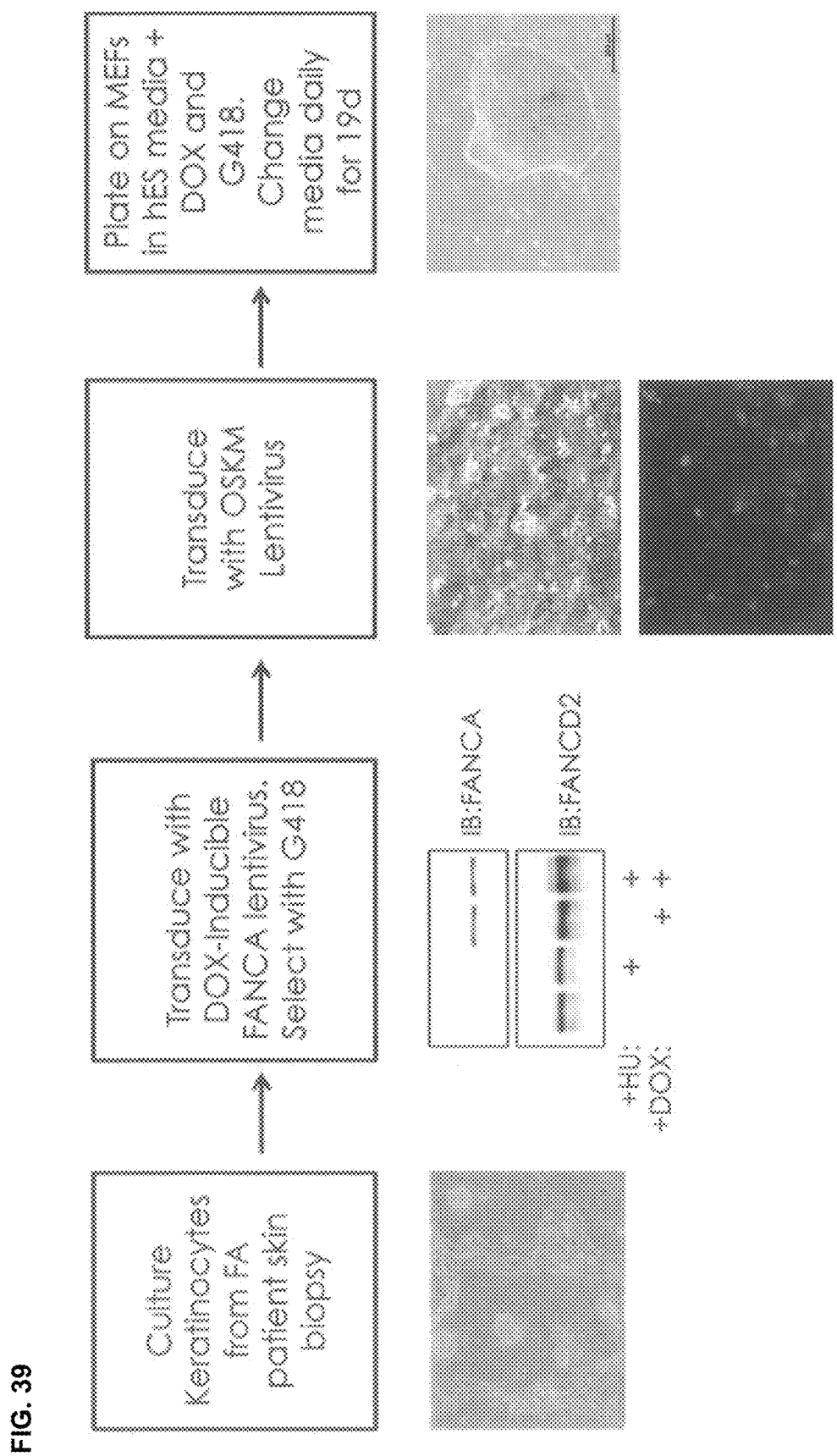

FIG. 39 shows a schematic representation of the derivation of iPSC with inducible complementation of the FA Pathway. FA patient keratinocytes (a keratinocyte colony is shown below on the left) were used for inducible expression of a complementing FA gene. These cells were transduced with a lentivirus expressing the FANCA gene under doxycycline (DOX)-inducible control. DOX-inducible expression of FANCA was confirmed, which reconstituted the functional FA core complex to monoubiquitinate FANCD2 upon treatment with hydroxyurea by western blot analysis. The cells were then subjected to reprogramming vectors expressing Oct4, Sox2, Klf4, c-myc (OSKM) and in the presence or absence of DOX (morphology and staining for nanog expression is shown). The DOX-treated cells formed iPS colonies. Several colonies were picked and cultured into stable iPS lines in the presence of DOX.

Figure 40:
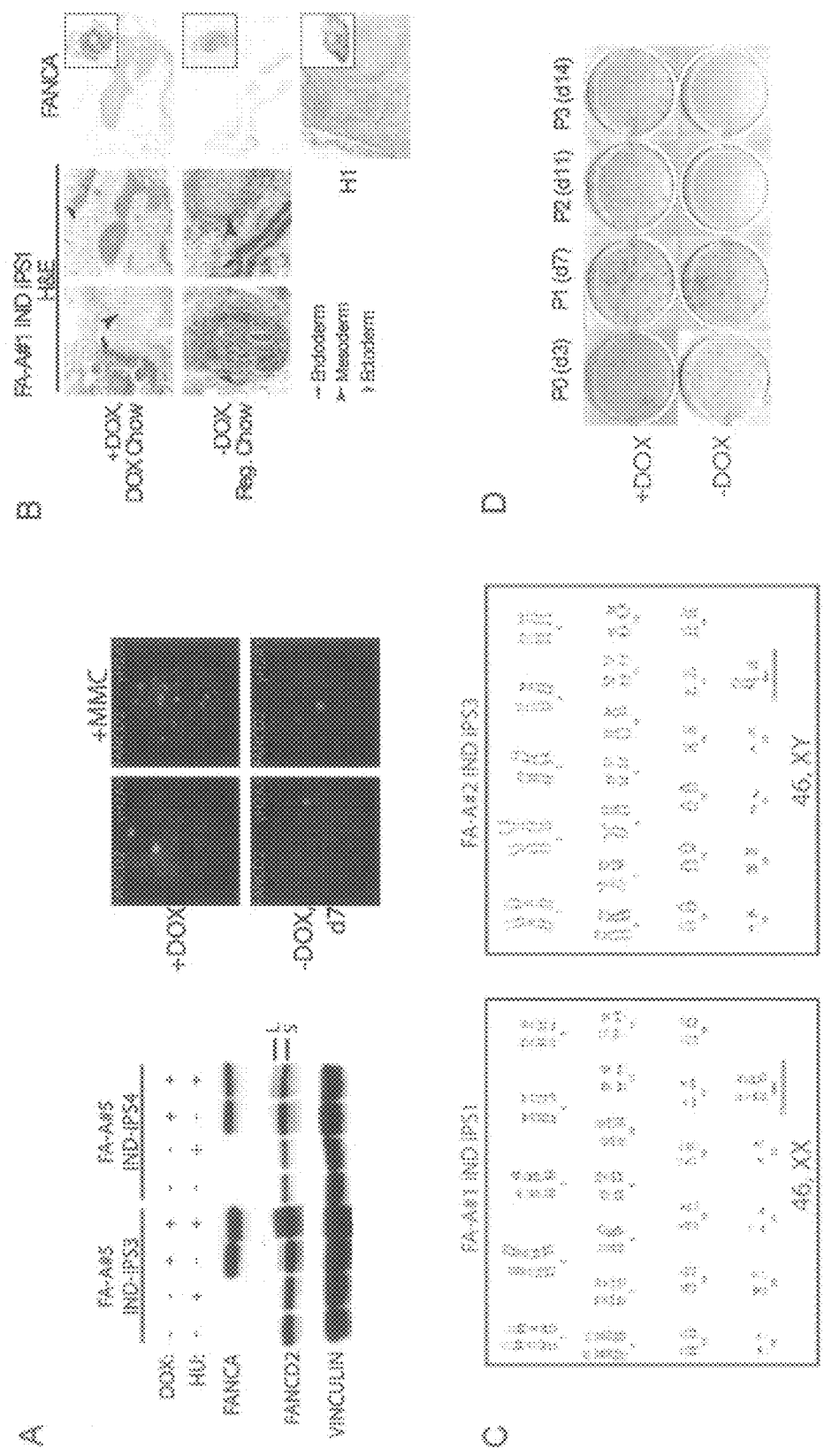

FIG. 40 shows FA loss is incompatible with iPSC self-renewal and the described model allows for directed differentiation into keratinocyte lineages and 3D epidermis. (A) Western blot analysis and FANCD2 foci formation in FA-inducible iPSC in cultures treated or untreated with DOX for 7 d, and treated or untreated with hydroxyurea. (B) H&E staining of sections of teratomas formed from these FA-inducible iPSCs. iPS cells were pre-treated with or without DOX, and then injected into the flanks of NSG mice fed DOX chow or regular chow. (C) Normal karyotypes of FA-inducible iPSC grown in DOX. (D) Progressive exhaustion of iPS cells grown without DOX (compared with with DOX) for 3 passages.

Figure 41:
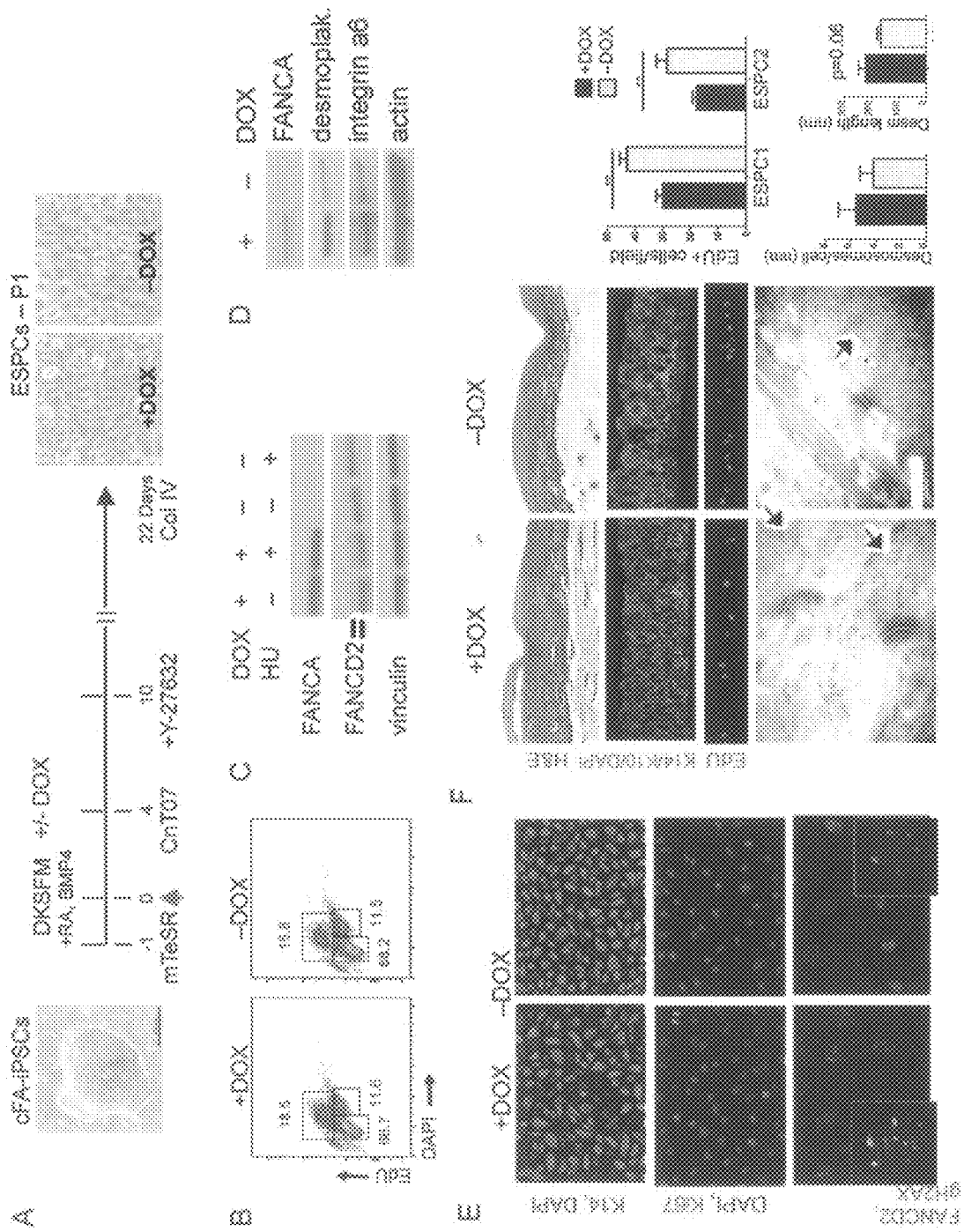

FIG. 41 shows differentiation of iPSC lines into skin +/- dox and thus +/- a functional FA pathway. FIG. 41A shows iPSC culture and DOX+ and DOX- ESPC cultures. FIG. 41B shows DOX+ and DOX- cell proliferation based on EdU staining. FIG. 41C and FIG. 41D shows FANCA and FANCD2 expression. FIG. 41E shows monolayer cultures stained with FANCD2, DAPI, and K14. FIG. 41F shows organotypic raft cultures.

Figure 42:
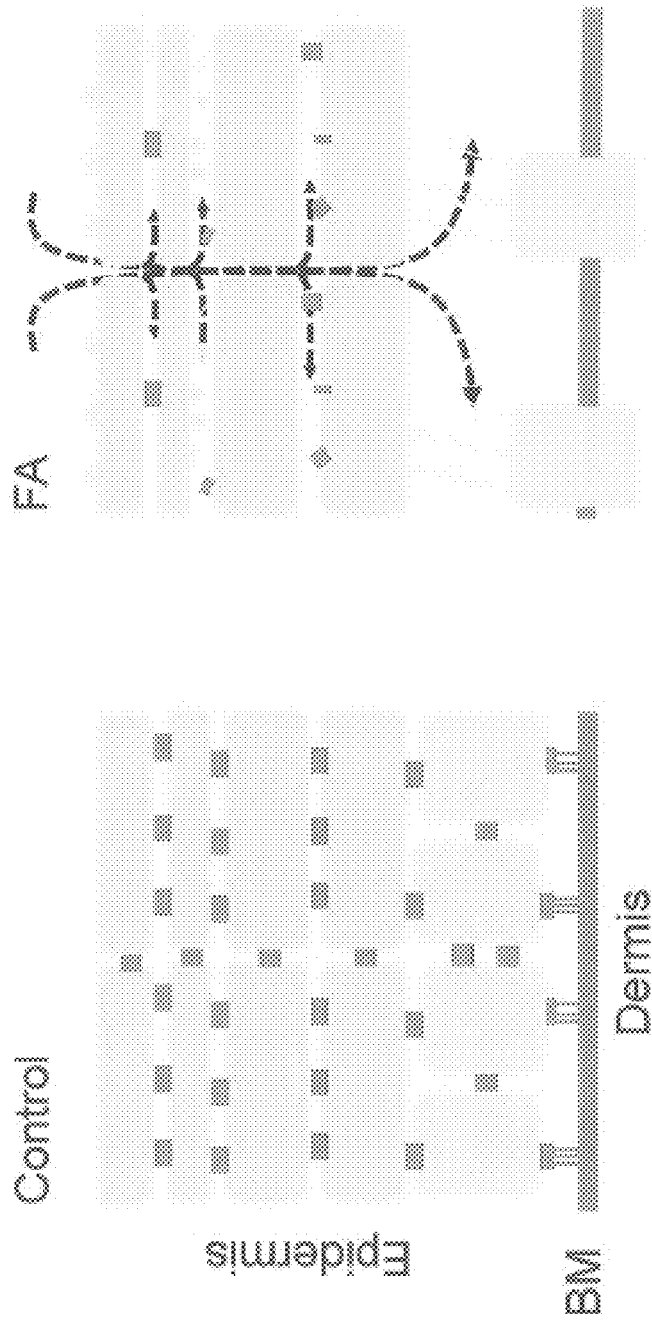

FIG. 42 shows a schematic representation of FA loss of function in epidermis tissue impairs structure and function.

The FA pathway controls lipid metabolism. FA is an established model for studying DNA repair. Patients have a unique susceptibility to leukemia and SCC. FA genes are mutated in sporadic SCC. The biological consequences of FA loss in normal and transformed keratinocytes are poorly understood.

FA is a model for inherited cancer susceptibility, representing DNA repair deficiencies that are yet to be identified. Early treatment of FA is critical and FA is likely under-diagnosed because there are no screening methods for detection of FA or other inherited DNA repair deficiencies. Thus, prospective FA biomarkers are needed. This is even more important because FA SCC cannot be treated with conventional approaches so there is a need for alternative therapies, including new biomarkers and drug targets for FA SCC, both inherited and sporadic. While sporadic tumors with FA mutations may be uniquely targetable, there are no rapid identification tests to identify.

The disclosure identifies FA biomarkers in cell models and human populations and defines targetable mechanisms where FA loss impairs cellular integrity and stimulates disease. FA has a unique metabolic signature, supported with FA patient immortalized skin keratinocytes-complemented (NMR), FA patient cancer cells-complemented (NMR); FA children versus unaffected siblings using urine (NMR/MS), FA children versus unaffected siblings using blood (MS), FA knockdown normal keratinocytes NIKS: control, FANCAsh, FANCD2sh (MS); and FA knockdown squamous carcinoma cells SCC: control, FANCAsh, FANCD2sh (MS). This signature reflects perturbations of the following membrane associated lipids: glycerophospholipids and sphingolipids, which are the building blocks of lipid bilayers, functioning with cholesterol in most biomembranes and key regulators of membrane plasticity, trafficking, and signaling in lipid rafts. FA cells have membrane perturbations; lipid de-regulation may be a global defect. FA-deficient SCC have abnormal membrane morphology and are invasive. Specifically, they have abnormal membrane extensions, activated Rac1 signaling, invasion that is rescued by cholesterol supplementation, quercetin, and equol. 23.

The biomarkers can be measured by one or a combination of methods including, but not limited to, immunoassay, enzyme-linked immunosorbent assay (ELISA), spectrophotometry, nuclear magnetic resonance (NMR), color imagery, dipstick, chemiluminescence, etc. The biomarks can be measured in one or a combination of samples including, but not limited to, urine, skin, blood, sweat, feces, tissue (biopsy), saliva, etc.

The following table shows metabolomics study data of FA cells.

FA Alters the NMR Metabolome in Normal and Transformed Keratinocytes

| Cell lines | Mahalanobis Distance (DM) | Two-sample T2 statistic | F-value | Critical F-value | Significance |
|---|---|---|---|---|---|
| IHK-1FA | 1.21 | 6.18 | 2.88 | 3.73 | No |
| IHK-2FA | 4.48 | 100.15 | 47.29 | 3.18 | Yes |
| HNc-1FA | 4.29 | 50.25 | 22.33 | 6.26 | Yes |
| HNc-2FA | 1.70 | 8.65 | 3.89 | 5.05 | No |
| HNc-1 | 17.50 | 918.56 | 413.35 | 5.05 | Yes |
| HNc-2 | 5.02 | 75.55 | 34.00 | 5.05 | Yes |
| HNc-3 | 12.16 | 443.45 | 99.55 | 5.05 | Yes |

FA Metabolic Alterations are Small but Significant

| Metabolites ID | IHK-1$^{FA}$ | IHK-2$^{FA}$ | HNC-1$^{FA}$ | HNC-2$^{FA}$ | HNC-1 | HNC-2 | HNC-3 |
|---|---|---|---|---|---|---|---|
| 3-Hydroxyisovalerate | 1.019 | 1.041 | 1.016 | 1.125 | 1.161 | 1.127 | 1.339 |
| Acetate | 1.011 | 1.014 | 0.916 | 0.989 | 1.060 | 1.693 | 1.315 |
| acetylcholine | 0.995 | 1.012 | 1.034 | 1.088 | 1.117 | 1.336 | 0.919 |
| Acetyllysine | 0.993 | 1.001 | 1.033 | 1.024 | 0.860 | 1.046 | 1.099 |
| Ala | 1.007 | 0.997 | 1.081 | 0.951 | 0.830 | 0.796 | 0.956 |
| Asp | 1.008 | 1.008 | 0.844 | 0.956 | 0.952 | 1.118 | 1.111 |
| AXP | 0.978 | 0.997 | 0.932 | 1.241 | 0.935 | 1.037 | 1.807 |
| Choline | 0.994 | 1.006 | 0.571 | 0.811 | 1.180 | 1.262 | 1.214 |
| Creatine | 1.033 | 0.994 | 1.019 | 1.115 | 0.881 | 1.010 | 1.147 |
| Creatine-P | 1.019 | 1.007 | 0.909 | 0.882 | 0.957 | 1.144 | 1.164 |
| Formate | 1.082 | 0.987 | — | 2.214 | 18.726 | 17.689 | 0.681 |
| Glucose | 0.984 | 1.002 | 0.881 | 0.795 | 1.656 | 0.937 | 0.984 |
| Glu | 1.008 | 0.998 | 0.936 | 1.003 | 0.877 | 0.963 | 0.942 |
| Gln | 0.980 | 1.024 | 0.947 | 0.853 | 0.913 | 1.155 | 1.195 |
| Gly | 1.002 | 0.989 | 0.945 | 0.926 | 0.900 | 0.914 | 0.878 |
| Glycerol-phosphocholine | 1.025 | 1.006 | 1.008 | 1.002 | 1.040 | 1.039 | 1.245 |
| GSH | 1.025 | 0.994 | 0.898 | 1.021 | 0.874 | 1.034 | 1.041 |
| Histamine | 1.033 | 0.936 | 0.303 | 1.741 | 1.721 | 1.262 | 2.621 |
| Ile | 0.996 | 1.005 | 1.023 | 1.039 | 0.994 | 0.968 | 0.972 |
| Isopropanol | 1.009 | 0.968 | 1.016 | 1.169 | 1.469 | 1.103 | 1.619 |
| Lactate | 0.999 | 0.999 | 1.068 | 1.030 | 1.041 | 0.810 | 0.809 |
| Leu | 1.002 | 0.999 | 0.925 | 0.972 | 0.983 | 0.955 | 1.041 |
| Lys | 0.993 | 1.001 | 1.117 | 1.081 | 0.711 | 0.755 | 0.439 |
| Met | 1.033 | 0.995 | 0.883 | 0.968 | 0.933 | 1.023 | 0.986 |
| Myo-Inositol | 1.007 | 1.000 | 0.898 | 0.967 | 0.959 | 1.073 | 0.996 |
| NAD+ | 1.089 | 0.997 | 1.765 | 1.436 | 0.834 | 1.255 | 0.617 |
| Ornithine | 0.990 | 1.001 | 0.920 | 0.972 | 0.806 | 1.106 | 1.025 |
| Phosphocholine | 1.035 | 0.994 | 0.950 | 0.969 | 1.147 | 1.131 | 1.031 |
| Phe | 0.996 | 1.004 | 0.931 | 0.993 | 0.960 | 0.986 | 0.979 |
| Succinate | 1.000 | 1.003 | 0.920 | 0.959 | 0.990 | 1.025 | 1.140 |
| Thr | 1.027 | 0.994 | 0.995 | 0.999 | 0.917 | 0.977 | 0.993 |
| Trp | 0.864 | 0.844 | 15.641 | 0.735 | 1.644 | 0.451 | — |
| Tyr | 1.002 | 1.000 | 0.949 | 0.950 | 0.952 | 0.925 | 0.991 |
| UDP-sugar | 1.033 | 0.984 | 1.074 | 1.072 | 0.830 | 0.935 | 0.909 |
| Val | 1.006 | 1.003 | 0.944 | 1.004 | 0.942 | 0.930 | 1.006 |

BOLD: numbers p-values < 0.05

Ontology Analyses Point to Amino Acid and Lipid Metabolism

| | Pathway | Total | Hits | p-value | Metabolites |
|---|---|---|---|---|---|
| 1 | Aminoacyl-tRNA biosynthesis | 75 | 14 | 7.07E−14 | Glu, Asp, Phe, Gln, Met, Val, Gly, Ala, Lys, Ile, Leu, Thr, Tyr, Trp |
| 2 | Nitrogen metabolism | 39 | 8 | 1.77E−08 | Formate, Phe, Tyr, Trp, Asp, AMP, Gln, Gly, Glu |
| 3 | Alanine, aspartate and glutamate metabolism | 24 | 5 | 1.07E−05 | Asp, Ala, Glu, Gln, Succinate |
| 4 | Glycine, serine and threonine metabolism | 48 | 6 | 2.80E−05 | Asp, Thr, Gly, Choline, Creatine, Trp |
| 5 | Valine, leucine and isoleucine biosynthesis | 27 | 4 | 0.000365 | Thr, Val, Leu, Ile |
| 6 | Arginine and proline metabolism | 77 | 6 | 0.000411 | Glu, Gln, Asp, Ornithine, Creatine, Phosphocreatine |
| 7 | Glutathione metabolism | 38 | 4 | 0.001384 | Ornithine, GSH, Gly, Glu |
| 8 | Glycerophospholipid metabolism | 39 | 4 | 0.001528 | Phosphorylcholine, Glycerophosphocholine, Choline, Acetylcholine |
| 9 | Phenylalanine, tyrosine and tryptophan biosynthesis | 27 | 3 | 0.005029 | Phe, Trp, Tyr |
| 10 | Cysteine and methionine metabolism | 56 | 4 | 0.005822 | Asp, Ala, GSH, Met |
| 11 | Glycolysis or Gluconeogenesis | 31 | 3 | 0.007454 | Glucose, Lactate, Acetate |
| 12 | Lysine biosynthesis | 32 | 3 | 0.008152 | Asp, Acetyllysine, Lys |
| 13 | Pyruvate metabolism | 32 | 3 | 0.008152 | Lactate, Formate, Acetate |
| 14 | D-Glutamine and D-glutamate metabolism | 11 | 2 | 0.008741 | Glu, Gln |
| 15 | Propanoate metabolism | 35 | 3 | 0.01047 | Val, Succinate, Lactate |
| 16 | Valine, leucine and isoleucine degradation | 40 | 3 | 0.01511 | Val, Leu, Ile |

-continued

| | Pathway | Total | Hits | p-value | Metabolites |
|---|---|---|---|---|---|
| 17 | Galactose metabolism | 41 | 3 | 0.016157 | UDP-sugars, glucose, Myo-inositol |
| 18 | Cyanoamino acid metabolism | 16 | 2 | 0.018298 | Gly, Asp |
| 19 | Histidine metabolism | 44 | 3 | 0.01954 | Histamine, Glu, Asp |
| 20 | Phenylalanine metabolism | 45 | 3 | 0.020749 | Phe, Succinate, Tyr |
| 21 | Taurine and hypotaurine metabolism | 20 | 2 | 0.028031 | Ala, Acetate |
| 22 | Selenoamino acid metabolism | 22 | 2 | 0.033523 | Ala, Acetate |
| 23 | Thiamine metabolism | 24 | 2 | 0.0394 | Gly, Tyr |
| 24 | Pantothenate and CoA biosynthesis | 27 | 2 | 0.048889 | Asp, Val |
| 25 | Methane metabolism | 34 | 2 | 0.073797 | Formate, Met |

Feature selection reveals lipids are classifiers of FA (VIPs)

| NTsh v FANCD2sh | | NTsh v FANCAsh | |
|---|---|---|---|
| Compound ion | Metabolite | Compound ion | Metabolite |
| 2.96_656, 4469 n | PA(O-16:0/18:3(9Z, 12Z, 15Z)) | 2.96_656.4469 m/z | PA(O-16:0/18:3(9Z, 12Z, 15Z)) |
| 0.78_383.0870 m/z | Unknown | 2.11_652.4960 m/z | DG(18:4(6Z, 9Z, 12Z, 15Z)/20:5 (5Z, 8Z, 11Z14Z, 17Z)/0:0)[iso2] |
| 2.11_652.4960 m/z | DG(18:4(6Z, 9Z, 12Z, 15Z)/20:5 (5Z, 8Z, 11Z, 14Z, 17Z)/0:0[iso2] | 3.25_688.4966 m/z | PE(14:0/18:2(9Z, 12Z)) |
| 1.23_422.4097 m/z | 5-alpha-hydroxycholesterol | 1.23_422.4097 m/z | 5alpha-hydroxycholesterol |
| 3.25_688.4966 m/z | PE(14:0/18:2)9Z, 12Z)) | 1.54_308.2948 m/z | N-oleoyl ethanolamine |
| 1.58_452.4560 m/z | Unknown | 1.58_452.4560 m/z | Unknown |
| 1.54_308.2948 m/z | N-oleoyl ethanolamine | 1.33_452.4197 m/z | 6-deoxoteasterone |
| 1.33_452.4197 m/z | 6-deoxoteasterone | 14.32_784.6615 m/z | TG(14:1(9Z)/14:1(9Z)/18:4 (6Z, 9Z, 12Z, 15Z))[iso3] |
| 0.79_346.1884 m/z | Tetranor-PGEM | 13.78_756.6319 m/z | GlcCer(d18:1/20:0) |
| 0.79_348.3255 m/z | MG(16:0/0:0/0:0) | 0.82_392.2537 m/z | N-oleoyl alanine |
| 14.32_784.6615 m/z | TG(14:1(9Z)/14:1(9Z))/18:4 (6Z, 9Z, 12Z, 15Z))[iso3] | 1.58_530.2647 n | PG(20:5(5Z, 8Z, 11Z, 14Z, 17Z)/0:0) |
| 13.78_756.6319 m/z | GlcCer(d18:1/20:0) | 1.35_530.2651 n | PG(20:5(5Z, 8Z, 11Z, 14Z, 17Z)/0:0) |
| 0.79_346.3099 m/z | Tetranoor-PGEM | | |

| | | | |
|---|---|---|---|
| up | phosphatidic acid | | |
| | Phosphatidylethanolamine | 5alpha-hydroxycholesterol (sterol lipid) | |
| | Phosphatidylglycerol | 6-deoxoteasterone (sterol lipid) | |
| down | Diacylglycerol | | |
| | Glucosylceramide | | |
| | N-oleoyl ethanolamine | | |

40

Correlation Networks (Partial of Up-Regulated Lipid Compounds)

| Compound_ion | p-value | Description | Fold change |
|---|---|---|---|
| 2.11_652.496 | 1.64E−06 | "DG(18:4(6Z, 9Z, 12Z, 15Z)/20:5(5Z, 8Z, 11Z, 14Z, 17Z)/0:0)[iso2]" | 18.5446152 |
| 1.58_452.456 | null | "PG(20:5(5Z, 8Z, 11Z, 14Z, 17Z)/0:0)" | null |
| 1.23_422.409 | 1.62E−07 | 5alpha-hydroxycholesterol | 22.39438763 |
| 1.33_452.419 | 2.01E−11 | 6-deoxoteasterone | 13.85468195 |
| 1.54_308.294 | 7.36E−07 | N-oleoyl ethanolamine | 21.78210032 |
| 6.02_614.432 | 5.47E−08 | PE-NMe(14:0/14:0) | 2.287976714 |

Metabolomics studies were performed on urine samples from individuals with FA. NMR and MS metabolomics revealed a unique FA signature. There were ten patients each with three technical replicates for each sample. Urinary polar metabolites were assessed. Sixty-six distinct compounds were key features, lipid regulation was prominent: phosphatidylcholine, phosphatidylserine, linoleic acid, 7-dehydrodesmosterol, cholesterylacetate.

High phenylalanine in FA urine

| | Absolute intensity | | | | | | | |
|---|---|---|---|---|---|---|---|---|
| | Leu (abs) | Leu-IS (abs) | Met (abs) | Met-IS (abs) | Phe (abs) | Phe-IS (abs) | Tyr (abs) | Tyr-IS (abs) |
| 13AcylcarnAC1 | 7.94E+04 | 8019.52 | 1.05E+04 | 8616.95 | 2.21E+04 | 8.82E+04 | 0 | 6334.49 |
| 13AcylcarnAC2 | 3.54E+04 | 9497.1 | 1.09E+04 | 1.38E+04 | 29100.00 | 4.15E+04 | 0 | 8451.6 |

-continued

High phenylalanine in FA urine

Absolute intensity

| | Leu (abs) | Leu-IS (abs) | Met (abs) | Met-IS (abs) | Phe (abs) | Phe-IS (abs) | Tyr (abs) | Tyr-IS (abs) |
|---|---|---|---|---|---|---|---|---|
| 13AcylcarnAC3 | 8.01E+04 | 5112.67 | 2126.24 | 6769.93 | 4.00E+04 | 7.14E+04 | 0 | 1.11E+04 |
| 13AcylcarnAC4 | 8.68E+04 | 7759.52 | 8226.26 | 6273.56 | 2.39E+04 | 6.94E+04 | 0 | 1.50E+04 |
| 13AcylcarnAC5 | 1.43E+05 | 1.13E+04 | 1.24E+04 | 3.82E+04 | 35640.00 | 7.11E+04 | 4.43E+04 | 9527.97 |
| 13AcylcarnS1 | 5.67E+04 | 1.55E+04 | 1.17E+04 | 1871.73 | 1.88E+04 | 1.32E+05 | 0 | 9166.39 |
| 13AcylcarnS2 | 1.26E+05 | 3723.45 | 7359.56 | 9.46E+04 | 0.00E+00 | 4.20E+04 | 0 | 3377.85 |
| 13AcylcarnS3 | 9.91E+04 | 8571.59 | 1.21E+04 | 7227.12 | 21820.00 | 1.25E+05 | 0 | 8093.91 |
| 13AcylcarnS4 | 7.23E+04 | 5538.46 | 1.04E+04 | 9500.63 | 4.15E+04 | 7.01E+04 | 0 | 1.58E+04 |
| 13AcylcarnS5 | 4.12E+04 | 9747.25 | 9042.13 | 4939.47 | 2.56E+04 | 7.90E+04 | 4.59E+04 | 1.21E+04 |
| AC group | 8.49E+04 | 8.33E+03 | 8.83E+03 | 1.47E+04 | 2.41E+04 | 6.83E+04 | 8.87E+03 | 1.01E+04 |
| S group | 7.90E+04 | 8.61E+03 | 1.01E+04 | 2.36E+04 | 2.69E+04 | 8.96E+04 | 9.18E+03 | 9.72E+03 |
| S/AC | 0.93 | 1.03 | 1.14 | 1.61 | 0.79 | 1.31 | 1.04 | 0.96 |

Phenylalanine - used to form acetoacetyl-coA

High phenylalanine in FA urine

Concentration (uM)-based on ratio to IS

| The | Leu | Asp | Lys | Met | Phe | Tyr | Glutamic acid |
|---|---|---|---|---|---|---|---|
| 395.95 | 289.34 | 0 | 1126.93 | 6.8 | 3.01 | 0 | 0 |
| 148.87 | 92.54 | 0 | 261.78 | 4.42 | 14.21 | 0 | 0 |
| 626.33 | 353.27 | 513.75 | 820.97 | 1.76 | 6.73 | 0 | 78.96 |
| 447.5 | 167.62 | 57.69 | 1009.01 | 7.34 | 4.13 | 0 | 0 |
| 507.87 | 87.96 | 235.2 | 100.07 | 1.82 | 6.02 | 148.87 | 0 |
| 146.73 | 24.65 | 0 | 3710.82 | 34.91 | 1.71 | 0 | 0 |
| 1351.37 | 127.73 | 359.18 | 52.12 | 0.44 | 0.00 | 0 | 0 |
| 462.27 | 168.24 | 203.57 | 1089.11 | 9.33 | 2.09 | 0 | 83.33 |
| 522.12 | 196.68 | 177.81 | 320.6 | 6.13 | 7.10 | 0 | 0 |
| 168.96 | 78.92 | 184.17 | 794.81 | 10.25 | 3.88 | 120.99 | 0 |
| 425.30 | 198.15 | 161.33 | 663.75 | 4.43 | 6.82 | | |
| 530.29 | 119.24 | 184.95 | 1193.49 | 12.21 | 3.70 | | |
| 1.26 | 0.60 | 1.15 | 1.80 | 2.76 | 0.54 | | |

Phenylalanine - used to form acetoacetyl-coA

Sixty-six putative biomarkers distinguished FA urine, shown in the following table:

| Description | Anova (p) | Max Fold Change |
|---|---|---|
| 4-Guanidinobutanoic acid | 3.61E-08 | 42.5 |
| 1-Methylhistidine | 8.85E-08 | 9.9 |
| Ne,Ne dimethyllysine | 6.79E-07 | 19.7 |
| L-Histidine | 2.75E-06 | 46.0 |
| 2-Hydroxylauroylcarnitine | 1.27E-05 | 41.2 |
| alpha-Tocopherolquinone | 2.08E-05 | 18.0 |
| N6,N6,N6-Trimethyl-L-lysine | 2.29E-05 | 16.0 |
| L-Histidinol | 2.88E-05 | 5.8 |
| Lactapiperanol C | 5.97E-05 | 4.2 |
| L-2, 4-diaminobutyric acid | 6.55E-05 | 44.6 |
| MG(20:1(11Z)/0:0/0:0) | 6.96E-05 | 7.5 |
| Alanyl-Histidine | 8.01E-05 | 267.5 |
| Isoleucyl-Leucine | 9.31E-05 | 38.7 |
| Linoleic acid | 0.00011 | 5.7 |
| 2-Hydroxyestrone sulfate | 0.00013 | 63.6 |
| Serinyl-Histidine | 0.00014 | 6.7 |
| (9R, 10S, 12Z)-9, 10-Dihydroxy-8-oxo-12-octadec | 0.00014 | 29.2 |
| L-Glutamine | 0.00014 | 100.1 |
| Hydroxyvalerylcarnitine | 0.00014 | 137.2 |
| Methyl 6-O-galloyl-beta-D-glucopyranoside | 0.00018 | 6.3 |
| Palmitic amide | 0.00025 | 3.7 |
| Dopamine 4-sulfate | 0.00028 | 32.7 |
| Fistulosin | 0.00029 | 13.4 |
| N-Acryloylglycine | 0.00031 | 5.0 |
| Dimethyl succinate | 0.00032 | 5.3 |
| N-Undecanoylglycine | 0.00041 | 8.2 |
| 14, 15-DiHETrE | 0.00049 | 2.370 |
| Decanoylcarnitine | 0.00064 | 3.3 |
| Physoperuvine | 0.00066 | 13.2 |
| (S)-N-(4, 5-Dihydro-1-methyl-4-oxo-1H-imidazol- | 0.00069 | 3.8 |
| Methylpyrazine | 0.00074 | 7.5 |
| Tryptophyl-Histidine | 0.00077 | 7.1 |
| Galactinol | 0.00085 | 9.3 |
| 2, 6-Dimethylpyrazine | 0.0009 | 6.9 |
| Tridemorph | 0.00092 | 7.3 |
| (13R, 4R)-8-Labdene-13, 14, 15-triol | 0.00095 | 3.2 |
| Isofenphos | 0.00099 | 7.8 |
| MG(18:3(9Z, 12Z, 15Z)/0:0/0:0) | 0.00105 | 5.5 |
| N,N-Dimethylsphingosine | 0.00107 | 8.9 |
| Hydroxyprolyl-Glutamine | 0.00111 | 4.4 |
| Cholesteryl acetate | 0.00119 | 32.5 |
| 2-O-a-L-Fucopyranosyl-galactose | 0.0012 | 9.5 |
| Ascladiol | 0.00156 | 4.1 |
| isonicotinylglycine | 0.00159 | 5.7 |
| 3-Hydroxyhippuric acid | 0.00165 | 3.6 |
| Tridodecylamine | 0.00206 | 36.2 |
| 2-Hydroxymyristoylcarnitine | 0.00397 | 7.5 |
| 5-Methyldeoxycytidine | 0.0046 | 46.0 |
| 7-Dehydrodesmosterol | 0.00462 | 21.1 |
| Dimethyl-L-arginine | 0.00464 | 3.3 |
| Cytosine | 0.00497 | 6.3 |
| 3'-AMP | 0.00541 | 448.9 |
| 2, 8-Dihydroxyquinoline-beta-D-glucuronide | 0.00554 | 43.1 |
| 6-Keto-decanoylcarnitine | 0.00569 | 3.4 |
| p-Aminobenzoic acid | 0.00606 | 321.1 |
| 12(13)Ep-9-KODE | 0.00663 | 24.4 |
| Docosanamide | 0.00728 | 3.8 |
| Gamma-glutamyl-Hydroxyproline | 0.00733 | 5.6 |
| 3-acetamidobutanal | 0.00815 | 76.9 |
| Galactose-beta-1, 4-xylose | 0.0082 | 4.1 |
| N-Acetylglutamic acid | 0.00825 | 4.0 |
| Hydroxyprolyl-Valine | 0.00842 | 6.5 |
| L-Glutamine | 0.00914 | 4.1 |
| PC(18:4(6Z, 9Z, 12Z, 15Z)/20:5 (5Z, 8Z, 11Z, 14Z, 17Z) | 0.01048 | Infinity |
| PS(18:0/18:2(9Z, 12Z)) | 0.01098 | 3.8 |
| 2-Furoylglycine | 0.00069 | 3.4 |

Putative biomarkers from FA cells and patient plasma shown below.

| Metabolite | Identified metabolites | Regulation in FA gene knockdown or disease | Matrix detected |
|---|---|---|---|
| Ganglioside GM3 | Ganglioside GM3 (d34:1), | increase | Cell |
| | Ganglioside GM3 (d36:1), | | |
| | Ganglioside GM3 (d38:1), | | |
| | Ganglioside GM3 (d40:1), | | |
| | Ganglioside GM3 (d42:1), | | |
| | Ganglioside GM3 (d42:2) | | |
| Ganglioside GM1 | Ganglioside GM1 (d34:1), | increase | Cell |
| | Ganglioside GM1 (d36:1), | | |
| | Ganglioside GM1 (d38:1), | | |
| | Ganglioside GM1 (d40:1), | | |
| | Ganglioside GM1 (d42:1), | | |
| | Ganglioside GM1 (d42:2) | | |
| Ganglioside GD1 | Ganglioside GD1 (d34:1), | increase | Cell |
| | Ganglioside GD1 (d36:1), | | |
| | Ganglioside GD1 (d38:1), | | |
| | Ganglioside GD1 (d40:1), | | |
| | Ganglioside GD1 (d42:1), | | |
| | Ganglioside GD1 (d42:2) | | |
| Ganglioside GD3 | Ganglioside GD3 (d34:1), | increase | Cell |
| | Ganglioside GD3 (d36:1), | | |
| | Ganglioside GD3 (d38:1), | | |
| | Ganglioside GD3 (d40:1), | | |
| | Ganglioside GD3 (d42:1), | | |
| | Ganglioside GD3 (d42:2) | | |
| Lactosylceramide | Lactosylceramide (d34:1), | increase | Cell |
| | Lactosylceramide (d36:1), | | |
| | Lactosylceramide (d38:1), | | |
| | Lactosylceramide (d40:1), | | |
| | Lactosylceramide (d42:1), | | |
| | Lactosylceramide (d42:2) | | |

Putative biomarkers from FA cells and patient plasma are shown below.

| Metabolite class | Metabolite Description | Alteration in FA patient plasma |
|---|---|---|
| LPE | LysoPE(20:1(11Z)/0:0) | up |
| | LysoPE(20:0/0:0) | up |
| | LysoPE(18:1(11Z)/0:0) | up |
| | LysoPE(18:0/0:0) | up |
| | LysoPE(0:0/18:0) | up |
| LPC | LysoPC(20:4) | up |
| | LysoPC(20:3) | up |
| | LysoPC(18:2) | up |
| | LysoPC(18:1) | up |
| | LysoPC(18:0) | up |
| | LysoPC(16:1) | up |
| | LysoPC(16:0) | up |
| | LysoPC(14:0) | up |
| LPA | LPA(P-16:0e) | up |
| | LPA(16:0) | up |
| | LPA(18:2) | up |
| | LPA(18:1) | up |
| | LPA(18:0) | up |
| | LPA(20:4) | up |
| | LPA(22:6) | up |
| Phosphatidylcholine | PCe 40:6 | Down |
| | PCe 40:6 | Down |
| | PCe 38:6 | Down |
| | PCe 38:6 | Down |
| | PCe 38:5 | Down |
| | PCe 38:4 | Down |
| | PCe 38:4 | Down |
| | PCe 38:3 | Down |
| | PCe 36:4 | Down |
| | PC(P-18:1(9Z)/22:2(13Z, 16Z)) | Down |
| | PC(P-18:0/22:4(7Z, 10Z, 13Z, 16Z)) | Down |
| | PC(o-22:2(13Z, 16Z)/22:3 (10Z, 13Z, 16Z)) | Down |
| | PC(o-22:1(13Z)/20:4 (8Z, 11Z, 14Z, 17Z)) | Down |
| | PC(o-22:0/22:6(4Z, 7Z, 10Z, 13Z, 16Z, 19Z)) | Down |
| | PC(o-22:0/20:4(8Z, 11Z, 14Z, 17Z)) | Down |
| | PC(o-22:0/20:4(8Z, 11Z, 14Z, 17Z)) | Down |
| | PC(18:1(9Z)/22:0) | Down |
| | PC 40:7 | Down |
| | PC 40:5 | Down |
| | PC 40:4 | Down |
| | PC 38:5 | Down |
| Phosphatidyl-ethanolamine | PEp 38:4 | Down |
| | PE(P-18:1(9Z)/22:2(13Z, 16Z)) | Down |
| | PE(P-18:0/22:4(7Z, 10Z, 13Z, 16Z)) | Down |
| | PE(P-18:0/20:3(8Z, 11Z, 14Z)) | Down |
| | PE(24:0/22:5(4Z, 7Z, 10Z, 13Z, 16Z)) | Down |
| | PE(24:0/22:5(4Z, 7Z, 10Z, 13Z, 16Z)) | Down |
| | PE(24:0/22:4(7Z, 10Z, 13Z, 16Z)) | Down |
| | PE(20:0/24:1(15Z)) | Down |
| | PE(20:4(8Z, 11Z, 14Z, 17Z)/20:0) | Down |
| | PE(18:0/22:4(7Z, 10Z, 13Z, 16Z)) | Down |
| | PE 40:4 | Down |
| | PE 38:4 | Down |
| Glycosphingolipid | Lactosylceramide (d18:1/24:1(15Z)) | Down |
| | Lactosylceramide (d18:1/16:0) | Down |
| | Glucosylceramide (d18:1/24:1(15Z)) | Down |
| | Glucosylceramide (d18:1/24:0) | Down |
| | Glucosylceramide (d18:1/22:0) | Down |
| | Glucosylceramide (d18:1/20:0) | Down |
| | Glucosylceramide (d18:1/18:0) | Down |
| | Trihexosylceramide (d18:1/16:0) | Down |
| | 3-O-Sulfogalactosylceramide (d18:1/22:0) | Down |

Figure 20:
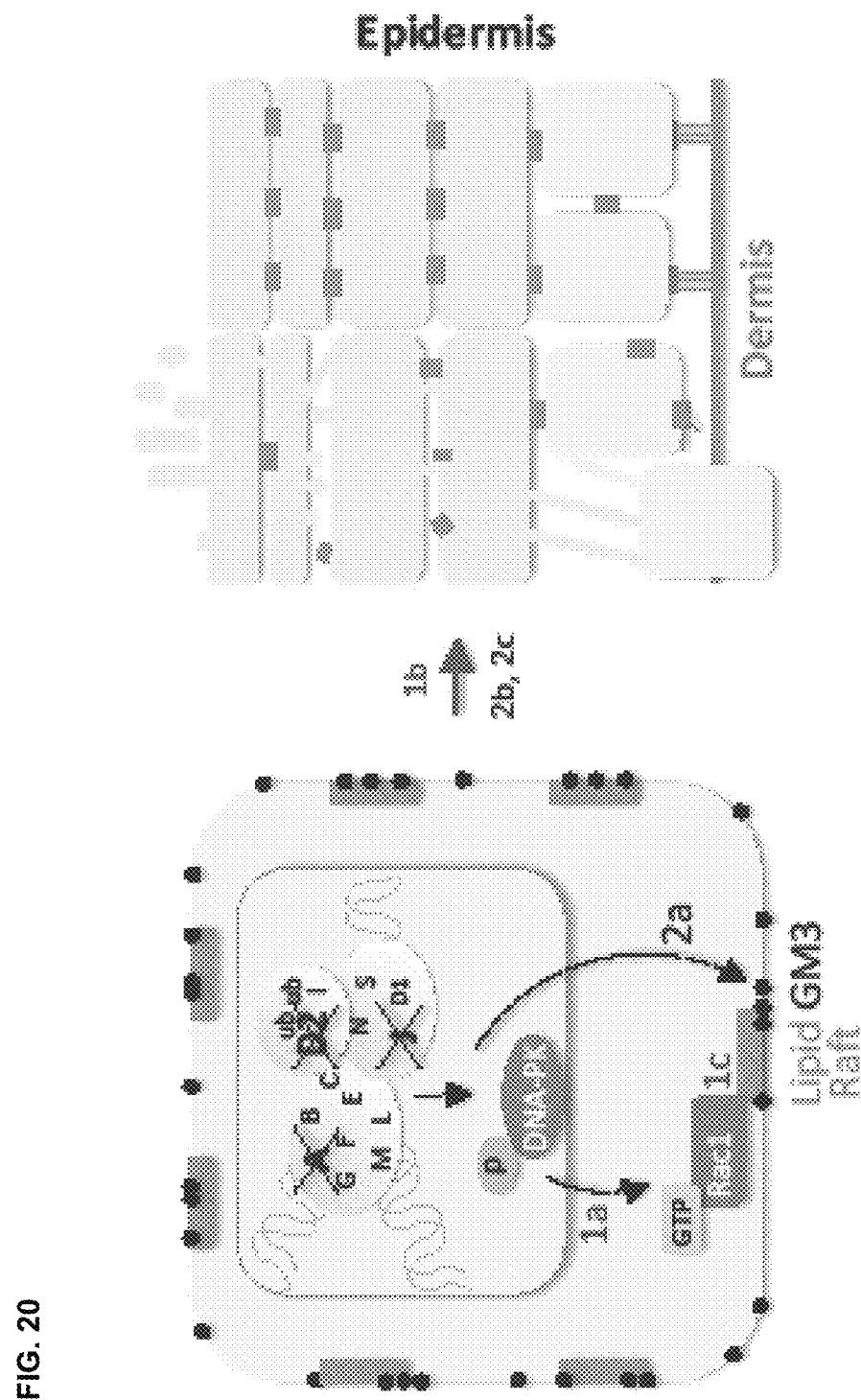
FIG. 20 shows a working hypothesis that loss of FA pathway function stimulates DNA-PK/Rac1 signaling and ganglioside biosynthesis. These connected or parallel pathways may occur in association with lipid rafts to impair epidermal structure and function.

The data indicated a unique small metabolite signature associates with FA, supported by
- NIKS: +/− knockdown
- UM-SCC1: +/− knockdown
- FA patient derived immortalized keratinocytes: +/− complementation
- FA patient derived SCC: +/− complementation
- FA patients v control cohorts FA loss de-regulated essential membrane-associated lipids and caused altered membrane morphology, supported by
- NIKS: +/− knockdown
- UM-SCC1: +/− knockdown (EM)
- FA patient derived immortalized keratinocytes: +/− complementation (EM)
- FA patient derived SCC: +/− complementation (EM)
- FA patients v control cohorts
- FANCD2 knockout mice The FA pathway has a role in keratinocyte biology and is intensely studied for its role in the repair of DNA interstrand crosslinks in all cells. DNA interstrand crosslink repair is initiated by recruitment of the FA core complex and central machinery, and downstream engagement of breast cancer susceptibility proteins such as FANCJ (FIG. 20). Germline loss-of-function mutations in any one of the 17 FA genes cause FA. Patients are diagnosed with FA based on crosslinker sensitivity, and often exhibit skeletal abnormalities and progressive bone marrow failure. Nearly all FA patients develop squamous cell carcinoma, particularly of the head and neck (HNSCC), with dismal survival. In addition to these inherited defects, mutations in FA genes are common in sporadic HNSCCs. The cells of origin for both inherited and sporadic HNSCCs are keratinocytes, which comprise 90% of the squamous epithelium of skin and mucosa. The close association between the FA pathway and HNSCC points to a critical role for the FA pathway in keratinocyte biology, but the molecular nature of that association is unclear. Studies investigating FA pathway function in normal keratinocytes are nearly absent.

The consequences of FA pathway loss were used to investigate FA pathway function. FA-deficient normal keratinocytes exhibited structural abnormalities in the cellular cytoskeleton and plasma membrane, and functional abnormalities in stimulated motility. These phenotypes were more pronounced in transformed keratinocytes. Normal skin from FA patients harbored novel ultrastructural defects in cellular adhesion and organization. The molecular consequences of FA pathway deficiencies to be equally significant. Specifically, FANCJ loss in HNSCC cells activated the DNA-damage sensor kinase DNA-PK and the small GTPase Rac1, and both proved to be required for invasion. We hypothesized that the FA pathway regulates keratinocyte structure or function at least in part through DNA-PK/Rac1 signaling.

Rac1 signaling occurs in close association with lipid rafts (LRs), membrane micro-domains with critical roles in cell signaling and motility. Interestingly, activated DNA-PK can also localize to LRs in the context of DNA damage. Unbiased and targeted mass spectrometry analyses identified an FA-pathway-specific lipid signature in both normal and transformed keratinocytes. The most notable element of this signature was consistent elevation of GM3, a key ganglioside in LRs. Inhibiting GM3 production in FANCJ-deficient HNSCC models reversed cellular invasion. It was thus hypothesized that ganglioside accumulation in response to FA loss de-regulates LRs structurally or functionally, to sustain Rac1 signaling and cellular invasion. Together, the data suggested that the FA pathway regulates DNA-PK-Rac1-dependent signal transduction and GM3 accumulation to maintain epidermal homeostasis. To test this, newly identified molecular connections between FA pathway loss, DNA-PK/Rac1 activation and ganglioside metabolism in normal and transformed epidermal models isogenic are being investigated for FA components. The outcomes will be used to test candidate therapeutic targets. These studies include the use of novel clinical specimens, and represent an important step towards a long-term goal of diagnosing, preventing, and reversing SCC susceptibility in patients with acquired and inherited FA pathway deficiencies.

FA signaling pathway and its function in human keratinocytes and 3D epidermis. In keratinocytes, loss of the FA pathway stimulates reversible cytoskeletal aberrations and motility through DNA-PK/Rac1-dependent signaling. Normal and pathological human epidermal systems are utilized that have either been FA depleted or corrected.

The regulation and sequence of DNA-PK/Rac1 signaling, by quantifying their activity and co-dependence in FA are being defined.

The role of DNA-PK and Rac1 is being determined in aggressive invasion, by genetic or chemical manipulation.

The localization and mechanism of Rac1 activation in FA-deficient cells is being determined using biochemical fractionation and functional testing of guanine nucleotide exchange factors.

Mechanism determination of ganglioside accumulation, and blocking GM3 production for targeting of FA pathologies. The FA pathway maintains epidermal homeostasis through control of GM3 biosynthesis. Quantification and manipulation of GM3 in FA-proficient and -deficient keratinocytes and 3D epidermis isogenic for FA is performed.

The identification of enzyme mediators of FA-dependent ganglioside regulation, by performing isotope tracing experiments coupled with mass spectrometry.

The determination whether FA-pathway-dependent control of GM3 regulates keratinocyte adhesion and motility, and targeting GM3 therapeutically, alone or in combination with DNA-PK/Rac1.

Corrolation of FA skin pathologies, ganglioside levels and barrier function, by quantifying each in skin specimens from FA patients.

FA is a genome instability syndrome with unique susceptibility to squamous cell carcinomas. Early diagnostic features include short stature, skeletal abnormalities, and hyper- and hypo-pigmentation of the skin and oral cavity (1-4). FA is a recessive disorder resulting from mutation in one of 17 FA genes that participate in DNA repair specialized in the resolution of interstrand crosslinks. As a result, patients exhibit cellular and organismal sensitivity to crosslinkers (5-7). FA is best known for causing acute myelogenous leukemia; individuals with the disease also possess a strong predisposition to development of HNSCCs—keratinocyte-based, squamous cell carcinomas of the head and neck (primarily in the oral cavity), as well as of the esophagus and anogenital region (8-11). The role of HPV infection in the FA patient population remains controversial ref. In the general population, HNSCC tumors are either HPV+ or HPV. The presence of HPV confers improved outcome. HPV, the most prevalent sexually transmitted virus, is best known for its association with cervical cancer (12) and is the etiologic cause of approximately 25% of HNSCCs (13). Over the past ten years, the inventors studied FA in collaboration with the FA Comprehensive Care Center that provides continuous care for children with genome instability syndromes, including over 150 with FA. An IRB-approved FA-tissue repository permitted the inventors to accrue, culture, and retrovirally correct a multitude of specimens utilized for these studies. Building on clinical collaborations, new epidermal functions of the FA pathway are being investigated.

The FA pathway suppresses keratinocyte growth and motility and sustains epidermal integrity. Several groups reported that epidermal FA loss stimulates proliferation. For example, in murine models, Fancd2 loss increased basal-cell proliferation in E7-negative control mice. The combination of genetic loss of Fancd2 and transgenic HPV16 E7 expression targeted to basal epithelial cells led to development of HNSCC (14). The inventors demonstrated that FA pathway loss stimulates cell proliferation and hyperplasia in differentiated human epidermis expressing high-risk HPV oncogenes, and FA pathway correction rescues the normal phenotype (15). HPV− FA-patient-derived HNSCC cell lines harbored stem-cell populations that were either similar in number or increased, compared to sporadic HNSCC lines (experimental end points were tumor sphere formation, CD44 positivity or ALDH1 status) (16-17).

In addition to these published studies of proliferation, data including EM studies of normal skin specimens from FA patients, and studies of 3D cutaneous and oral organotypic keratinocytes and epithelial rafts isogenic for FA, demonstrated novel cytoskeletal and membrane aberrations, and intercellular adhesion defects. FA-deficient keratinocytes also displayed increased motility compared to their FA-proficient controls. These preliminary data suggested that the FA pathway maintained epidermal homeostasis, and that disruption of the pathway predisposed to and/or promoted SCC development.

FA gene products are key coordinators of DNA crosslink repair. The protein products of eight of the seventeen FA genes, including FANCA, assemble at the site of genome damage, forming the "FA core complex." The upstream complex triggers monoubiquitination of two central pathway members FANCD2 and FANCI (18-22). The activated FANCD2/FANCI dimer then orchestrates recruitment of downstream repair proteins, including the breast-cancer susceptibility proteins BRCA1/FANCS, BRCA2/FANCD2, and BRIP/FANCJ.23 (FIG. 20). FA-deficient cells exhibit reduced capacity for DNA repair by homologous recombination (HR). Data from several FA models suggest that crosslinker sensitivity in FA is also a consequence of inappropriate choice of non-homologous end joining (NHEJ) (10, 24-28). The inventors demonstrated FA loss activated the DNA sensor kinase DNA-PK in HNSCC cells, and uncovered novel roles for DNA-PK, unrelated to DNA repair, in promoting Rac1 activation and cytoskeletal aberrations. It is unclear whether DNA-PK/Rac1 signaling is activated in models of non-transformed FA epidermis.

HNSCC is a devastating tumor with limited therapeutic options. HNSCC is the sixth leading type of cancer worldwide, with an incidence of 500,000 (29). While HNSCCs in FA patients are usually diagnosed early in life (and at advanced tumor stages), HNSCCs in the general population arise later in life (30-31). Over one half of all HNSCC cases are diagnosed at a locally advanced or metastatic stage, and approximately 50% of treated patients relapse with local or distant metastasis, both bearing poor remission rates. Decades of research have not improved HNSCC outcomes significantly, and the classic therapeutic option, a combination of surgery, radiation and chemotherapy, leaves patients permanently disfigured. Thus, there is a need to improve understanding of the biological processes driving local invasiveness, and develop novel approaches for tumor prevention, early diagnosis and new therapies for the treatment of late stage tumors (32).

FA gene mutation and transcriptional repression are common in sporadic HNSCCs. The invetnors' recent analyses of exome sequencing data and whole genome sequencing data demonstrated that 11% of HPV− HNSCCs and 18% of HPV+ HNSCCs harbor non-synonymous mutations in FA pathway components (33-34). In addition to classical loss-of-function mutations, transcriptional down regulation of FANCB, FANCC, FANCF, FANCJ, and FANCM (e.g, through promoter methylation) has been noted in dysplastic head and neck tissue and HNSCC (35-36). The inventors' analyses of The Cancer Genome Atlas (TCGA) data for HNSCC revealed that 25% of tumors harbor transcriptional up-regulation, gene amplification and/or mutation in the DNA-PK gene PRKDC. In contrast, FA or PRKDC mutations are rarely observed in acute myeloid leukemia. These findings indicate potential tissue specific relevance for FA/DNA-PK activities in human epidermis and/or HNSCC.

Small GTPase signal transduction and ganglioside metabolism are associated with membrane lipid rafts. Rac1 is a well known regulator of the cellular actin cytoskeleton, adhesion, polarity, barrier function and migration. Like other members of the Rho family, Rac1 molecules cycle between GDP-bound inactive, and GTP-bound active states (37). These GTPases are controlled by two classes of regulatory molecules: guanine nucleotide exchange factors (GEFs) which activate Rac/Rho functions, and GTPase-activating proteins (GAPs) which repress Rac/Rho functions. In addition to enzymatic activities, GEFs and GAPs harbor protein-protein and lipid binding domains that target them to distinct subcellular locations. Rac1 associates with membranes, and of those, primarily with cholesterol-rich, ordered domains referred to as lipid rafts (38-39). Recent studies have refined this view by showing that Rac1 initially translocates to LR domain boundaries, and is then partitioned into raft domains where it is active, and into non-raft domains where it is largely inactive (40).

Glycosphingolipids and sterols are enriched in lipid rafts (LRs), structurally unique regions of the plasma membrane that regulate cytoskeletal scaffolding, polarity, adhesion, and signaling. Through a combination of unbiased and targeted metabolomics in FA knockdown versus control keratinocytes and HNSCC cells, the invetnors found that glycosphingolipid metabolism was significantly upregulated. Specifically, GM3 (NeuACα2-3Galβ1-4Glcβ1-1ceramide), a monosialodihexosyl-ganglioside, and downstream gangliosides were significantly up-regulated in FA-deficient keratinocytes. Inhibition of GM3 accumulation blocked HNSCC invasion driven by FA loss. These data establish new connections between the FA pathway and ganglioside metabolism in normal and transformed squamous cells, and implicate GM3 in advanced tumor phenotypes that result from the loss of FA. Interrogating the function of ganglioside metabolism downstream from FA pathway loss and probing possible links to Rac1 and DNA-PK signaling at LRs are being performed. New connections between DNA repair machineries and membrane biology are expected in normal and transformed settings.

The inventors are mechanistically defining the role of signaling and lipidomic pathways that respond to FA pathway loss by de-regulating cytoskeletal and membrane biology. Results could radically change the view of biomarkers, causes, and cures for SCC susceptibility, and explore fundamental cell-autonomous mechanisms whereby DNA damage response pathways control the integrity of human epidermis.

These studies are conceptually and technically innovative in several aspects. FA is an accepted disease model for DNA repair deficiency; somatic loss of the FA pathway and DNA-PK up-regulation in HNSCC appear to be common events. All preliminary data are unpublished, human model systems comprise oral and cutaneous keratinocytes, 2D and 3D models, and FA specimens and cohorts. Human models are a specific focus because FA knockout mice do not spontaneously develop SCC or other clinical hallmarks of FA. Preliminary experiments uncover defects in the integrity and organization of FA skin for the first time; these are possible SCC susceptibility factors. Regulation of DNA-PK/Rac1 signaling, ganglioside metabolism, membrane integrity and motility by the FA pathway has not yet been reported. Results may apply to other genome instability pathologies wherein DNA-PK is activated. The information will set the stage for the discovery of biomarkers and for the targeting of signaling and lipid pathways in FA-related diseases. Mass spectrometry based metabolomics and isotope tracer studies are an innovative addition to this effort. Local and distal HNSCC invasiveness is a key determinant of poor outcome. Fundamental knowledge about the acquisition of invasive characteristics in response to FA loss and/or DNA-PK activation may result in new treatments for the same phenotypes which are responsible for the majority of cancer-related deaths.

Figure 21:
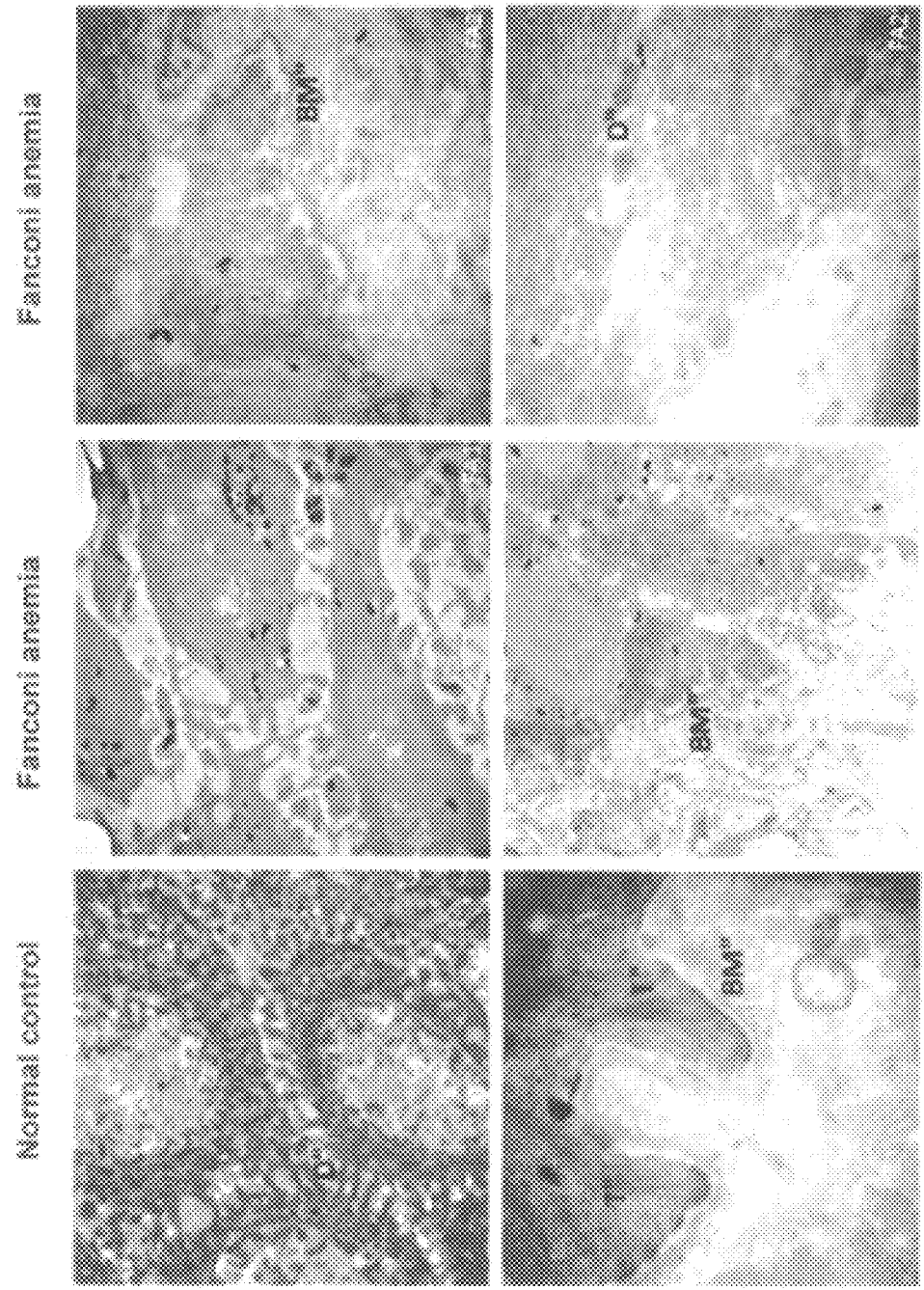
FIG. 21 shows electron microscopy (EM) of normal skin from a control and individuals with FA. Normal skin punch biopsies were obtained from 1 control individual and 2 individuals diagnosed with FA, fixed, and processed as described. Ultrathin sections (100 nm) were cut using a Reichert-Jung Ultracut E microtome and counterstained in 2% aqueous uranyl acetate and Reynolds lead citrate. Images were taken with a transmission electron microscope (Hitachi H-6750) equipped with a digital camera (AMT 2k×2K tem CCD). BC: basal cells. BM: basement membrane; T: tonofilaments; D: desmosomes.

Defining the role of FA pathway loss and downstream signaling in normal and transformed keratinocytes. FA pathway loss causes defects in normal epidermis. Over the past six years, the inventors have followed a study cohort of FA patients. Controls are unaffected siblings and parents, as well as age and gender matched healthy populations. From surveys of 71 adult participants with FA, nine reported a history of skin cancer (13%). Of these, seven reported SCC, and two reported both SCC and basal cell carcinoma. Only two patients reported ever having undergone a bone marrow transplant (22%). Skin biopsies from five patients with FA were evaluated by EM and compared to normal control skin (FIG. 21). Pathology evaluation determined that FA skin showed a basal lamina that was generally intact, with a few areas of duplication. The lamina lucida, however, was very nonuniform in width with multiple expanded areas, in contrast to the normal skin which showed a uniform space between the basal lamina and the overlying basilar epithelial cell. Although hemidesmosomes (HDs) could be identified in the FA patients, they were generally poorly developed and appeared as short structures, which were not well related to the underlying basal lamina. Tonofilaments were clearly evident in the basal epithelial cell; however, they appeared to be disorganized and frequently arranged in irregular clumps with random orientation and no relationship to the underlying HDs. In contrast, the normal skin biopsy showed tight bundles of tonofilaments that were highly organized and arranged uniformly in a perpendicular orientation to the HD attachment points. In the normal skin in the upper layers of the epidermis, the interface between two keratinocytes was highly uniform in appearance and contained numerous desmosomes arranged in an orderly pattern and uniformly spaced from each other. Projections of the keratinocyte along these interfaces were generally short and there were no irregular or widely spaced gaps between the cells. In contrast, cells from the upper layers in the FA epidermis showed highly variable gaps between adjacent cells and the cell projections were not arranged in a parallel fashion as seen in the normal skin. Desmosomes were present, but were not distributed in a uniform manner with multiple orientations.

Figure 22A:
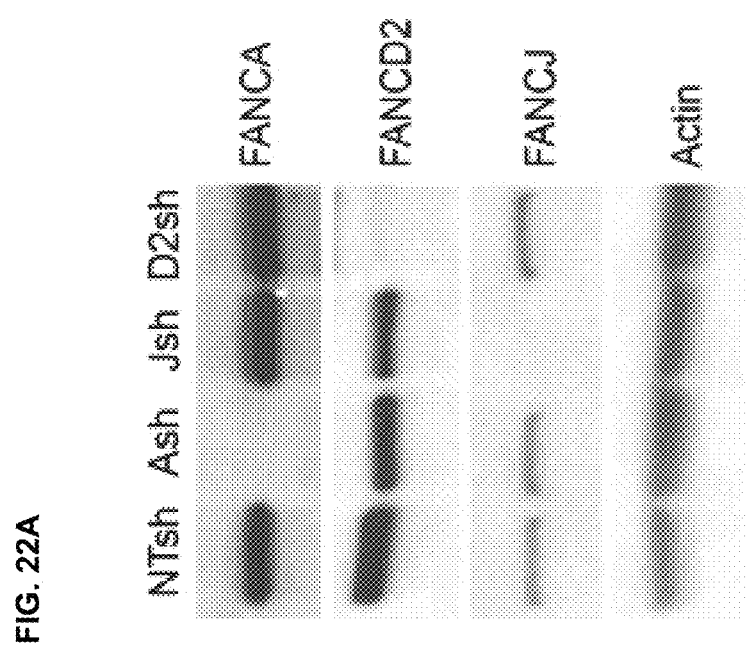
FIGS. 22A-F show FA-deficient SCC1 cells exhibit morphological and cytoskeletal aberrations.
Figure 22B:
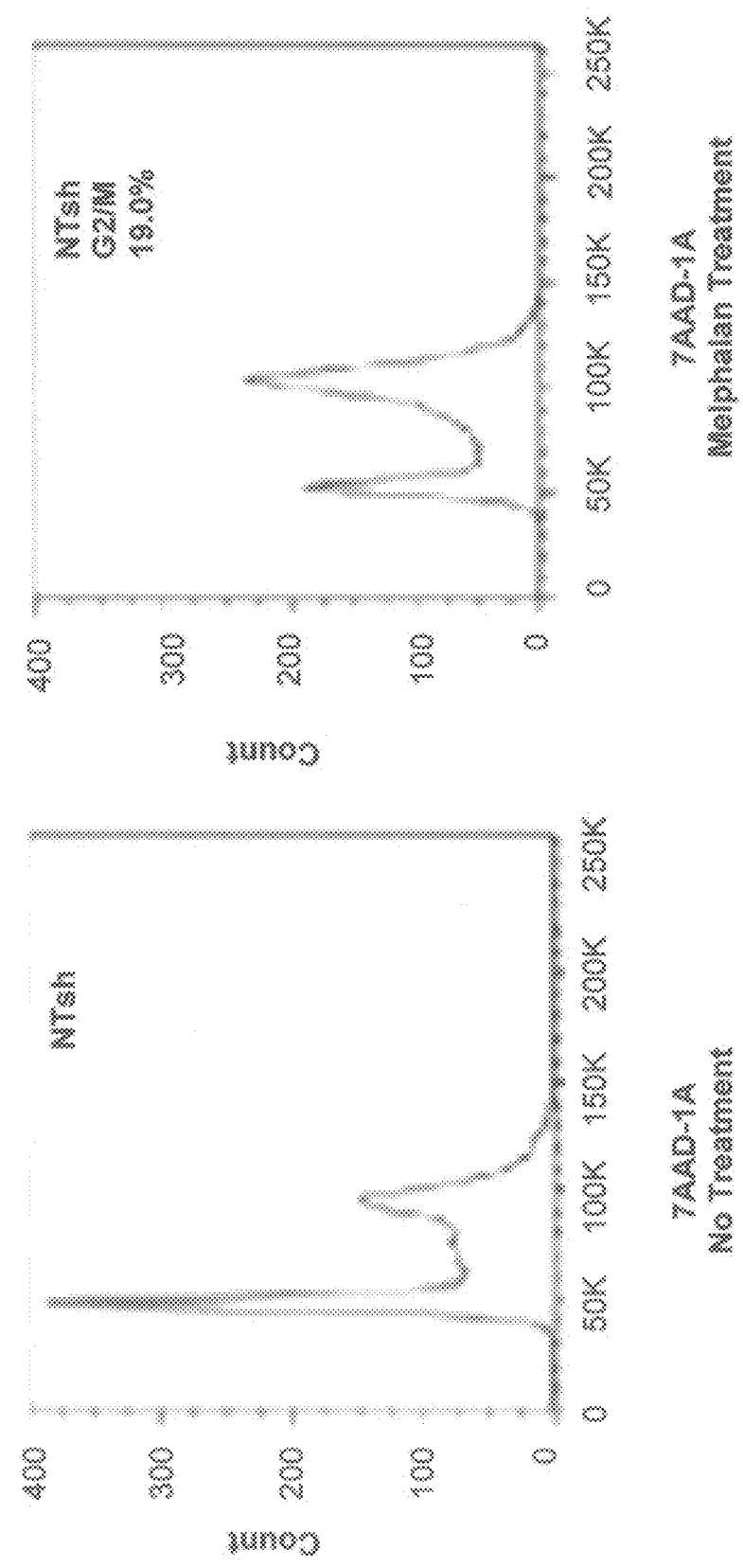
Figure 22B:
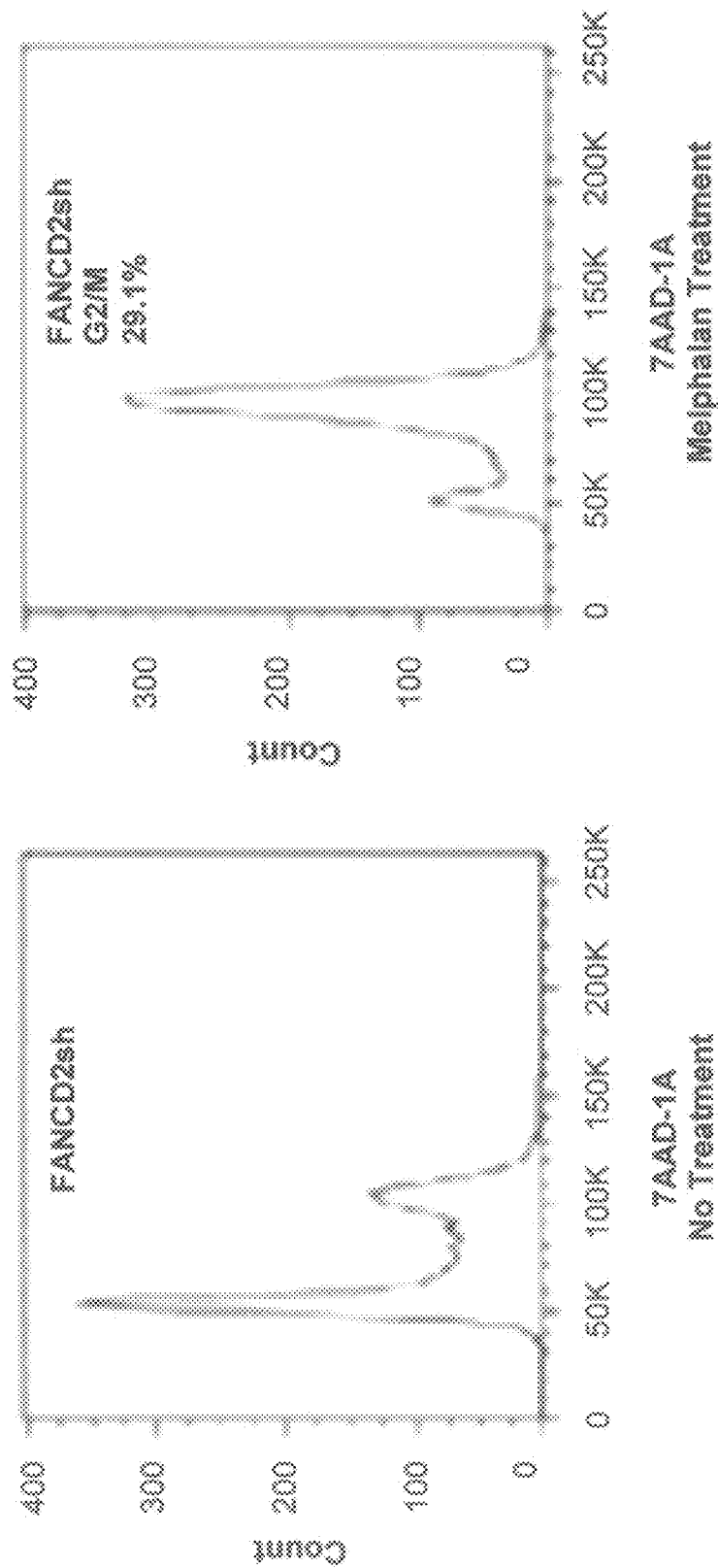

FA pathway loss leads to cytoskeletal and membrane aberrations in HNSCC cells. A significant proportion of sporadic HNSCCs harbor somatic mutations in FA and FA-related genes (33). To test for biological effects of FA pathway loss, knockdown models of HNSCC were created using published lentiviral shRNA vectors (15, 41). First, the HPV-negative (UM-)SCC1 cell line was knocked down for FANCA, FANCD2, and FANCJ. Western blot analyses verified specific and efficient FA protein depletion (FIG. 22A). To verify that FANCD2 depletion induced classical FA phenotypes, DNA crosslinker sensitivity was quantified. FANCD2-deficient SCC1 cells responded to melphalan treatment with an increased proportion of cells in G2/M, compared to cells treated with non-targeting sh (NTsh) vector (FIG. 22B). This was similar to FA lymphoblasts and fibroblasts that also respond to melphalan with G2/M cell-cycle arrest (42-43). FANCA- and FANCJ-deficient SCC1 cells responded similarly, as did UMSCC6 and UMSCC47 HNSCC cell lines depleted for FA proteins (data not shown). Thus, FA knockdown in HPV-positive and -negative SCC1 cells induced the classic FA DNA-crosslinker sensitivity phenotype.

Figure 22C:
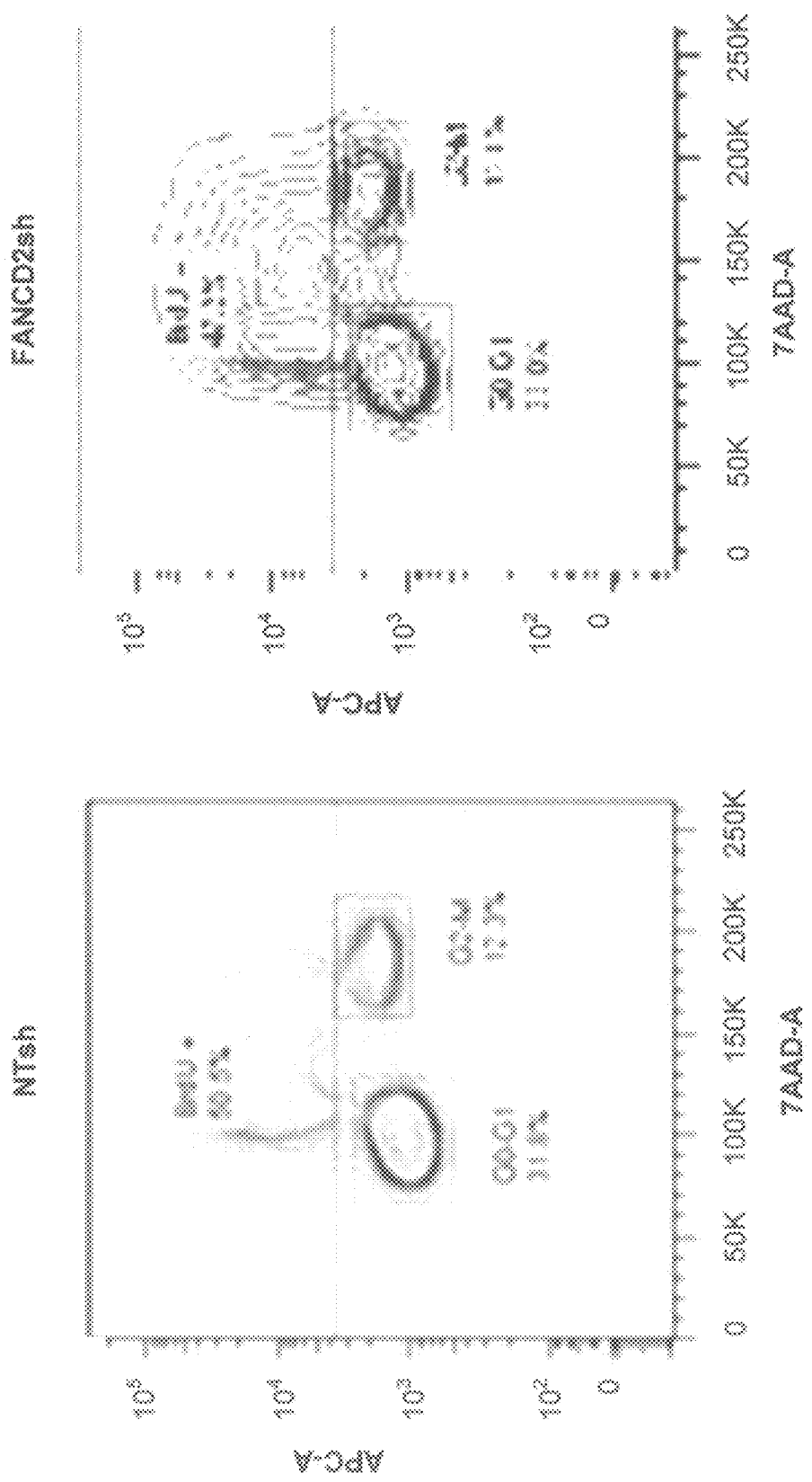
Figure 22D:
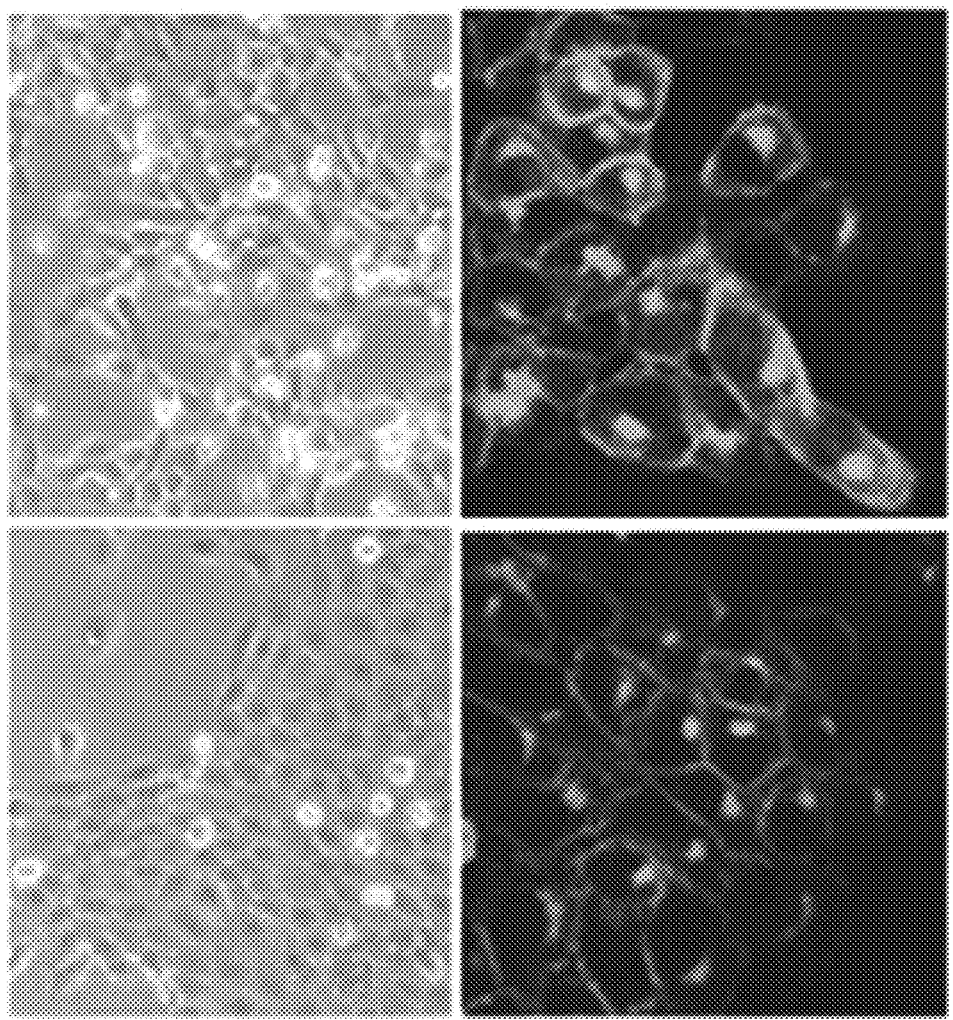
Figure 22E:
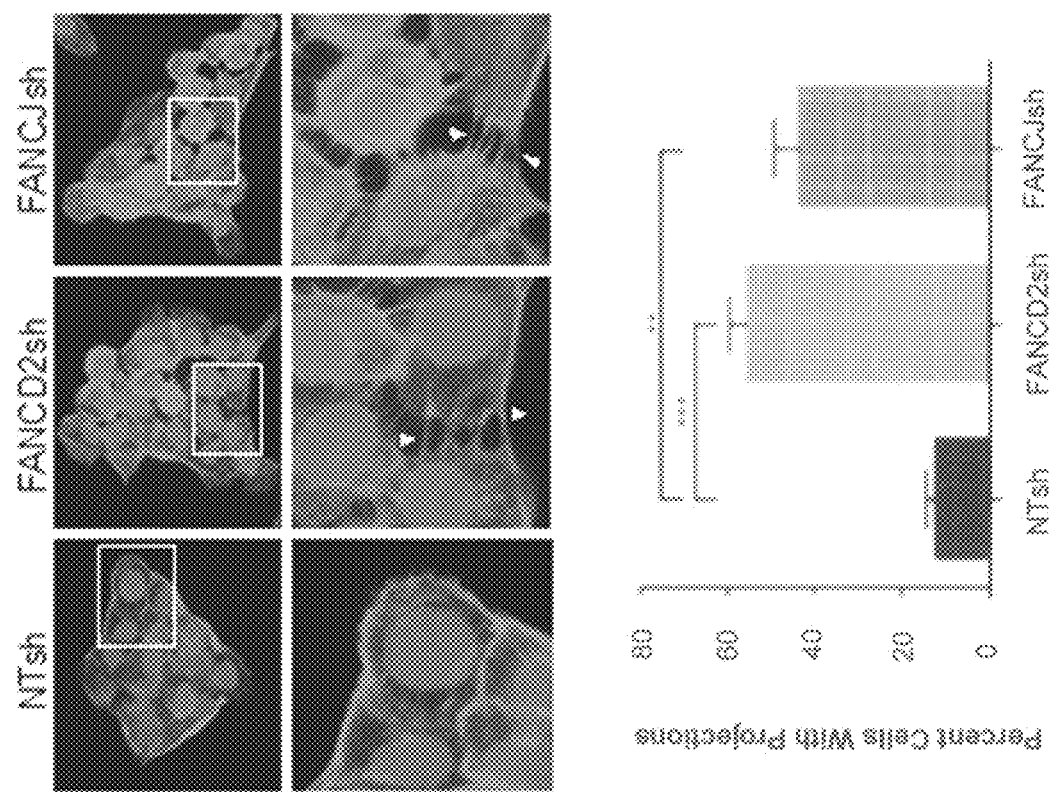
Figure 22F:
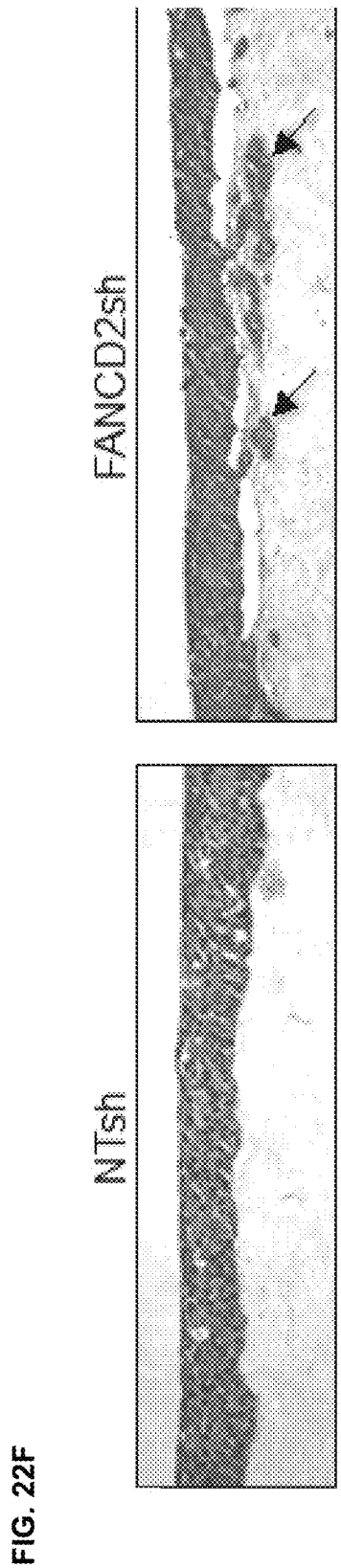

RNA sequencing of FA-knockdown versus control SCC1 cells revealed an absence of proliferative gene signatures in line with comparable proliferative rates in standard culture conditions (FIG. 22C, and (15)) and subsequent ToppGene ontology analysis (not shown). Morphological features of FA-depleted and control UM-SCC1 cells were examined. Clear differences in cell shape and spatial arrangement were noted under phase contrast, and particularly increased intercellular protrusions (FIG. 22D top). Use of filipin III as a probe for cholesterol-rich membrane micro-domains revealed a strong IF signal in FANCD2sh compared to NTsh cells (FIG. 22D bottom). Staining with the F-actin marker phalloidin further revealed that FA-depleted cells were connected by long intercellular projections. These projections were largely absent in control cultures which, instead, exhibited tight epithelial cell-cell contacts; these differences in intercellular connectivity were statistically significant (FIG. 22E). To assess the ability of FA-depleted cells to form 3-D tissues, organotypic epithelial tumor rafts from FANCD2sh-treated SCC1 cells were generated. While the FANCD2-deficient cells grew and assembled into 3D tissue, isolated cells were occasionally noted in the underlying collagen matrix, in contrast to the NTsh controls (FIG. 22F).

Loss of the FA pathway stimulates epidermal proliferation, as shown in FIG. 33. FIG. 33A shows normal oral keratinocytes (NOKS) and normal skin keratinocytes (NIKS) that were subjected to organotypic raft culture and sections stained by immunofluorescence (IF) for basal (K14) and differentiated (K10) cell markers. FIG. 34B shows Edu incorporation was carried out for IF detection of proliferating cells. Quantitation for both NOKS and NIKS is shown.

Figure 23A:
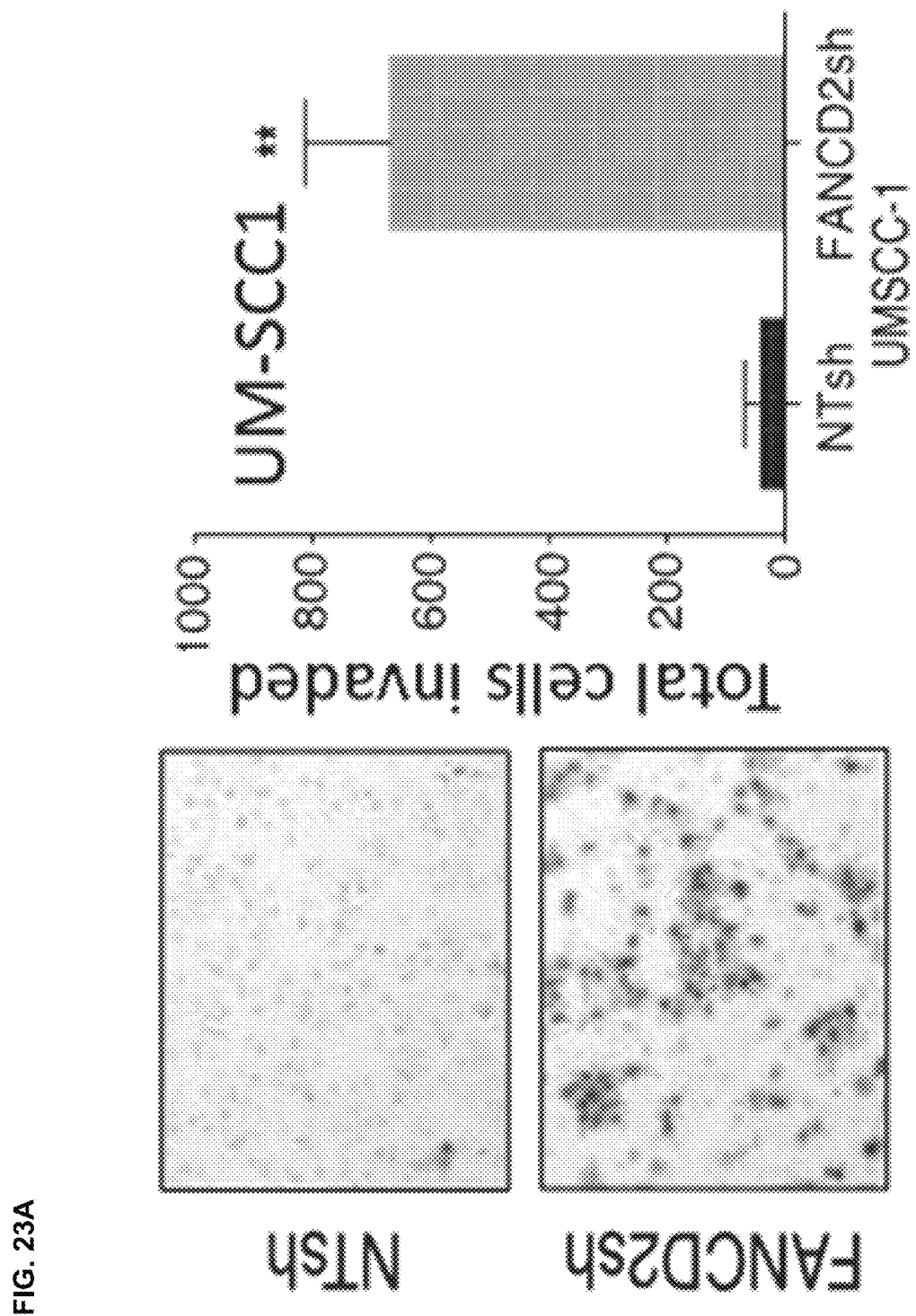
FIGS. 23A and B show a pathway loss promotes invasion of squamous tumor cells. Indicated cells were treated with the indicated shRNA vectors and then plated in Matrigel-coated transwells. After 22 hours, invasive cells were quantified.
Figure 23B:
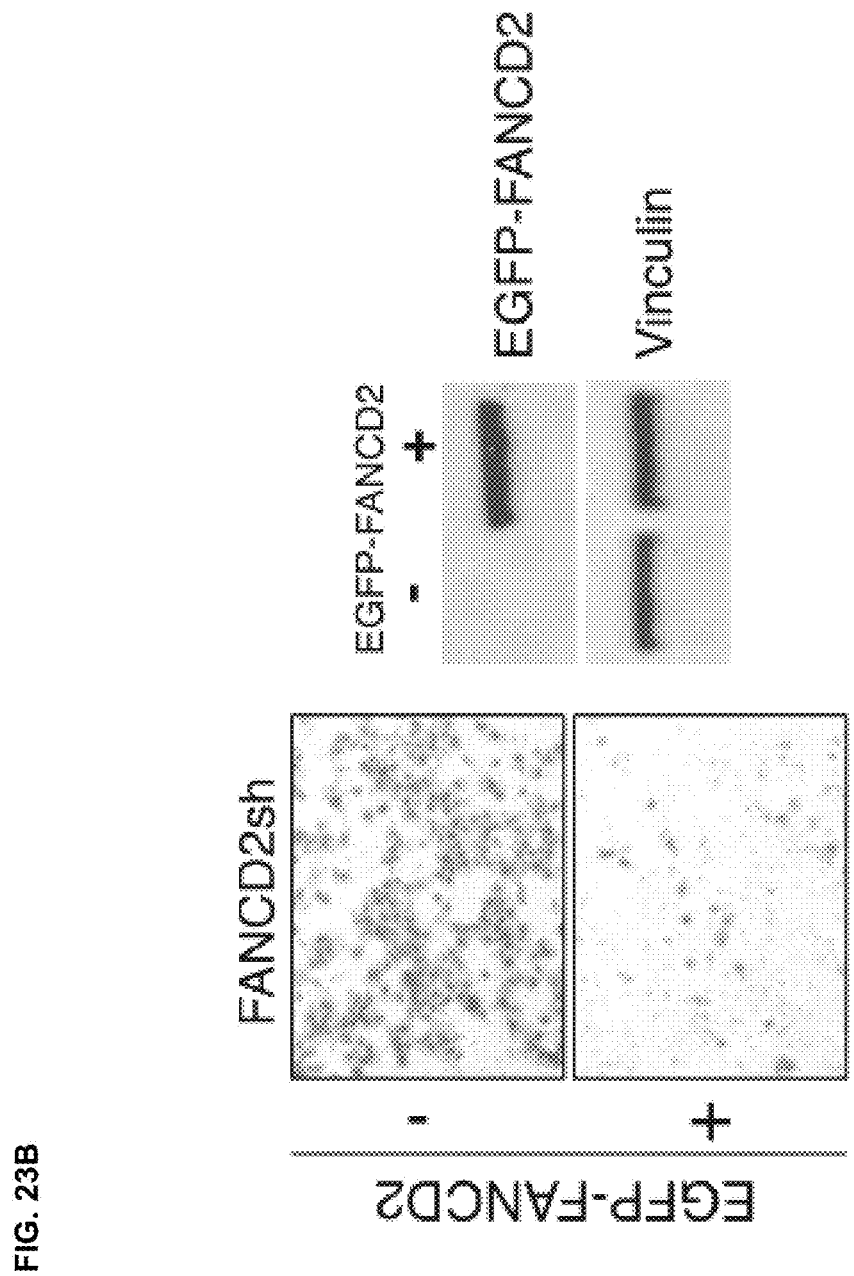
FIG. 23B shows SCC1 cells that were transduced with an EGFP-FANCD2 retroviral expression vector, sorted for GFP− (control) or GFP+ cells, and then processed for western-blot analysis or plated in Matrigel-coated transwells.
Figure 23C:
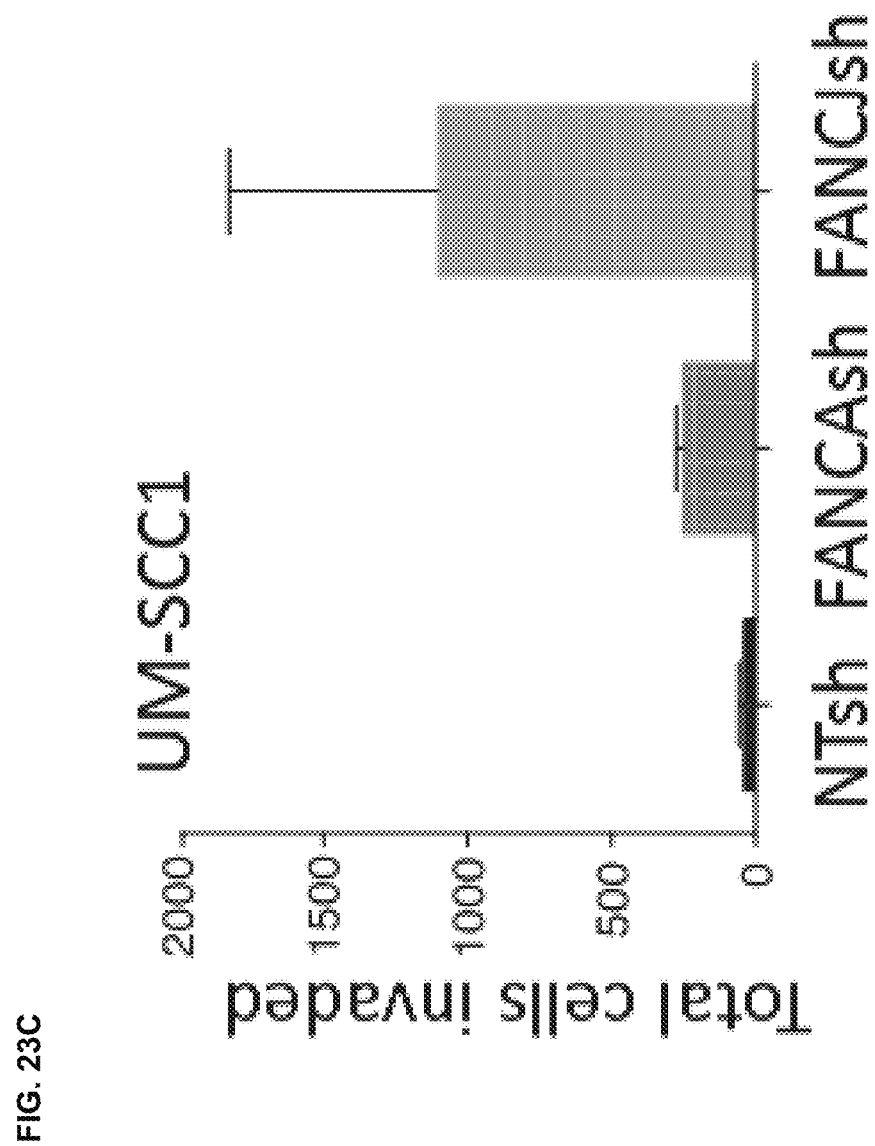
FIGS. 23C-E show SCC1, SCC6 and SCC47 cells, respectively.
Figure 23D:
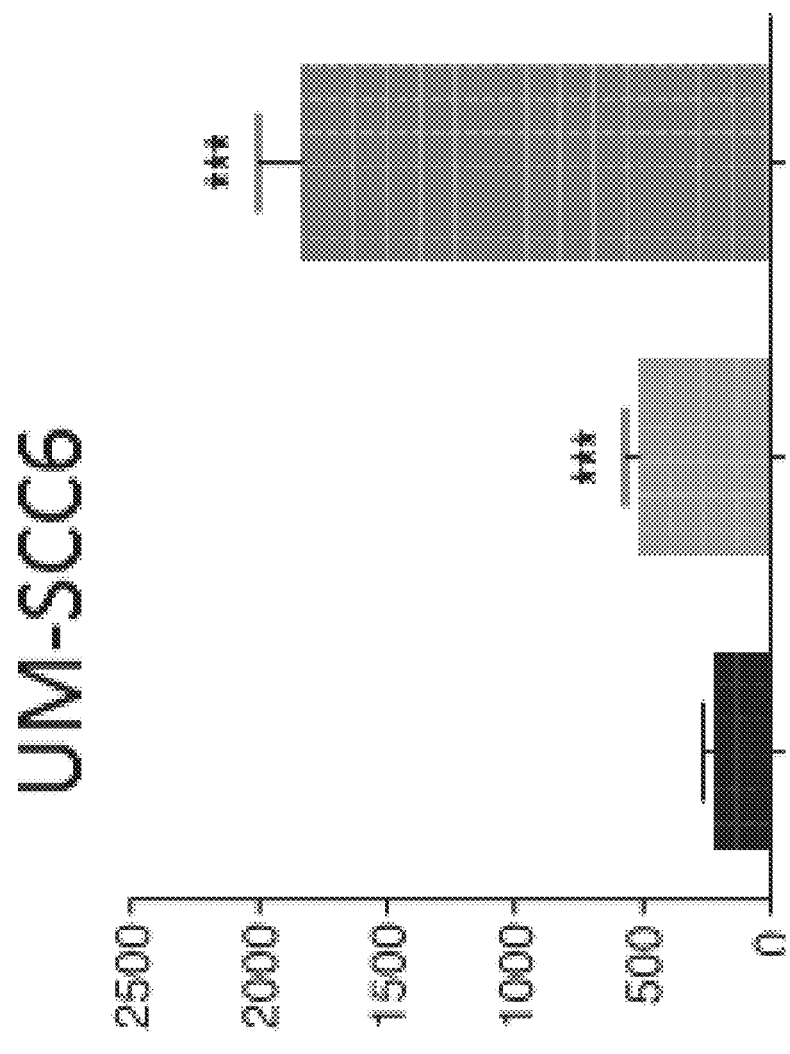
Figure 23E:
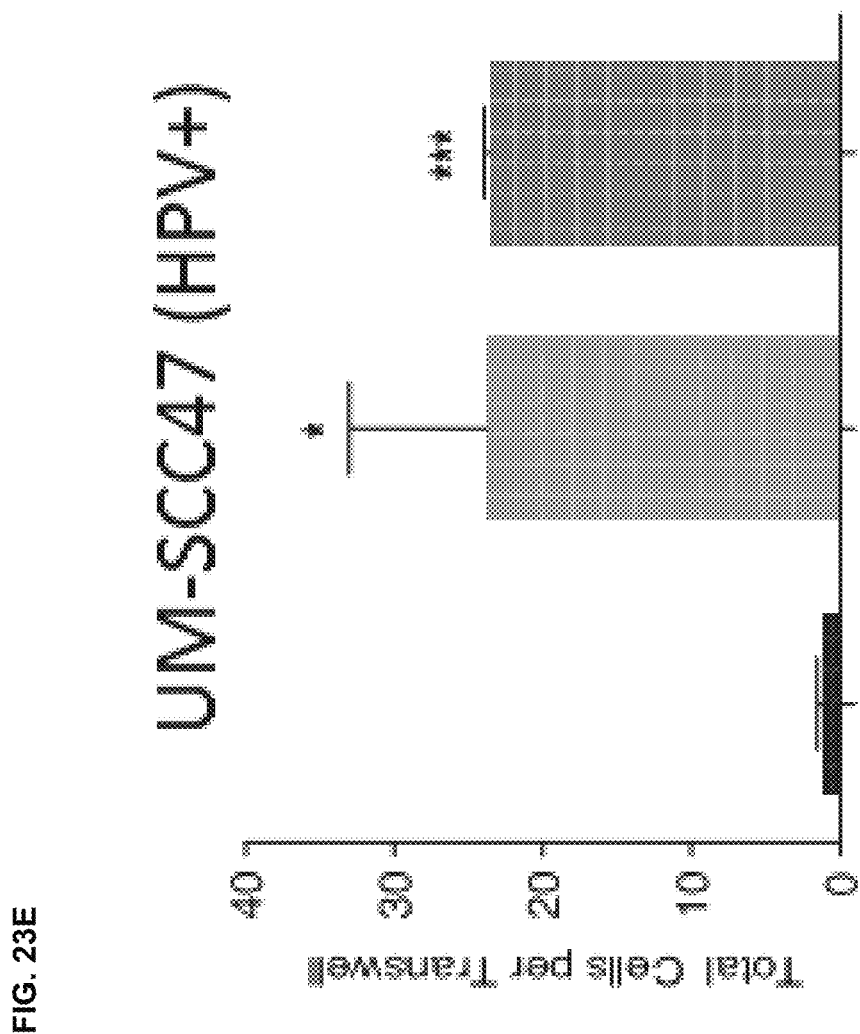

FA pathway loss promoted motility and invasion. To assess motility and invasiveness of FA-deficient cells, the Matrigel cell invasion assay was used. FANCD2sh-treated SCC1 cells were significantly more migratory (data not shown) and invasive (FIG. 23A), in the absence of proliferative gains (FIG. 22C). To rule out off-target effects of the lentivirus, an shRNA-resistant EGFP-FANCD2 construct was introduced. The EGFP-FANCD2 fusion protein was expressed in GFP+ cells (but not GFP− cells), and was sufficient to block invasion of FANCD2sh-treated SCC1 cells (FIG. 23B). Similarly, FANCA and FANCJ knockdown stimulated invasion in SCC1 cells (FIG. 23C). HPV− SCC6 and the HPV+ SCC47 cells exhibited increased invasion upon FANCA and FANCD2 loss (FIGS. 23D, E). Gains in cellular motility were also observed for normal oral keratinocytes (NOKS): 1.3% of NTsh normal oral keratinocytes (NOKS) cells plated were able to migrate through matrigel. This invasion frequency doubled upon FANCD2 knockdown, highlighting potential relevance for FA loss for the motility of normal cells (data not shown).

Figure 24A:
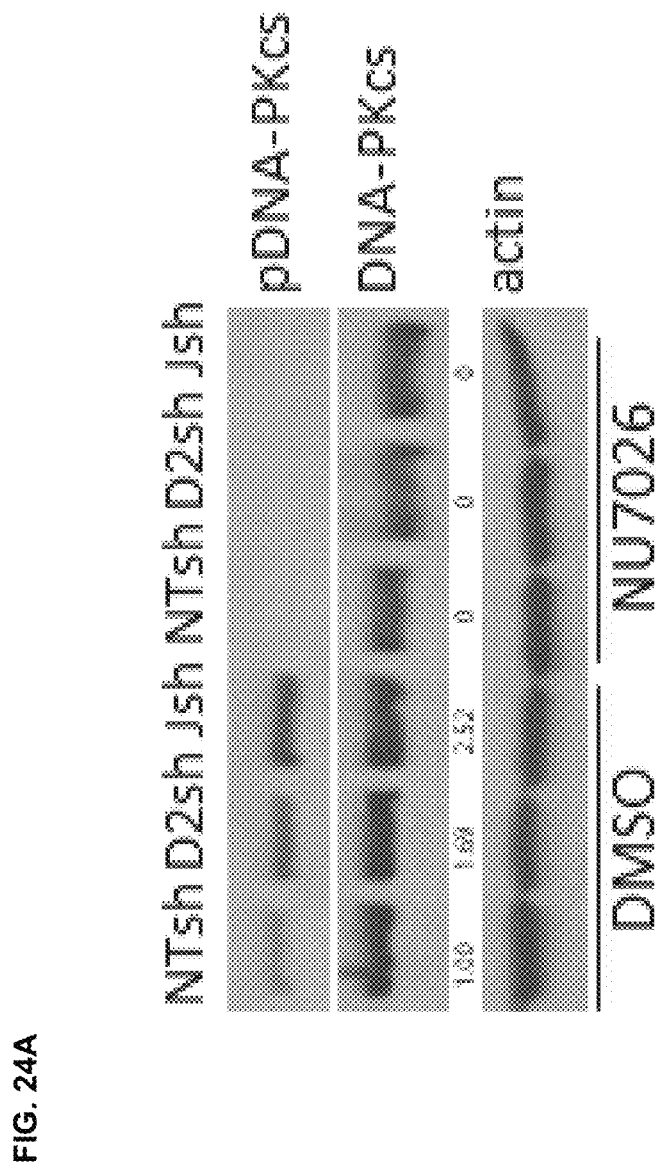
FIG. 24A to FIG. 24F show pDNA-PK/Rac1 signaling axis stimulates invasion in FA-deficient cells.
Figure 24B:
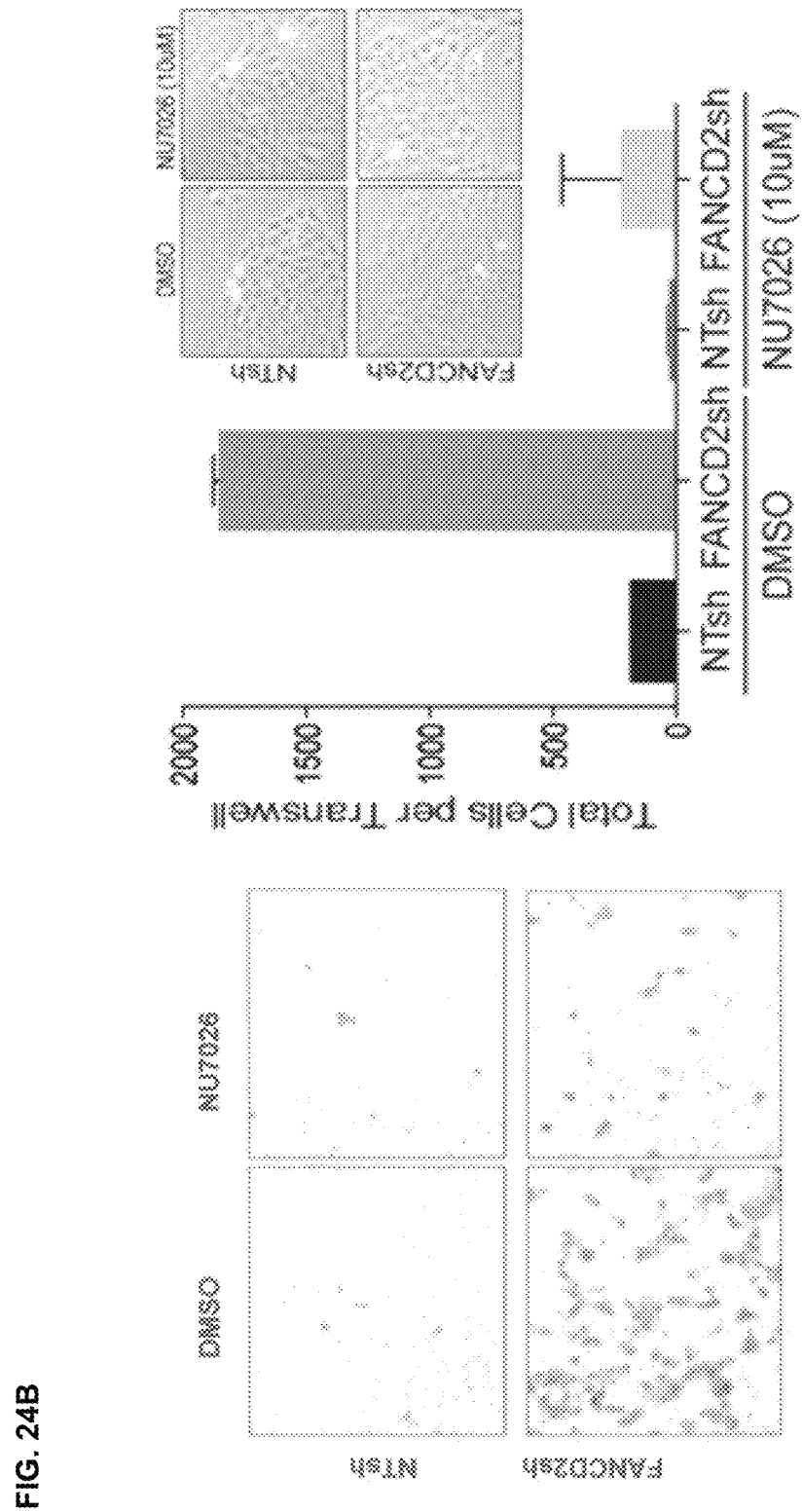

DNA-PK/Rac1 signaling occurred in response to FA pathway loss and was required for cytoskeletal re-organization and invasion. FA cells exhibit characteristic sensitivity to DNA crosslinkers, and defects in error-free DNA repair by HR. These defects are accompanied, under some circumstances, by a corresponding increase in the activity of error-prone non-homologous end joining (NHEJ) pathway components (27-28). Repair by NHEJ requires activation of the catalytic subunit of DNA-dependent protein kinase (DNA-PKcs) and subsequent autophosphorylation on serine 205645 (pDNA-PKcs). The inventors first determined whether DNA-PKcs signaling was activated and involved in FA-associated invasion. FANCD2sh- and FANCJsh-treatment of SCC1 cells stimulated pDNA-PKcs. The DNA-PK inhibitor NU7026 lead to undetectable pDNA-PKcs in the two FA-deficient cell populations, but also in the control cells (FIG. 24A). Further, NU7026 suppressed invasion, of FANCD2sh-treated SCC1 cells, but did not appear to affect growth (FIG. 24B). These data indicated that DNA-PK activity promoted SCC invasion in the presence or absence of a functional FA pathway. TCGA data mining revealed one quarter of HNSCCs harbor DNA-PK gene or message amplification (data not shown), and may thus be at risk of tumor progression through DNA-PK driven signaling pathways.

Figure 24C:
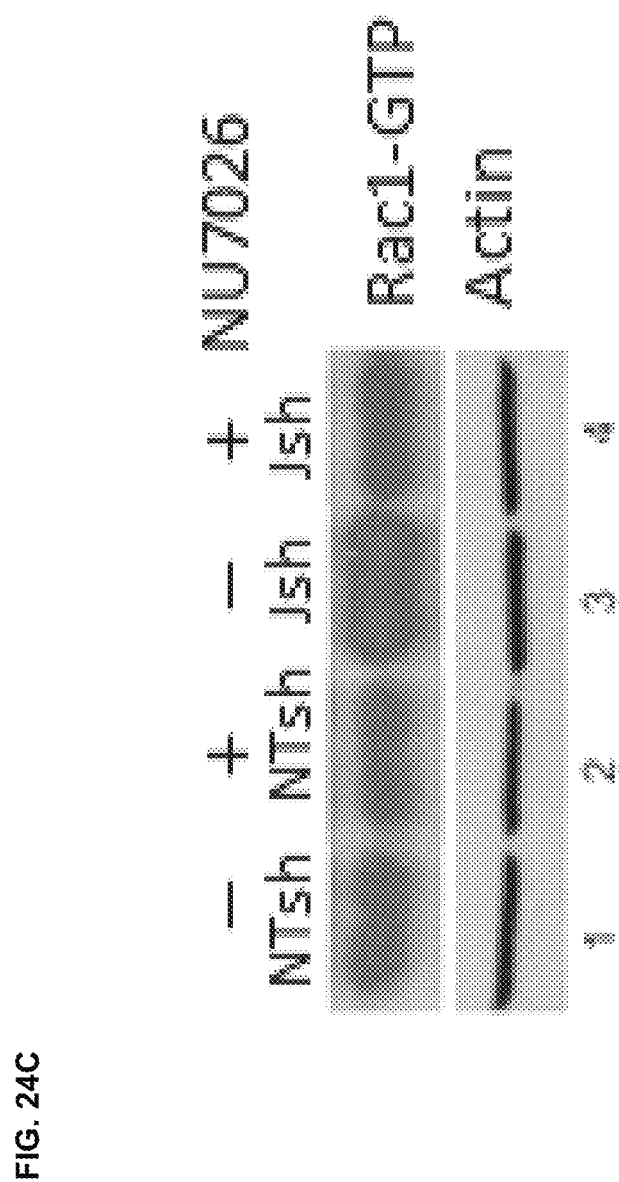
Figure 24D:
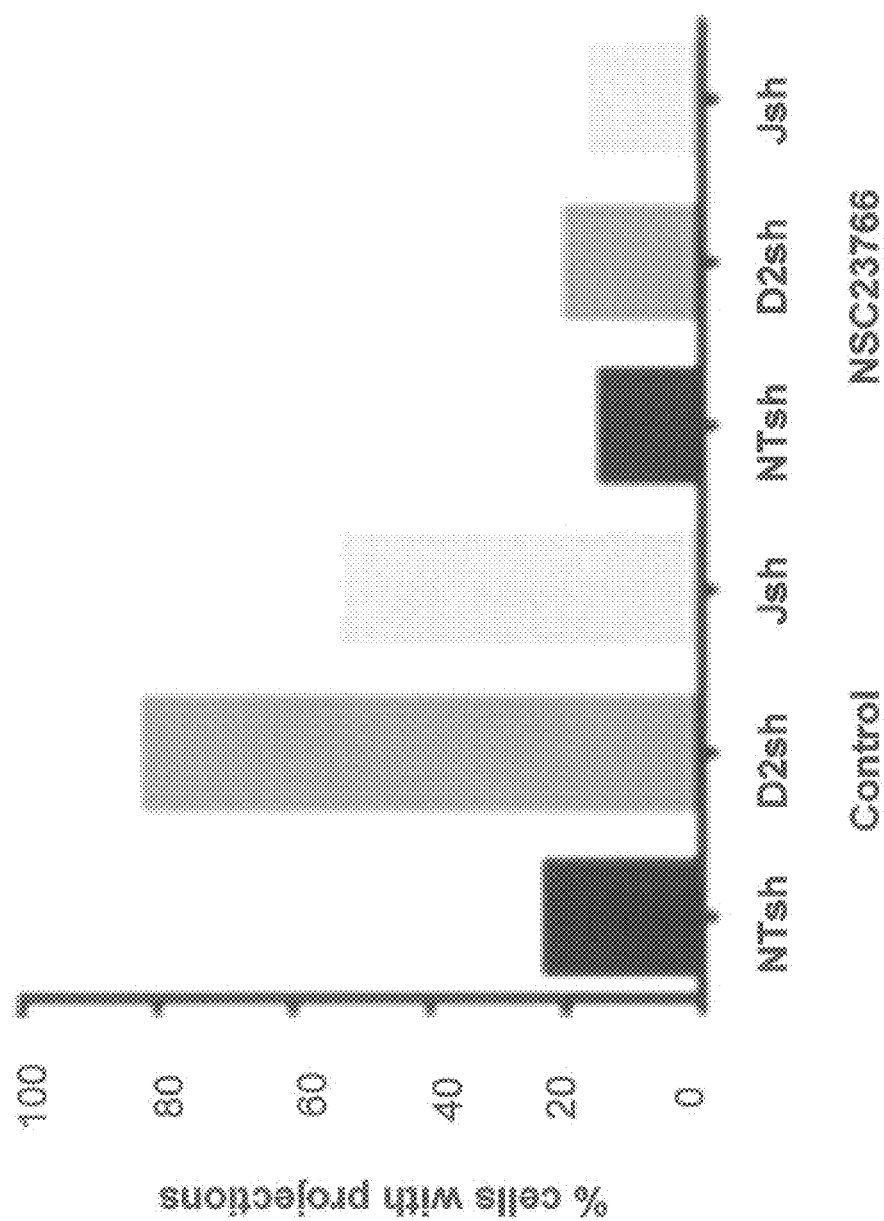
Figure 24E:
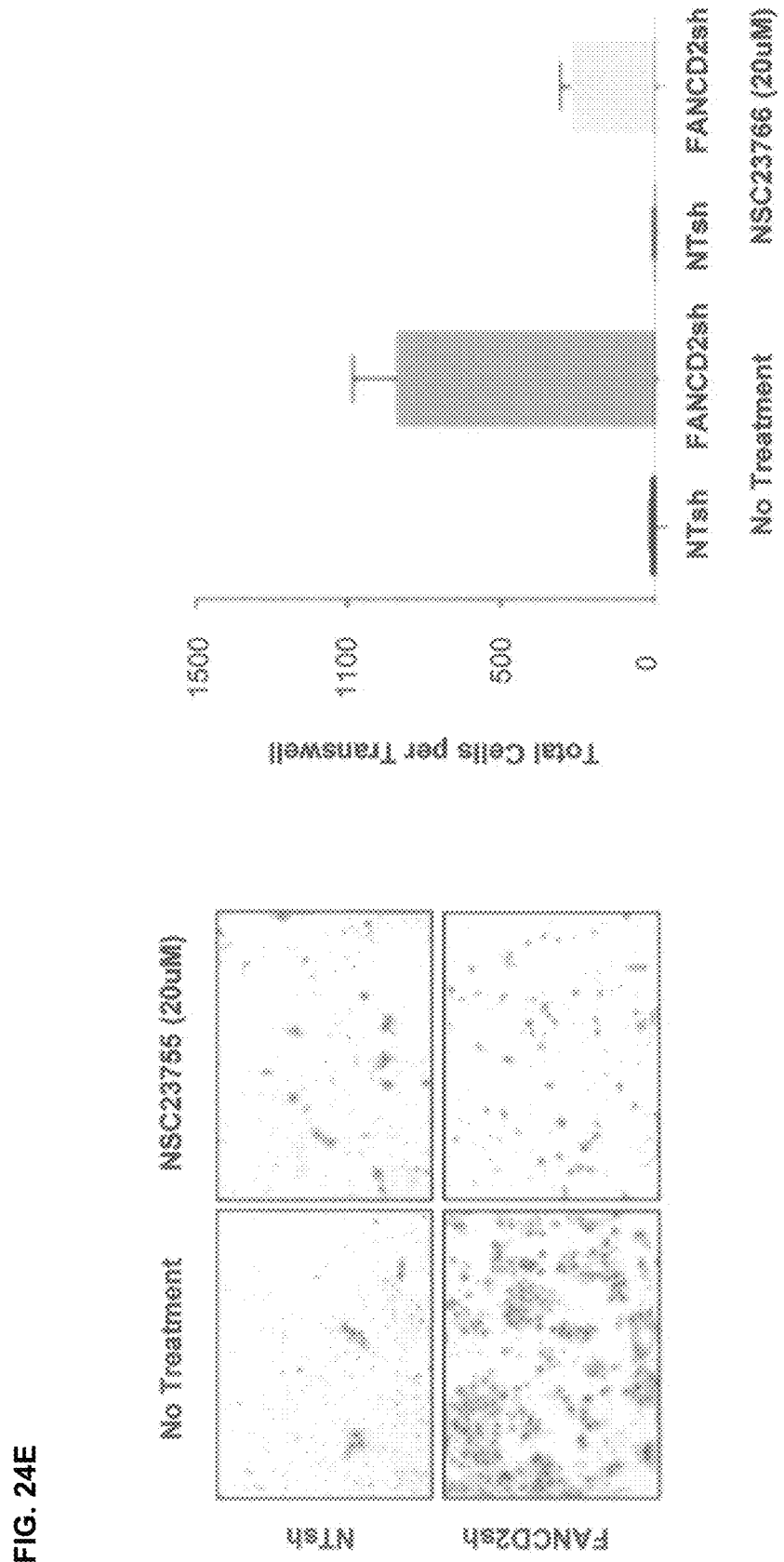
Figure 24F:
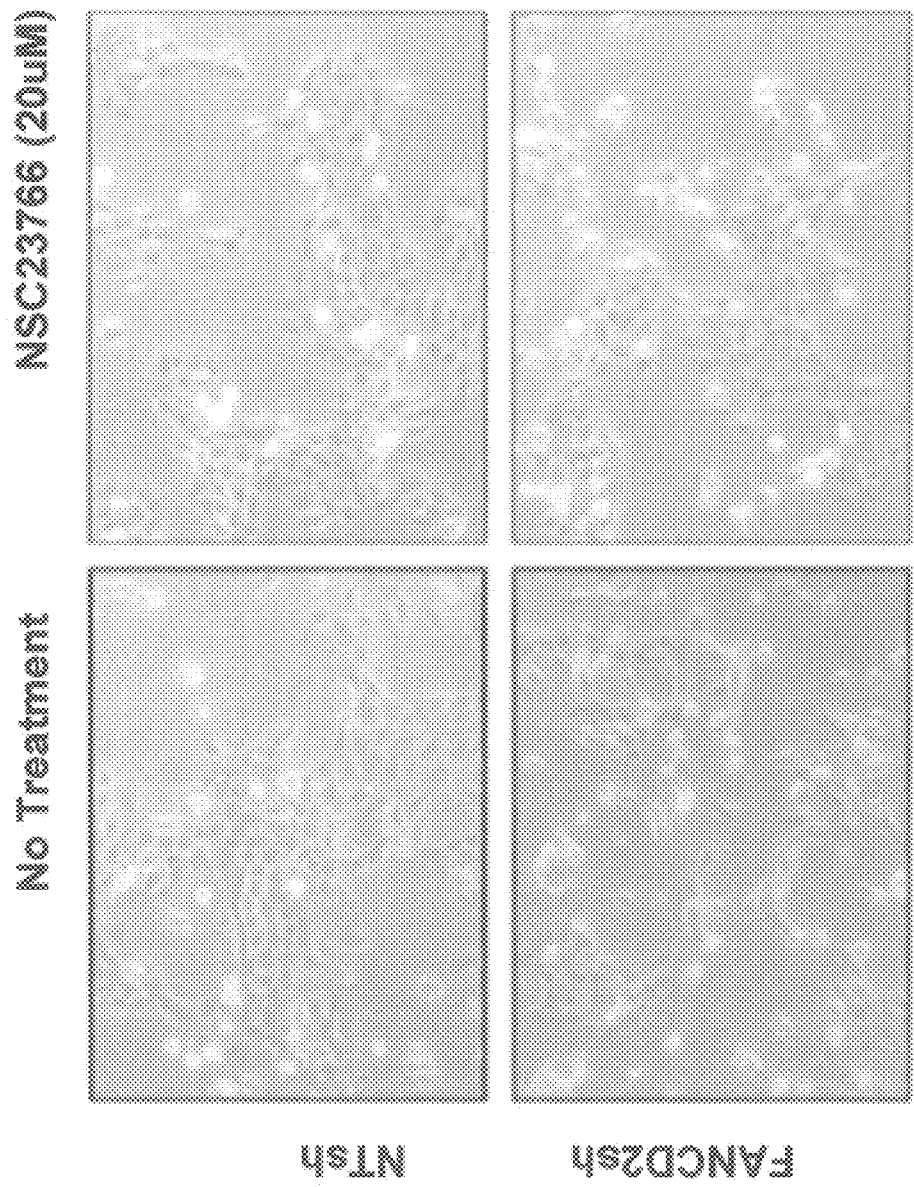

Members of the small GTPase Rho, Rac and CDC42 family of signaling molecules were key players in normal and transformed cell morphology, adhesion, motility, and invasion (46). These enzymes hydrolyze GTP and are active when GTP-bound, and inactive when GDP-bound. Because Rac1 activation is reported to produce intercellular projections (47-48) similar to the ones noted in FA-deficient cells (FIG. 22E), the inventors carried out Rac1-GTP pull-downs to determine whether Rac1 is activated by FA pathway loss; FANCJsh SCC1 cells were used, since pDNA-PK activation in these cells was robust (FIG. 24A). These cells exhibited elevated levels of active Rac1 (compared to NTsh controls) (FIG. 24C, compare lanes 1 and 3). Treatment with DNA-PKcs inhibitor significantly lowered active Rac1 in FA-deficient cells (compare lanes 3 and 4), but did not affect Rac1 activity in control cells (compare lanes 1 and 2). To examine the requirement for Rac1 in cytoskeletal re-organization and invasion of FA-deficient cells, the specific Rac1 small molecule inhibitor NSC23766 was used (49-50). NSC23766 reduced the number of long intercellular projections in both FANCD2sh- and FANCJsh SCC1 cells (FIG. 24D). NSC23766 also suppressed cell invasion, but not growth, of FANCD2sh SCC1 cells, but did affect invasion of control cells (FIG. 24E). This Rac1 inhibitor did not appear to affect growth of FANCD2sh SCC1 cells (FIG. 24F). Thus, FA pathway loss leads to downstream activation of pDNA-PK and Rac1, and both are required for cytoskeletal rearrangements and invasion. The studies build on established expertise and available reagents summarized in the tables below.

Summary of Laboratory Methods

Assays described were either published by the inventors' laboratory, or are shown in the figures.

| METHOD | PUBLICATION (Wells) |
| --- | --- |
| FA gene knockdown | Hoskins 2009; Hoskins 2012 |
| FA gene complementation | Hoskins 2009; Lombardi 2015 |
| Organotypic raft culture | Hoskins 2012 |
| Time lapse microscopy | Morrison, 2010 |
| Cellular adhesion | Morrison, 2010 |
| Transwell migration & motility | Vinnedge, 2011 |
| Xenographs | Wise 2009, Vinnedge, 2014 |
| In vivo proliferation and death | Adams, 2014; Vinnedge, 2014 |
| Rac1 modulation and activity | |
| Metabolic tracing | |
| Electron microscopy | |
| Epidermal differentiation | Hoskins, 2012 |
| MS metabolomics | |
| GFA patient cohort | Sauter, 2014; Myers, 2013 |
| FA skin collection | Hoskins, 2009 |

Define the FA signaling pathway and its function in human keratinocytes and 3D epidermis using knock down and complementation. In keratinocytes, loss of the FA pathway stimulates reversible cytoskeletal aberrations and motility through DNA-PK-Rac1-dependent signaling. The studies build on established expertise and available reagents summarized in the tables.

Data indicate that FA pathway loss leads to epidermal de-regulation in several systems. In the skin of FA patients, defects were noted in organization and attachment of basal cells and basement membrane, and between cells (FIG. 21). In HNSCC cells, cytoskeletal rearrangements, intercellular membrane filaments (FIG. 22D-F) and increased invasion (FIG. 23) were noted. In FANCJ-depleted HNSCC cells, the increased invasion required activated DNA-PK kinase and Rac1 GTPase (FIG. 24). These findings suggested that FA pathway loss disrupted epidermal homeostasis by unknown mechanisms, and stimulated aggressive tumor phenotypes through a novel DNA-PK/Rac1 signaling axis. What remains unclear is whether DNA-PK/Rac1 signaling is reversible, and also active in normal keratinocytes (eg, NIKS or NOKS cells) where it may be connected to impaired FA epidermal defects. The DNA-PK/Rac1 signaling sequence has not been tested in other systems, and mechanism(s) of Rac1 activation in FA are unknown. To determine how nuclear FA loss translates into cytoskeletal aberrations and increased motility, the localization of DNA-PK/Rac1 and mechanism of Rac1 activation are being elucidated. The keratinocyte model systems are shown in the table below.

Human Cell Line- and Tissue-Based Model Systems

Cell lines will either undergo stable lentiviral knockdown of FA-pathway genes, or retroviral complementation as reported (51). HNSCC, head and neck squamous cell carcinoma; NIKS, Near-diploid Immortalized Keratinocytes derived from skin (52); NOKs, normal oral keratinocytes (53); NT, non-targeting; S91IN, retroviral complementation vector. Cutaneous keratinocytes: NIKS; Human skin and surface cells; Oral keratinocytes: NOKS; Sporadic HNSCC with stable lentiviral FA knockdown; FA patient derived HNSCC with stable retroviral correction.

| CELLS AND TISSUES | FA MODIFICATION | CONTROLS | MODELS OF: |
| --- | --- | --- | --- |
| (1) NOKS | FANCAsh, D2sh, Jsh | NTsh | FA loss in normal oral keratinocytes |
| (2) HNSCC lines SCC1 SCC47 SCC6 SCC22b | FANCAsh, D2sh, Jsh | NTsh | Somatic FA loss in HNSCC |
| (3) HNSCC lines VU1131 VU1365 OHSU974 | FA patient derived S91IN S91IN S91IN | FA corrected: S91IN-FANCC S91IN-FANCA S91IN-FANCA | Germline FA loss in HNSCC |
| (4) NIKS | FANCAsh, D2sh, Jsh | NTsh | FA loss in normal cutaneous keratinocytes |

| CELLS AND TISSUES | FA MODIFICATION | CONTROLS | MODELS OF: |
|---|---|---|---|
| (5) FA Skin specimen | Mutations in:<br>FANCA<br>FANCB<br>FANCC<br>FANCJ<br>unknown | Healty siblings and matched control populations | FA mutant skin |

Definition of the regulation and sequence of DNA-PK/Rac1 signaling, by quantifying their activity and co-dependence in FA. Quantify DNA-PK/Rac1 activation upon FA loss and correction. Isogenic lysates are prepared from four cells lines, NOKS, SCC1, SCC47 (+/− FA knockdown), and VU1131 (+/− FA correction). Knockdown of FANCD2 are prioritized initially, based on its central role in the FA pathway. Results are verified by FANCA and FANCJ knockdown. DNA-PK activity is assessed by autophosphorylation on S2056, T2609 and T3950 (51-52). Cell lysates are analyzed by Western blot for total and phosphorylated DNA-PK protein (as in FIG. 24A); a short pulse of bleomycin or mitomycin D may be required to visualize DNA-PK activity. DNA-PK nuclear focus formation will be quantified as an indirect measure of activity. To detect active GTP-Rac1, cell lysates will be harvested, normalized for equivalent protein concentrations, and then affinity purified with Rac1-specific Pak1 protein binding domain fused to GST as a bait (as in FIG. 24C); unfractionated lysates will be included for detection of active and total Rac1. Lysates of cells treated with GTPγS for Rac1 activation and GDP for Rac1 inactivation will be included as positive and negative controls. Pull-downs will be included for other members of the Rho GTPase family (i.e., cdc42 and RhoA) (50). If none of these members are activated by FA pathway deficiencies, these data will demonstrate the specificity of Rac1. On the other hand, if one or more of these Rho GTPases are activated, they will be studied in parallel with Rac1.

It will be verified that DNA-PK regulates and is upstream of Rac1. Cells will be cultured and DNA-PK activity inhibited using chemical DNA-PK inhibitors, knockdown, or dominant-negative T3950D mutant DNA-PK protein (52-53) followed by Rac1-GTP pulldown. To test specificity for DNA-PK, inhibitors of the ATM and ATR DNA-damage sensor kinases will be included, since there is activating and competing crosstalk between these three kinases.

A broad and central role for Rac1 in FA-dependent cytoskeletal de-regulation will be verified. Normal and transformed cells +/− FA will be cultured and Rac1 activity/signaling decreased using stable knockdown: selective chemical inhibitor NSC23766 (as shown in FIG. 24D), or expression of a dominant-negative Rac1 mutant (N17-Rac1), a wild-type Rac1 inhibitor (RhoGDI1), or an inactive D185R mutant (40). To test specificity, a panel of chemical and dominant-negative inhibitors of other Rho family members will be employed. Rac1 activity will be detected using established biochemical and immunohistochemical methods (54). Cells will be immunostained with DAPI to visualize nuclei, phalloidin and filipin to visualize cytoskeletal organization and cell protrusions and filopodia, and Rac1-GTP and Rac1 antibodies to detect active and total Rac1, respectively. Image J will be utilized for image acquisition. Inhibitors will be carefully titrated and utilized at concentrations that do not induce cell-growth arrest or death. Data will be analyzed using ANOVA or Student's t test.

The role of DNA-PK and Rac1 in cytoskeletal and motility phenotypes will be determined by genetic or chemical manipulation. It will be determined whether FA-pathway-dependent phenotypes require an active DNA-PK/Rac1 signaling axis. Test whether activation of DNA-PK and/or Rac1 is sufficient to stimulate invasion of FA-pathway proficient cells. HNSCC cells and NOKS will be treated in one of four ways: 1 and 2) DNA-PK or Rac1 activity will be inhibited, as described constitutively active and wildtype DNA-PK or Rac1 mutant proteins will be stably overexpressed in FA-pathway-proficient cells, using retroviral constructs (e.g., wild type and constitutively active T3950A DNA-PK,52 and the fast-cycling L61 and G12V mutant Rac1 proteins) (40).

In vitro time-lapse (motility) assay. Cultured cell lines will be time-lapse imaged with a Zeiss LSM510 confocal system attached to a Zeiss Axiovert 200 microscope with a heated stage. Six image fields (containing 10-20 cells each) will be acquired per condition per cell type every five minutes. For each cell, the position at each time point and maximum migration distance will be plotted relative to the starting position (55).

In vitro wound-healing (motility) assay. Confluent cultures will be scratched with a pipet tip across the cultures. Using the Zeiss LSM510 confocal system mentioned above, images will be captured every five minutes for at least twelve hours with LSM software and MultiTime macro. Cell edges for at least twenty cells in a single field of view are tracked using ImageJ software with the MTrackJ plug-in. Average distance and/or velocity of each cell will be determined (56).

In vitro transwell (motility and invasion) assay. NOKS cells (NTsh, FANCD2sh and FANCJsh) will be plated into transwells and monitored for migration and invasion through matrigel, respectively (57). Parallel flow cytometry for BrdU incorporation and caspase-3 cleavage will control for indirect effects of cell proliferation and survival.

Figure 25:
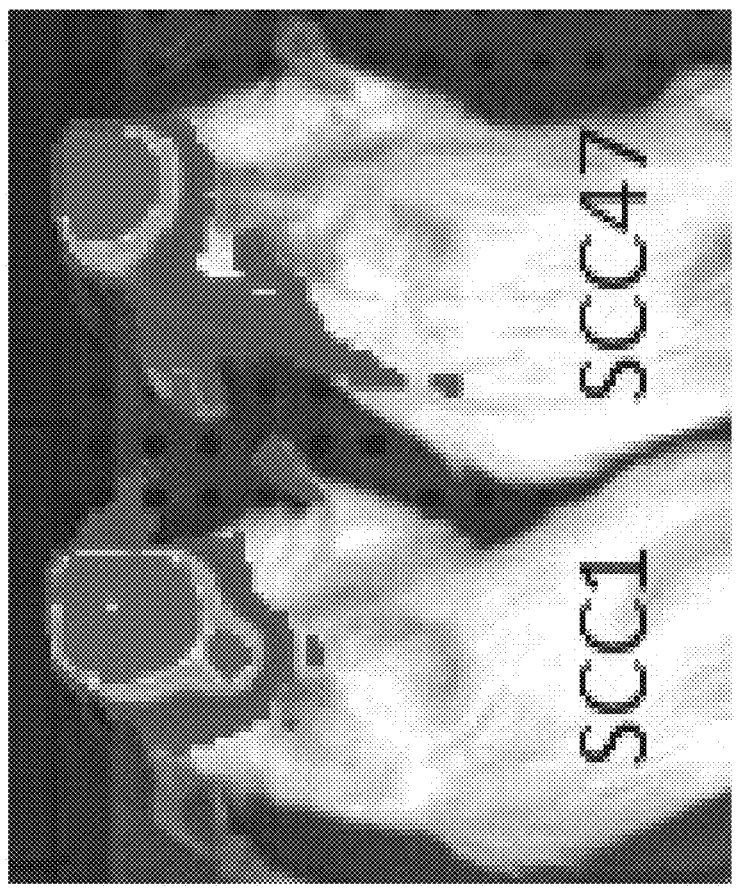
FIG. 25 shows non-invasive imaging reveals development and dissemination of orthotopic HNSCC tumor. Tongues of NSG mice were implanted with SCC1 and SCC47 cells (left and right, respectively). After 10 days, mice were non-invasively imaged by IVIS.

In vivo FA xenograft (local invasion and distal metastasis) assay. Tongues of NSG immunodeficient mice will be injected with tumor cells (luciferase-labeled NTsh and FANCD2sh SCC1 and SCC47, FIG. 25). Tumor formation/growth and dissemination will be monitored by non-invasive in vivo bioluminescence imaging using the IVIS 200 (Calipur Lifesciences). From these imaging data, kinetics of tumor formation will be calculated (the percentage of tumor-free mice vs. age of the mice), tumor incidence (frequency), incidence of local invasion, and incidence of distal metastasis. One hour prior to sacrifice, mice will be injected interperotineally (IP) with 150 mg/kg BrdU. Tongues will be obtained and tumors dissected. Portions of the tumor will be fixed and embedded for IF (e.g., phalloidin), to examine cytoskeletal aberrations and membrane extensions. Other portions will be lysed for western-blot analysis or pull-down assays to quantify DNA-PK and Rac1 activity as a function of FA status. Lungs and livers will be harvested to determine the number of metastatic foci and the percent metastatic tumor area. Sections of tongue, lung and liver will be H&E stained and evaluated histopathologically. Proliferation and apoptosis will be quantified by histological detection of BrdU and activated caspase-3, respectively. If the effect size (mean difference/standard error) for the comparison is greater than or equal to 1, a sample size of 20 mice per group will yields a p-value<0.05 with greater than 80% power.

Localization and mechanism of Rac1 activation in FA-pathway-deficient cells will be determined using biochemical fractionation and testing of guanine nucleotide exchange factors. Mechanistic links between FA, DNA-PK and Rac1 signaling will be investigated.

Cellular compartments of FA-deficient cells will be identified wherein Rac1 and DNA-PK are activated. Lysates of the above FA-proficient and FA-deficient cells will be fractionated into nuclear and cytoplasmic extracts, and then utilized for pull downs and Western-blot analysis to quantify active and total Rac and DNA-PK (as in FIG. 24A, C) FANCD2 and actin will serve as fractionation controls, respectively.

To extract lipid rafts, based on their relative insolubility in established detergent and non-detergent conditions and high buoyancy on density gradients, two established methods will be used (58). In the first method, cells will be dounce homogenized in 1% Triton X-100, cleared, total protein quantified, and remaining supernatant subjected to sucrose-gradient centrifugation; fractions will be quantitatively analyzed for active and total Rac1 and DNA-PK. In the second method, cells will be dounce homogenized in the absence of detergent, sheared through a 20-gauge needle, centrifuged twice, supernatant subjected to sucrose-gradient centrifugation, and then fractions analyzed, as above.

Identification of the GEF-based mechanistic link between DNA-PK and Rac1 signaling in the context of the FA pathway. Because the Rac1 GEF ARHGEF6 has been reported to directly interact with DNA-PK in response to DNA damage, ARHGEF6 will be quantified in isolated LRs. Functional validation will then be tested using shRNA approaches. Links to DNA-PK will be tested using assays as above. Other Rac-specific GEFs, eg TIAM1, Vav2, or PREX2 will each be interrogated similarly. A targeted proteomics approach will be used to identify global changes in GEFs under conditions of FA loss. Total and LR extracts will be subjected to Rac1 pulldown assays, separated by gel electrophoresis, and slices from FA and control lanes will be trypsin digested. Peptides will be identified by high-throughput MS analysis, using matrix-assisted laser desorption ionization-time of flight and/or liquid chromatography-MS (59-60). GEFs identified in this way will then be functionally validated in FA-pathway proficient and FA-pathway deficient normal and transformed cells by examining their activity and distribution. Their specific functional roles in Rac1 activation and FA phenotypes will be tested using similar approaches as above. Cells will be treated with DNA crosslinkers and bleomycin to determine whether cellular damage strengthens candidate FA-pathway-specific Rac1 interactions. Finally, whether DNA-PK and Rac1 GEFs interact in FA deficient cells will be tested using reverse pulldown assays.

Based on FIG. 24, FA loss will likely stimulate and phenotypically require DNA-PK/Rac1, and blocking DNA-PK will likely attenuate Rac1 activation. DNA-PK/Rac1 may not stimulate the motility of FANCD2-deficient NOKS. In this case, DNA-PK/Rac1 independent pathways will be explored. FA patient derived HNSCC cells exhibited elevated DNA repair capacity by NHEJ when compared to their gene-corrected isogenic counterparts (61). Since NHEJ is initiated by DNA-PK activity, is is speculated that FA patient derived VU1131 cells harbor detectable DNA-PK activity which is reversible by complementation. We expect that FA-deficient compared to proficient cells will be more motile in vitro and more invasive, perhaps metastatic, in vivo. We anticipate that DNA/PK or Rac1 inhibition will attenuate these phenotypes. It is also anticipated that constitutive activation of Rac1 will be sufficient for increasing the motility of FA-proficient, but not FA-deficient cells. The outcome of constitutive DNA-PK activation is more difficult to predict: cell cycle arrest or death from a hyper-activated DNA damage response might complicate detection of Rac1 activation and/or invasion.

Rac1 activation is most frequently observed in the cytoplasm and has been associated with LRs, but can also occur in the nucleus. On the other hand, DNA-PK is best known for its nuclear functions, but can localize to LRs. It is anticpated that Rac1 activation in response to FA loss is at least in part observed in LRs. This may coincide with the presence of DNA-PK and ARHGEF in LRs. If Rac1 signaling is not associated with LRs, focus will be on the relevant compartment wherein it is detected, and carry out pulldown experiments with the corresponding lysates. GEFs may not physically associate with DNA-PK, rather they may be indirectly activated by DNA-PK. For example, DNA-PK was reported to phosphorylate Akt under conditions of keratinocyte treatment with UV. Akt activity was shown to promote the accumulation of the Rac1-GEF Tiam 1 for stimulated invasion and metastasis in small cell lung and colon cancer (62-63). A scenario will be tested where Akt is activated by DNA-PK, and responsible for subsequent Tiam1-Rac1 activation. Rac1 activation in FA-deficient cells may not occur through interactions with ARHGEF6 or other GEFs, but rather through the loss of interactions with GAPs. These will also be identified by the targeted proteomics screen.

Figure 26A:
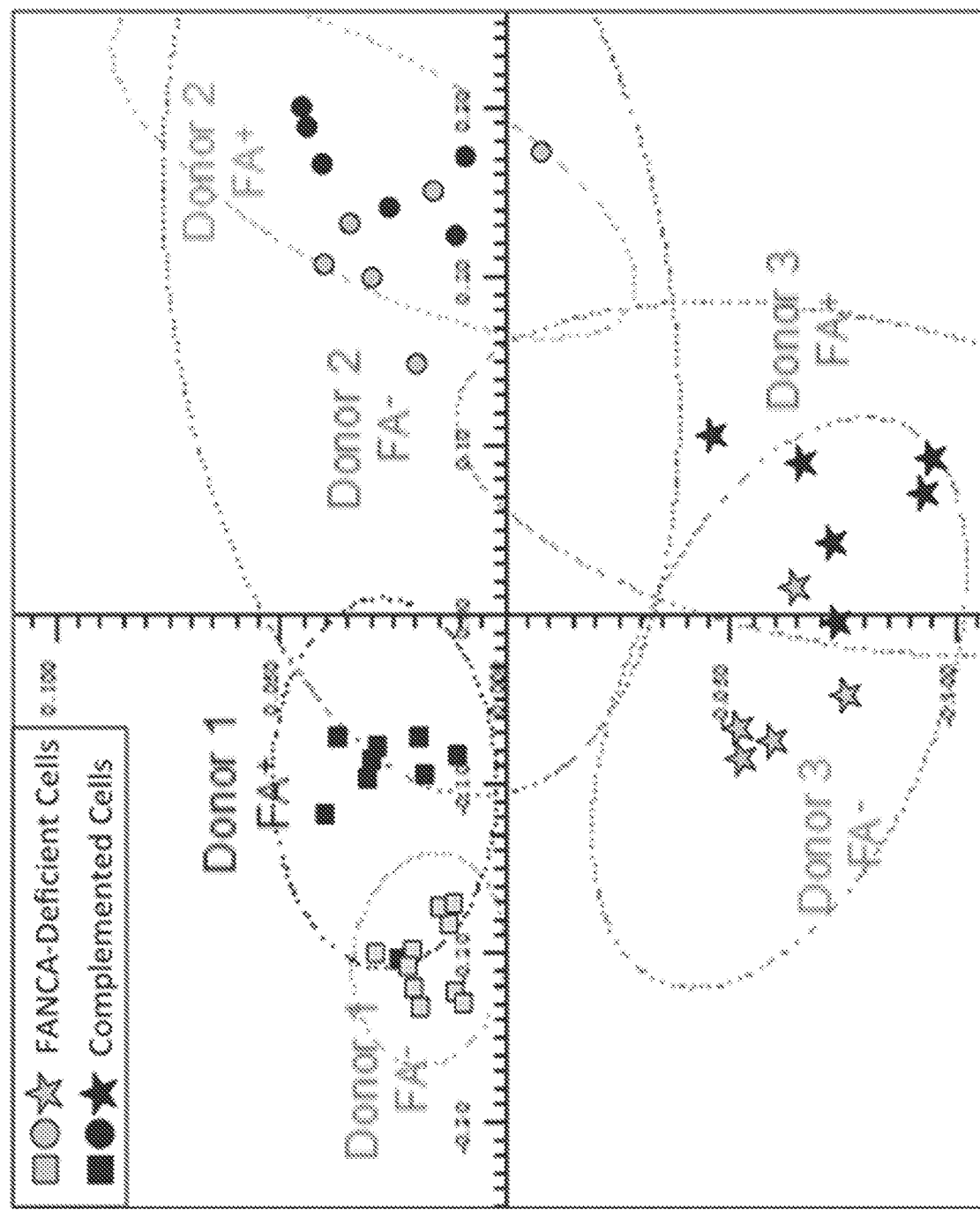
FIG. 26A-C show metabolic profiling distinguishes FA-proficient (black) and FA-deficient (grey) cells. Three FA-modified cell models were utilized for untargeted NMR-based metabolomics analyses.
Figure 26B:
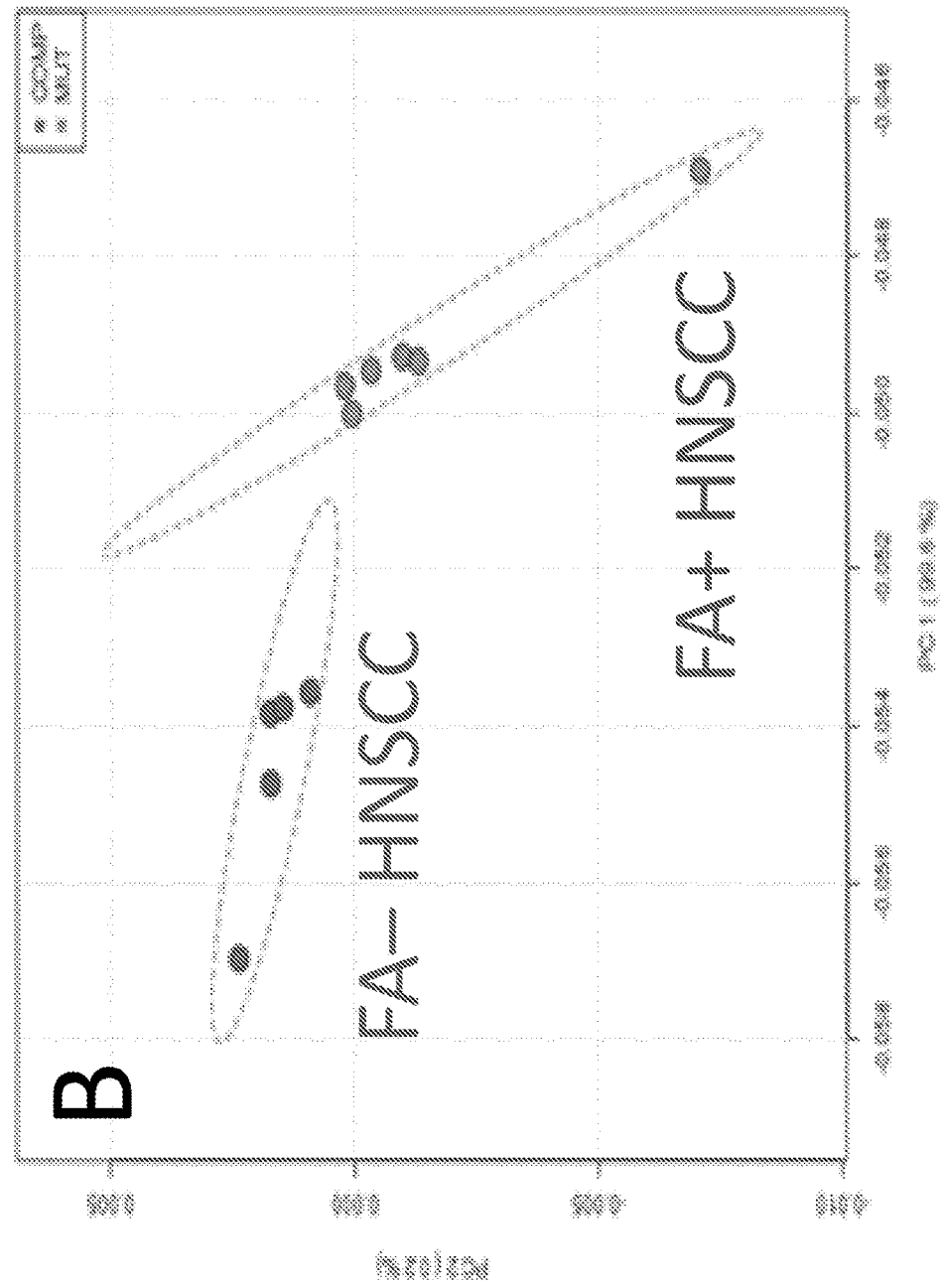
Figure 26C:
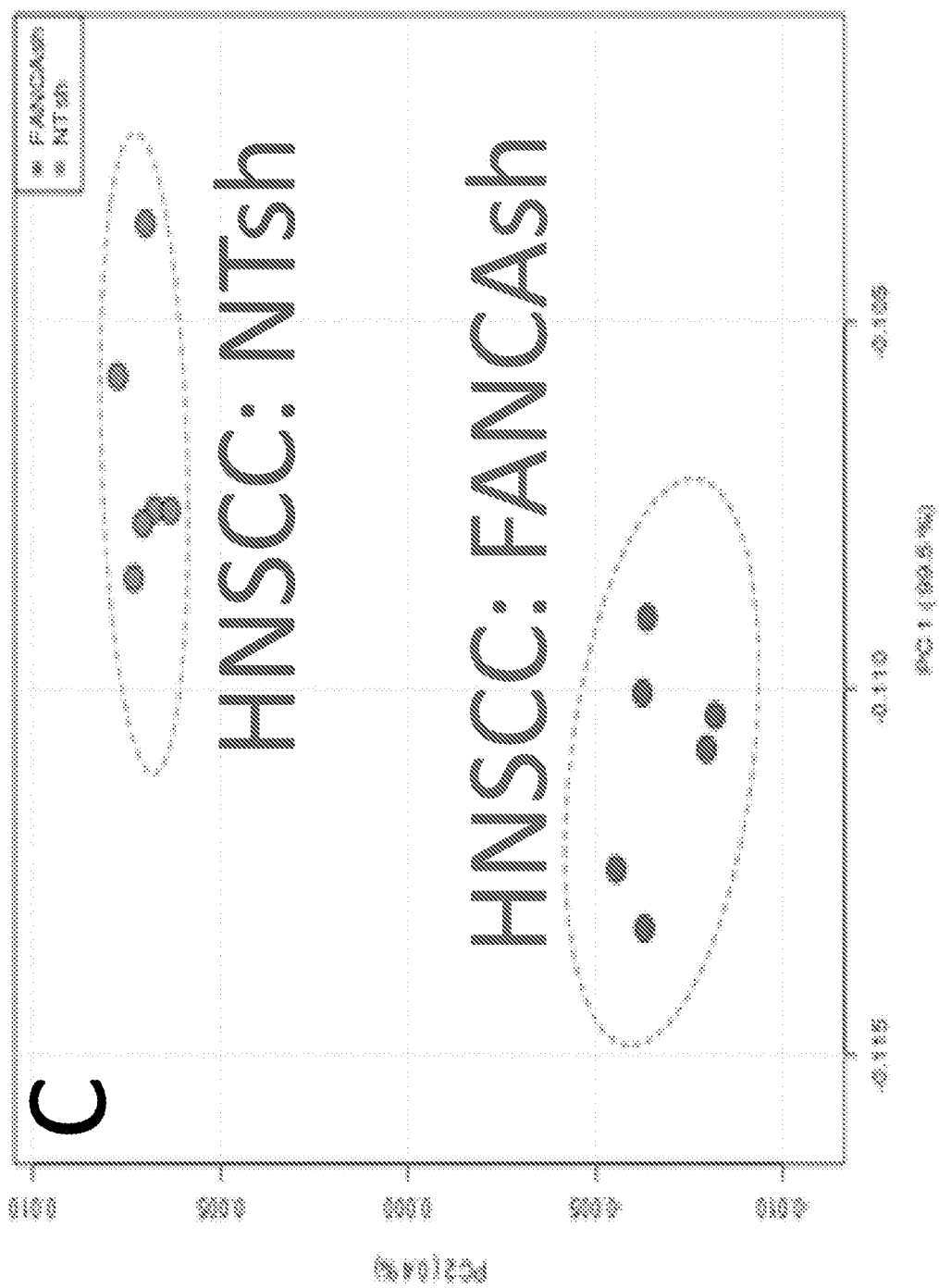

The mechanism of GM3 accumulation will be determined, and blocking GM3 production for the targeting of FA pathologies. NMR- and MS-based metabolomics reveal FA-specific signatures in cell models. FA-specific metabolic de-regulation was studied utilizing three isogenic FA cell models (FIG. 26). Hundreds of small metabolites were detected. For each of the three cell types, FA-deficient cells were distinguished from their isogenic FA-proficient counterparts based on their metabolic profile and the first two principal components.

Figure 1A:
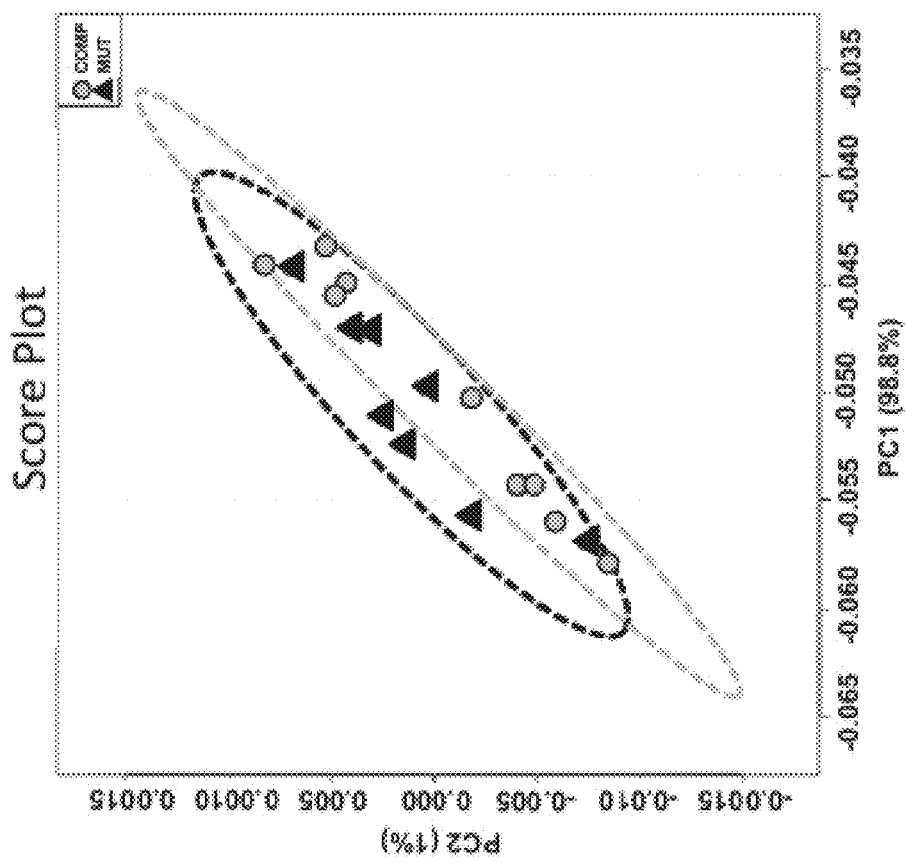
FIGS. 1A-1G show principal component analysis (PCA) score plots comparing the cellular metabolic differences in cells in both a premalignant FIGS. 1A and 1B; and malignant FIG. 1C, FIG. 1D, FIG. 1E, FIG. F and FIG. 1G state obtained using nuclear magnetic resonance (NMR) spectroscopy. A total of seven cell lines are used in the comparison: two immortalized human keratinocyte lines (FA IHKs$^{comp}$) derived from individuals with FANCA mutations (MUT/Circle) compared to the same cells following complementation with the FANCA gene (COMP/Triangle), two head and neck cancer Fanconi Anemia (FA) patient-derived cell lines (FA HNC$^{comp}$) comparing cells with the FANCA gene mutation (MUT/Circle) with the same cells following complementation (COMP/Triangle), and three sporadic head and neck cancer patient cell lines (FA HNC$^{kd}$) transduced with either non-targeting shRNA (NTsh/Triangle) or FANCA shRNA (FANCAsh/Circle). Circles indicate 95% confidence intervals of each group.
Figure 1B:
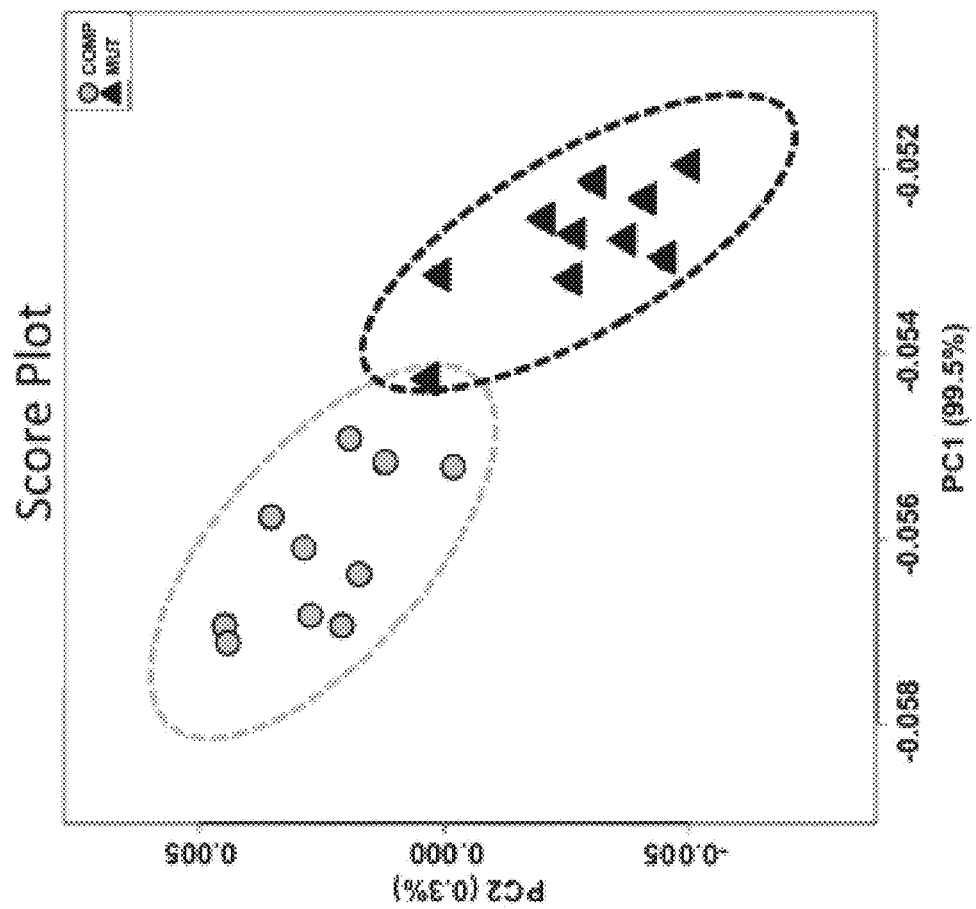
Figure 1C:
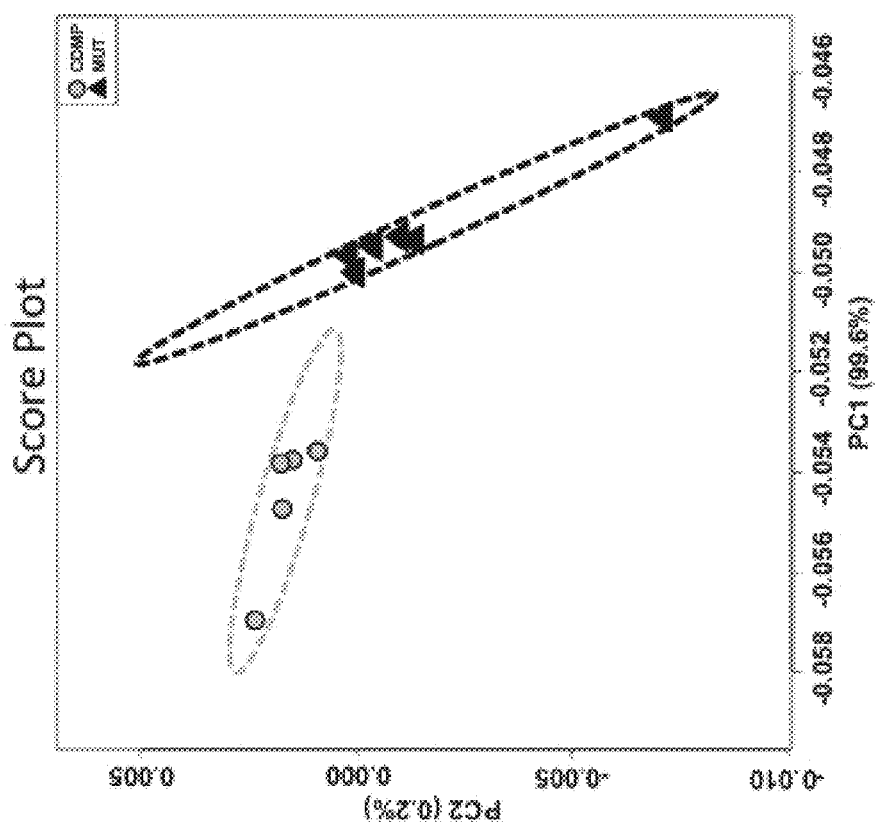
Figure 1D:
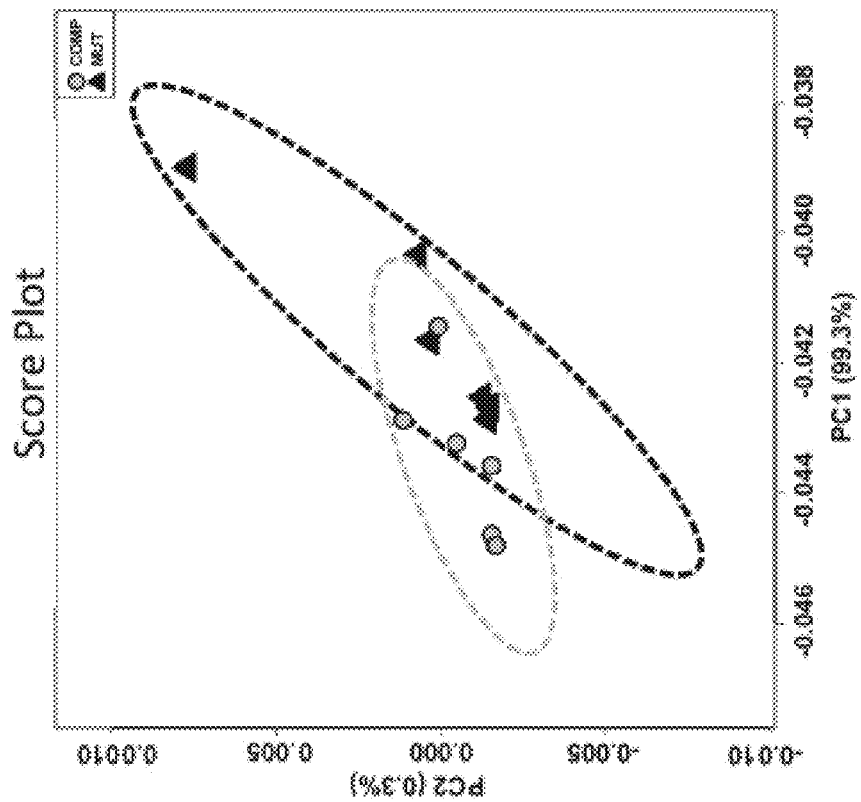
Figure 1E:
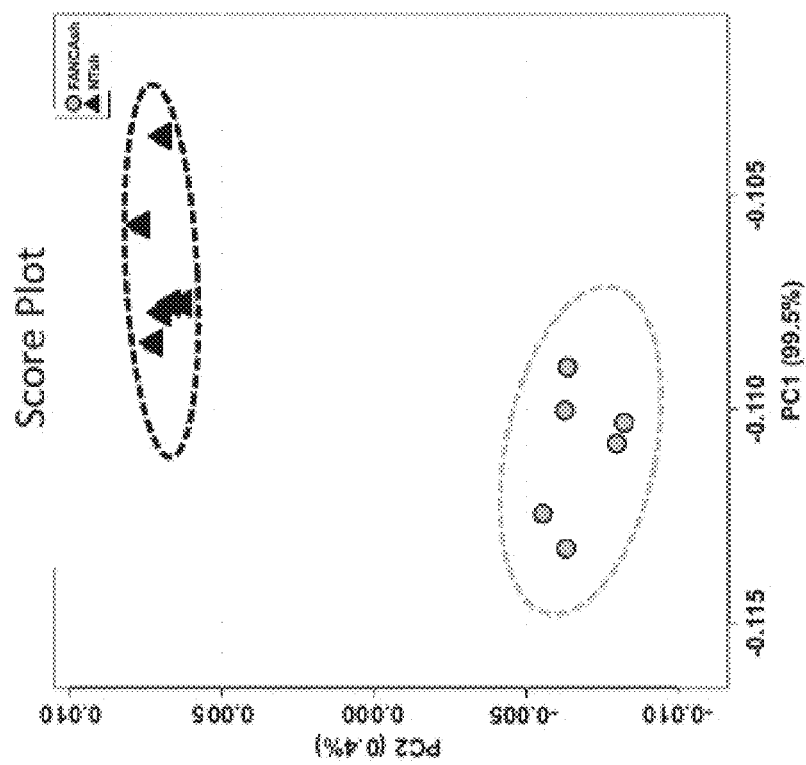
Figure 1F:
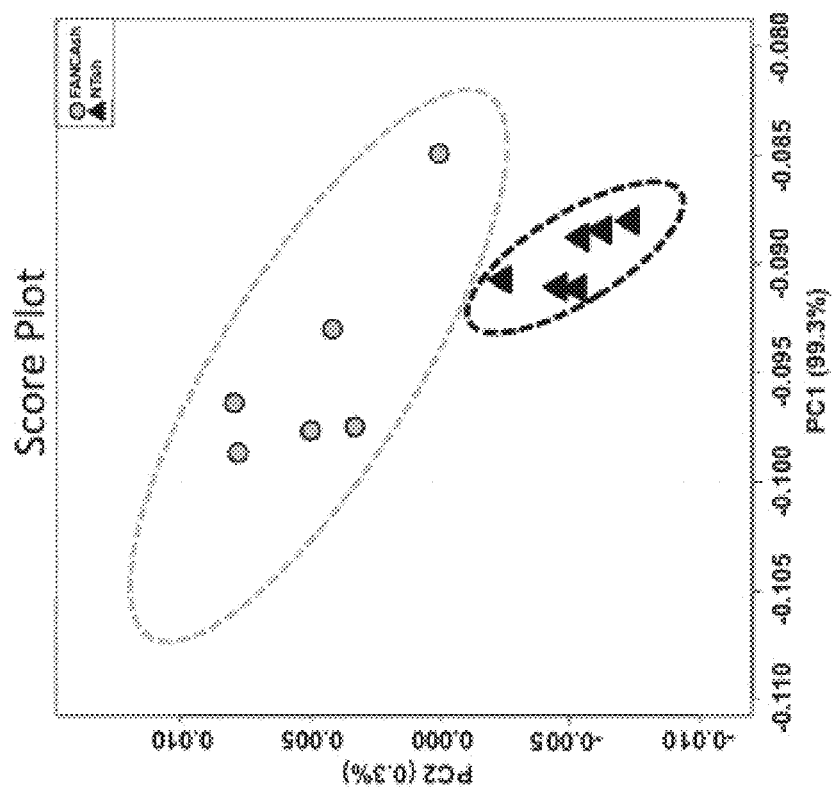
Figure 1G:
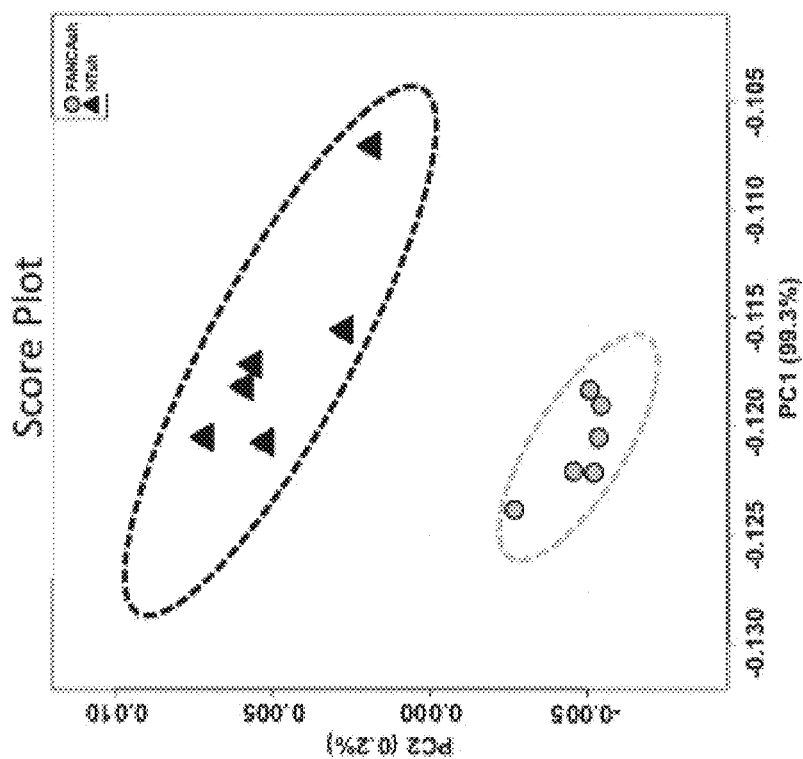
Figure 2A:
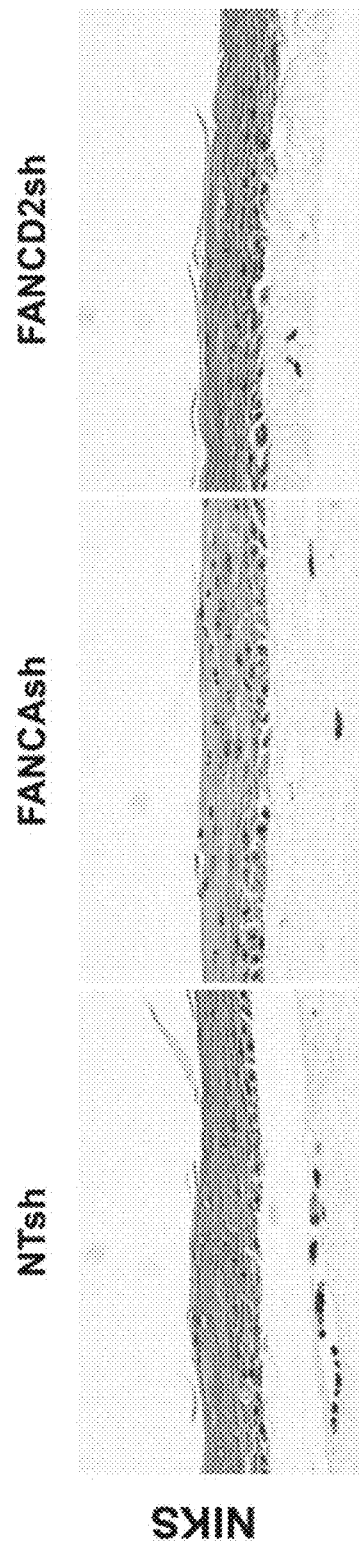
FIG. 2A shows three-dimensional organotypic raft cultures of normal immortalized keratinocytes (NIKS) transduced with non-targeting shRNA (NTsh), FANCA knockdown shRNA (FANCAsh) or FANCD2 knockdown shRNA (FANCD2sh).
Figure 3A:
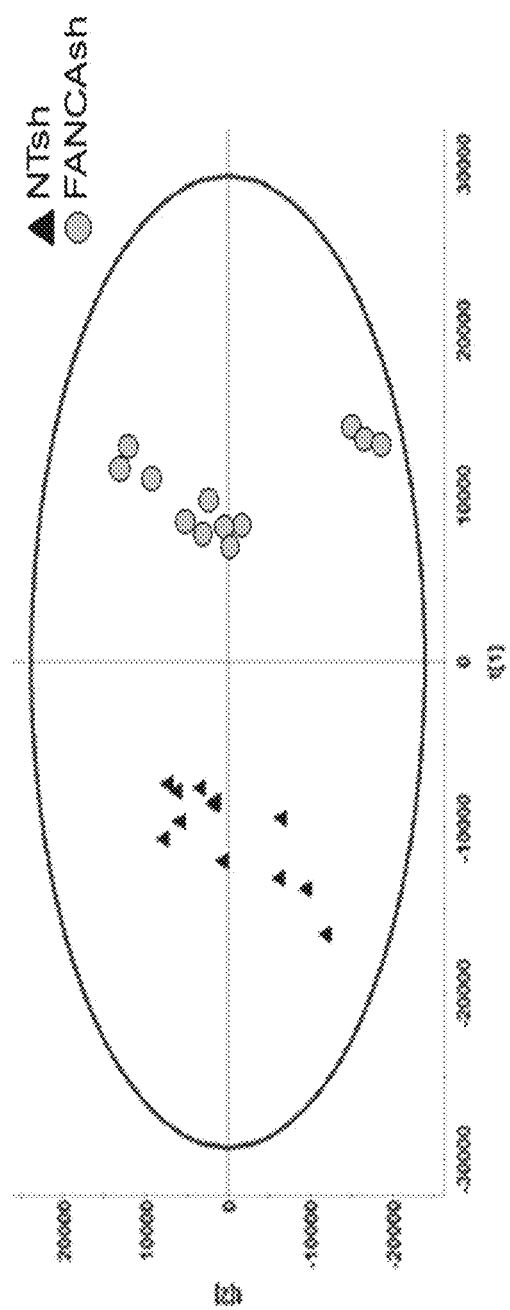
FIG. 3A and FIG. 3B show principal component analysis (PCA) score plots comparing the cellular metabolic differences in cells using mass spectrometry (MS).
Figure 3B:
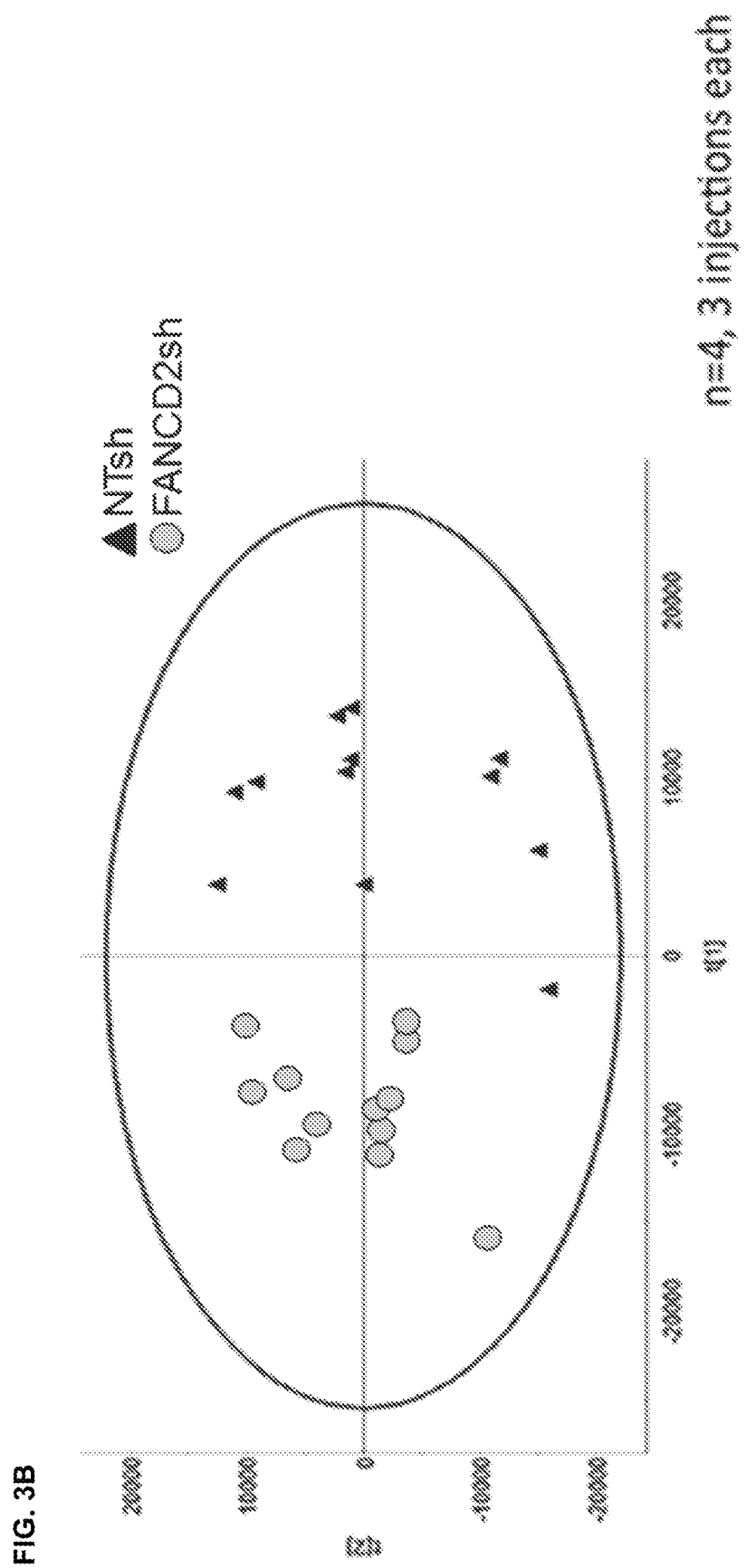
Figure 4:
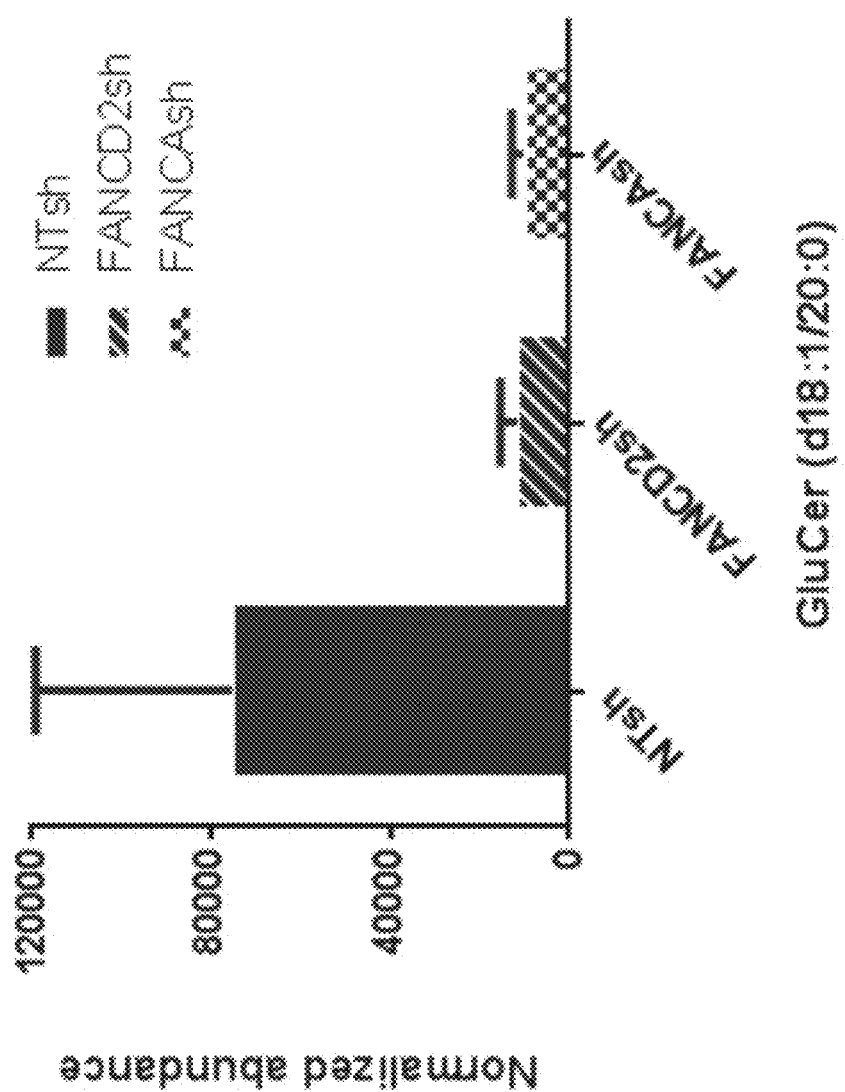
FIG. 4 shows ion intensity profile of glucosylceramide (d18:1/20:0) in NTsh, FANCD2 mutation and FANCA mutation NIKS cells (n=4).
Figure 5:
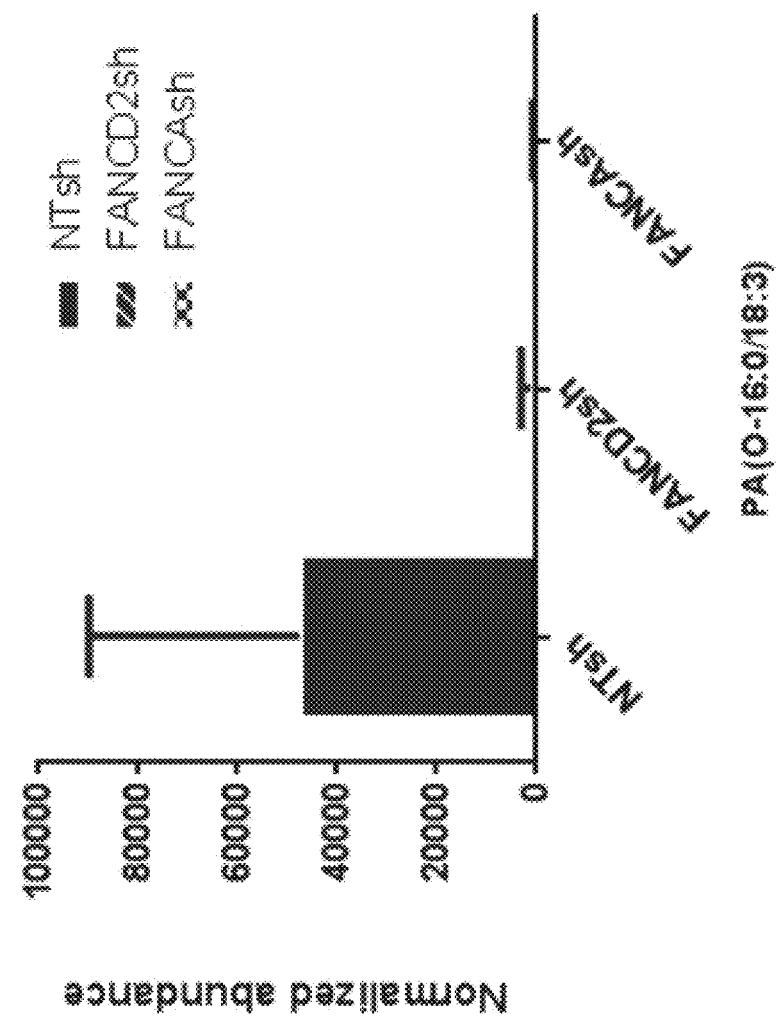
FIG. 5 shows ion intensity profile of phosphatidic acid (O-16:0/18:3) in NTsh, FANCD2 mutation and FANCA mutation NIKS cells (n=4).
Figure 6:
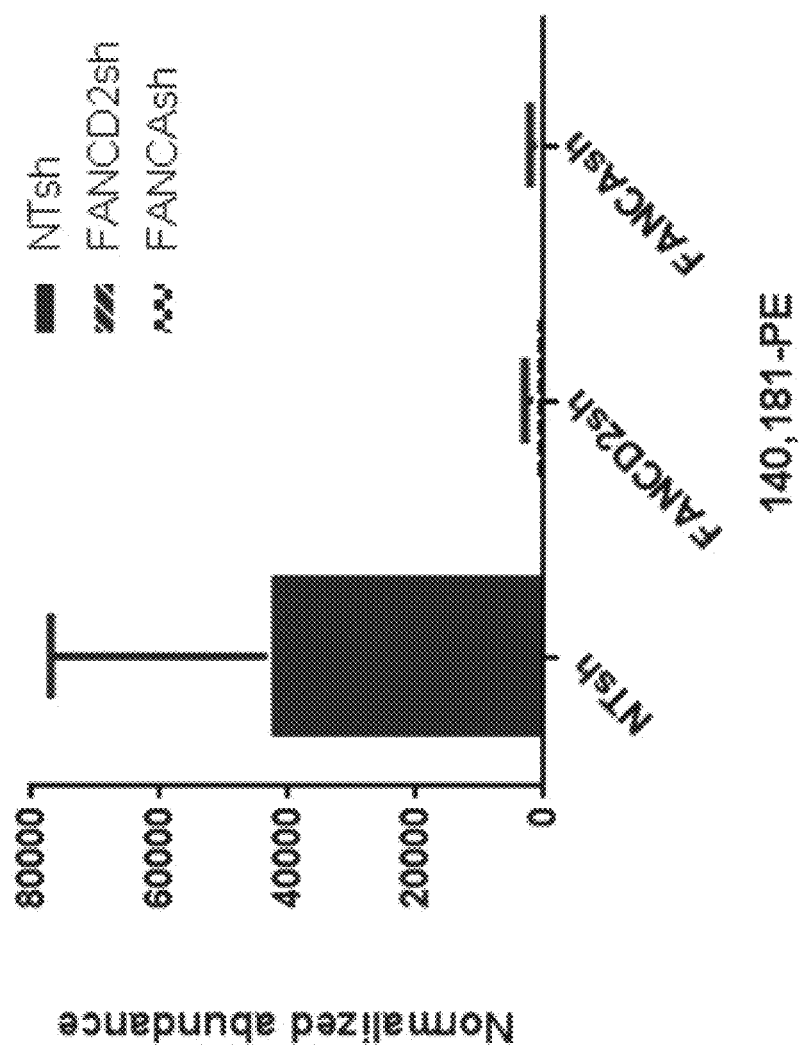
FIG. 6 shows ion intensity profile of phosphatidylethanolamine (14:0/18:1) in NTsh, FANCD2 mutation and FANCA mutation NIKS cells (n=4).

FIG. 26 shows metabolic profiling distinguishes FA-proficient and FA-deficient cells. Three FA-modified cell models were utilized for untargeted NMR-based metabolomics analyses: (A) keratinocytes, cultured from the skin of three FANCA patients, were immortalized with the HPV16 E6/E7 oncogenes, and then transduced to correct for the FANCA gene (vs control). (B) HNSCC cells cultured from the primary tumor of a FANCA patient, and then either control transduced of complemented with FANCA. (C) FANCA-knockdown UM-SCC1 cells (vs. control) (FIG. 1A). Score plots are 2D representations of the principal component analysis (PCA), with each point representing a separate cellular NMR spectrum; multiple points of the same color represent experimental replicates. Solid oval lines indicate 90% confidence intervals for the two clusters of data points in each case.

Complimenting the NMR-based metabolomics study was a piloted an MS metabolomics approach, offering orders of magnitude greater sensitivity for a wide range of metabolites. PCA of thousands of metabolite-ion features showed that FANCD2sh-treated NIKS and SCC1 cells segregated from their respective NTsh-treated cells due to distinct metabolic profiles (FIG. 27A). The next focus was on metabolites that were regulated with high significance upon FA pathway loss (FIG. 27B), and subsequently analysis of the negative ion dataset from HNSCC cells. Only nine negative ions were significantly different in FANCD2sh-treated versus NTsh-treated cells after conservative Bonferroni correction; two of these were gangliosides from the same lipid class that were prominently upregulated: GM3 (d34:1) and its metabolic product GD1 (d34:1) (FIG. 27C). The downstream ganglioside GM1 was also upregulated, albeit at a lesser p value (not shown). Targeted analysis was therefore performed using UPLC-MS/MS monitoring of a broader range of ganglioside metabolites. Because available ganglioside standards contain only a portion of the ceramide moiety lengths detected in the cell extracts, an expanded MS/MS was adapted where theoretical calculated precursor and fragment ions were used to cover a wide range of ganglioside structures (FIG. 27D). These data demonstrated that FANCD2 loss stimulated ganglioside biosynthesis in both normal and transformed keratinocytes.

GM3 is the precursor of complex gangliosides (FIG. 27E), a key component of cell membranes, and enriched in lipid rafts (LRs). GM3 and its derivative GM1 localize to microdomains in apical epithelial membranes (68) and GM3 depletion was reported to blocked wound healing in diabetic mice (69). Further, GM3 was elevated in head and neck tumors (compared to adjacent normal tissue) (70) and in serum of HNSCC patients, and was predictive of tumor size and relapse (71). On the other hand, links between GM3 levels and FA have not yet been reported. Targeted analyses by UPLC-MS/MS in normal cutaneous (NIKS) and normal oral (NOKS) keratinocytes, as well as in UM-SCC1 cells verified GM3 regulation across the major carbohydrate component lengths (i.e., from d34:1 to d44:2) (FIG. 27F-H). Together, the results showed consistent upregulation of ganglioside biosynthesis in normal and transformed keratinocytes that have been depleted of FANCD2 or FANCJ (not shown). To assess the functional significance of ganglioside accumulation in FA cells, the effect of a ganglioside synthesis inhibitor N-butyldeoxynojirimycin (NB-DNJ)72 was measured on invasion driven by FA pathway loss. NTsh-, FANCD2sh- and FANCJsh-treated SCC1 and SCC47 cells were exposed to NB-DNJ (or vehicle), and subjected to Matrigel invasion assays (FIG. 23). NB-DNJ reduced GM3 levels in all cell populations (FIG. 27K), and selectively inhibited invasion driven by FA loss (FIG. 27I, J). Conversely, GM3 addition to the culture media stimulated SCC1 invasion, and particularly in FA-proficient cells (data not shown). Together, these data indicated that GM3 upregulation in response to FA loss was functionally important and occurred in normal and transformed keratinocytes.

FA deficient epidermal rafts displayed structural and differentiation abnormalities. FANCD2sh or NTsh-treated NIKS were subjected to organotypic epithelial raft culture 73, and analyzed by EM. FANCD2 loss resulted in abnormal appearance of desmosomes and cell-cell contacts similar to observations in skin of FA patients (FIG. 21). Further, intracellular vesicle accumulation and vesicular protrusions from the apical surface were noted. These abnormalities were only evident by ultrastructural analysis and were not revealed by H&E staining of the respective rafts (73). Collectively, the data implicated DNA-PK/Rac1 signaling and ganglioside de-regulation in FA SCC phenotypes, and have established relevant normal and transformed human models where the role and regulation of these molecules can now be tested.

FIG. 28 shows FA deficient epithelial rafts harbor perturbations in membrane and adhesion characteristics.

Ultrastructural adhesion abnormalities in the skin of individuals with FA. As shown in FIG. 34 A. Skin punch biopsies from normal control versus FA subjects were fixed, sections and used for H&E staining. These were morphologically normal but exhibited pigment incontinence in 3/6 subjects in FA only which could not be explained by race and is consistent with basal cell injury. As shown in FIG. 34 B. Skin-punch biopsy tissue, sectioned and immunostained for K14, K10 and DAPI.C. Representative EM images of skin-punch biopsies from 9 FA patients (no bone marrow transplant) and 5 controls (top), and tongue (mucosal) epidermis from 2 FancD2 knockout and 2 wild-type mice (bottom). Biopsies were processed and analyzed by EM. Desmosome counts were cell were significantly reduced.

Loss of FA pathway impairs intercellular adhesion in NIKS. Membrane filaments also present in SCC cells knocked down for FA. Loss of FA pathway correlated with invasion and DNA-PK/Rac1 signaling. As shown in FIG. 35 A. Representative EM images of NIKS-derived organotypic epithelial rafts independently transduced with either NTsh (n=2) or FANCD2sh (n=2). FIG. 35 B. confocal microscopy of monolayer cells from FIG. 35 A. NIKS in monolayer culture were immunostained for K14 (green), phalloidin (red) and DAPI and subjected to confocal microscopy to visualize intercellular gaps. Images of immunostained cytoskeletal elements were acquired on a Nikon A1 confocal using a 100×NA 1.45 objective, nyquist sampling, and a 1.2 A.U. pinhole. Z-stacks were acquired through the thickness of the cell layer (~7 um) using a 150 nm step size to allow for sufficient overlap of optical sections for 3D reconstruction. Intercellular spaces were quantified from 7 images each, using Nikon Elements General Analysis software. Binary thresholds were set to create a binary mask on phalloidin-low intensity gaps between cells. The area of this binary mask was quantified. Preliminary quantitation suggests more pronounced intercellular gaps.

The contribution of ganglioside biosynthesis to FA pathway-dependent outcomes in normal and pathological epidermal systems is being determined. The inventors hypothesize that the FA pathway maintains epidermal homeostasis through control of GM3 biosynthesis. To probe the regulation and function of gangliosides in FA deficient cells, stable isotope resolved metabolomics experiments coupled with MS will be performed, and then quantifing and manipulating GM3 in keratinocytes and HNSCCs isogenic for FA. Up- and downregulation of GM3 is followed by phenotypic analyses, and exploration of crosstalk with DNA-PK/Rac1 signaling through lipid rafts. As a first step towards clinical translation, ganglioside levels and transepithelial barrier function will be measured in the skin of FA patients, in correlation with pathological defects (FIG. 21).

Enzyme mediators of FA-dependent ganglioside regulation will be identified by isotope tracing experiments. To further mine the importance of ganglioside biosynthesis in FA-deficient cells, a series of stable isotope-labeled tracer experiments will be performed, with each one using one of three GM3 precursors. This targeted approach builds on mapping biochemical defects in lipid-storage diseases (e.g., Gaucher's), and will utilize existing lipidomic platform using high sensitivity mass spectrometry for monitoring specific transitions for the natural and stable-isotope labeled intermediates. Initially, NOKS versus UMSCC1+/−

FANCD2 will be utilized to complement preliminary GM3 detection data (FIG. 27G). Cells will be incubated with stable isotope-labeled serine (as in FIG. 30), fatty acid (e.g., palmitic acid) or ceramide; the ceramide will be synthesized by methods known in the art. The use of stable-labeled ceramide should provide a direct in vitro means of evaluating the enzyme activity of glucosyl ceramide synthase and GM3 synthase. At different time points, lipids and sphingolipids will be extracted, and analyzed using highly sensitive ESI-LC-MS. By tracing the isotopic enrichment of sphingolipid and ganglioside metabolic intermediates, the rate of isotope incorporation into ceramide, and the extent to which the isotope is incorporated into the GM3 pathway, will be determined. By repeating these experiments with three different precursors, an atom-resolved map will be derived of the pathway for sphingolipid and ganglioside synthesis in response to FA loss, and the point(s) of specific metabolic blocks and/or increased enzyme activity will be determined. The expression of candidate enzymes (e.g. GM3 synthase) will be quantified by Western blot in FA deficient versus proficient cells. FA-regulated enzymes will then be manipulated to assess a functional role in producing phenotypes in FA deficient cells. To determine whether FA-pathway dependent ganglioside regulation is reversible, FA-patient-derived VU1131 versus isogenic complemented cells for similar studies will initially be used.

Determination whether FA-pathway-dependent control of GM3 regulates keratinocyte adhesion and motility, and target GM3 therapeutically, alone or in combination with DNA-PK/Rac1. FA-dependent consequences of GM3 modulation. FA isogenic cell pairs will be grown in organotypic raft cultures 61: NOKS and SCC1 cells, knocked down for FANCD2; and VU1131 FA-patient-derived HNSCC cells will be utilized initially. Additional cell lines are available for verification (Table 2).

Inhibit GM3 accumulation. The glucosylceramide synthase inhibitor NB-DNJ will initially be used. This drug is already approved by the U.S. Food and Drug Administration for oral treatment of the glycosphingolipid metabolism disorder type-1 Gaucher disease, does not affect cell growth, and has successfully repressed GM3 levels (FIG. 27K). Other commercially available glucosylceramide synthase inhibitors will be used for verification (eg, Genz529468) (74). GM3 accumulation will also be inhibited by knock down of the GM3 synthase gene St3Gal5, using a GFP-marked lentiviral vector. Cell populations will be transduced, sorted, and GFP+ populations quantitatively analyzed for GM3 synthase protein levels by Western blot analysis. The anticipated GM3 suppression for each approach will then be validated by MS.

Stimulate GM3 accumulation. GM3 will be added to the cell media at a concentration of 50 uM where GM3 doubled the invasion of SCC1 cells. In addition, GM3 synthase will be overexpressed using stable lentiviral St3Gal5 expression vectors (similar to 75). GM3 increases will then be validated by MS. To ensure that the GM3 inhibition and stimulation protocols do not impact cell viability or proliferation, cells will be counted over time, and flow cytometry will monitor BrdU incorporation (proliferation) and caspase 3 cleavage (cell death).

Definition of the FA-dependent status of desmosome and hemidesmosome components. Desmosome and hemidesmosome pathologies were noted in the skin of FA patients (FIG. 21). Further, desmosomal cadherins and hemidesmosomal a6b4 receptors are associated with lipid rafts, and stabilized therein (76). Cells and organotypic lipid rafts as described will therefore be analyzed as follows. Cytoskeletal and membrane organization will be visualized by phalloidin and filipin staining; cells with intercellular membrane filaments will be quantified as in FIG. 22. Cell-cell contacts will be detected by IF for E-cadherin. Intercellular adhesion complexes will be detected by IF for core desmosome components from three protein families: (a) desmosomal cadherins (desmogleins and desmocollins); armadillo proteins (plakophilins and plakoglobin); and plakin proteins, particularly desmoplakin. Integrin a6b4 and the associated plektin protein, both essential for hemidesmosome assembly (77-78) will also be detected by IF. To quantify expression of the same proteins, lysates of the cells and lipid rafts will be subjected to quantitative Western blot analysis, in the presence of GM3 inhibition or stimulation. DNA-PK/Rac1 signaling, as well as invasion and motility will be analyzed as described.

To test whether GM3 inhibition rescues normal FA epidermis and suppresses orthotopic HNSCC tumor progression, FA-deficient and -proficient lipid rafts and tumors, generated from the St3Gal5sh and NTsh cell pairs, will be treated with NB-DNJ or vehicle throughout the experiment.

Figure 7:
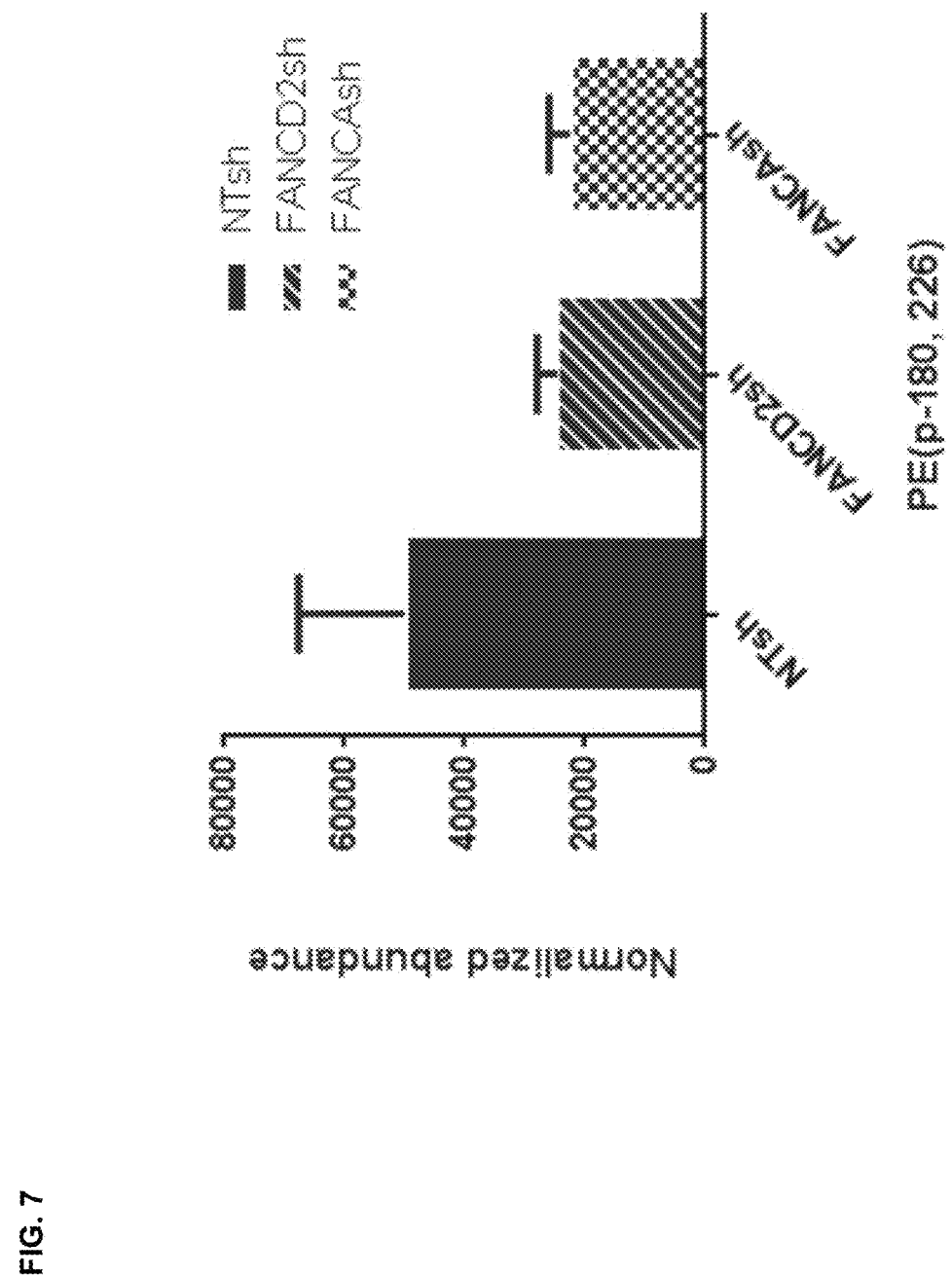
FIG. 7 shows ion intensity profile of phosphatidylethanolamine (p-18:0/22:6) in NTsh, FANCD2 mutation and FANCA mutation NIKS cells (n=4).
Figure 8:
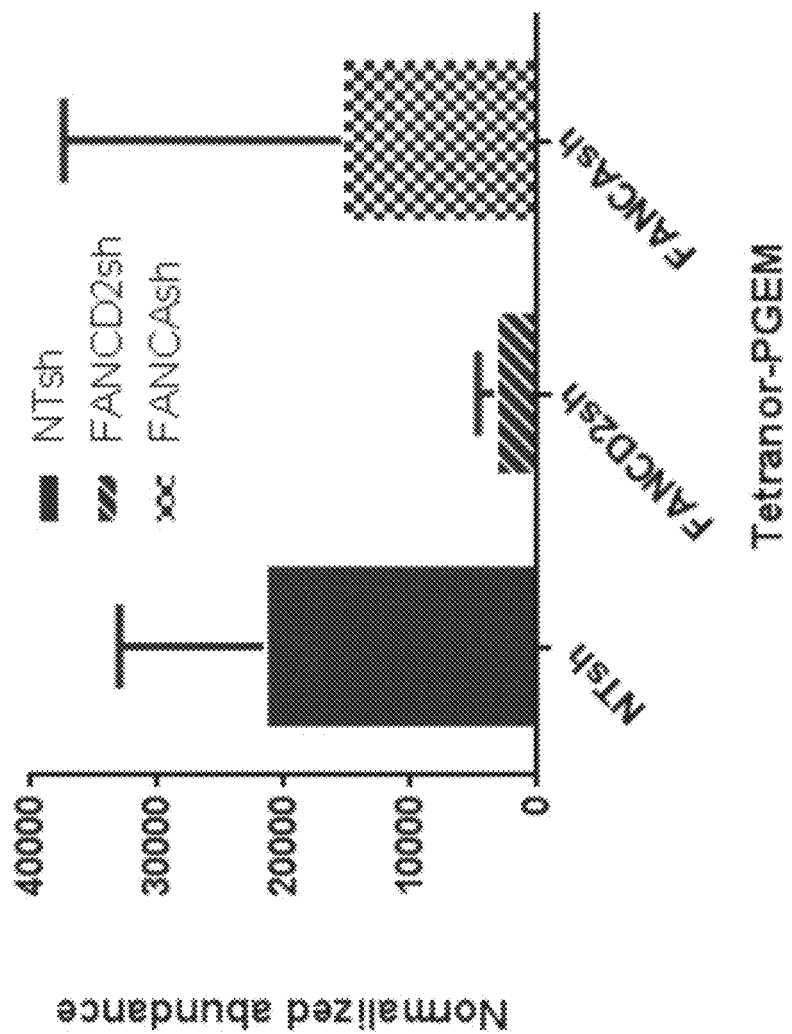
FIG. 8 shows ion intensity profile of Tetranor-PGEM in NTsh, FANCD2 mutation and FANCA mutation NIKS cells (n=4).
Figure 9:
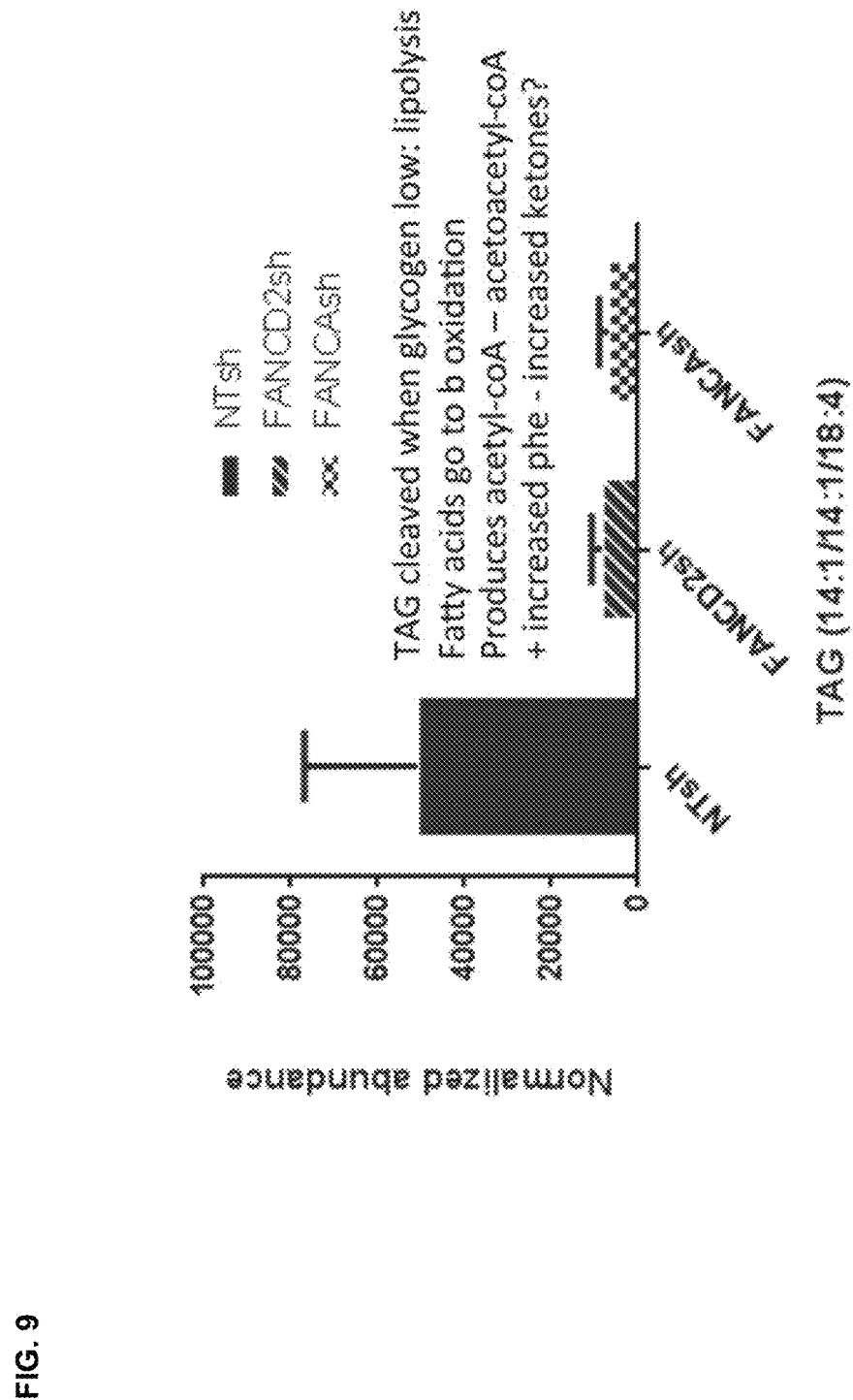
FIG. 9 shows ion intensity profile of TAG (14:1/14:1/18:4) in NTsh, FANCD2 mutation and FANCA mutation NIKS cells (n=4).
Figure 10:
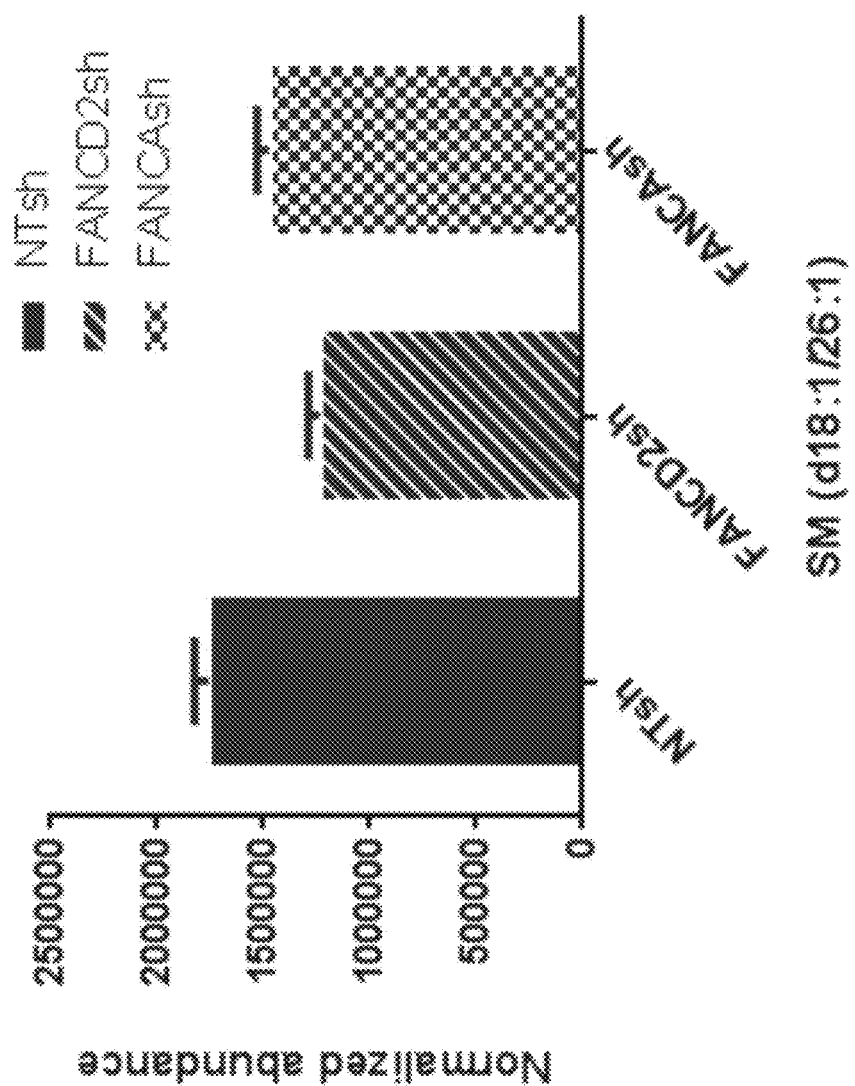
FIG. 10 shows ion intensity profile of sphingomyelin (d18:1/26:1) in NTsh, FANCD2 mutation and FANCA mutation NIKS cells (n=4).
Figure 11:
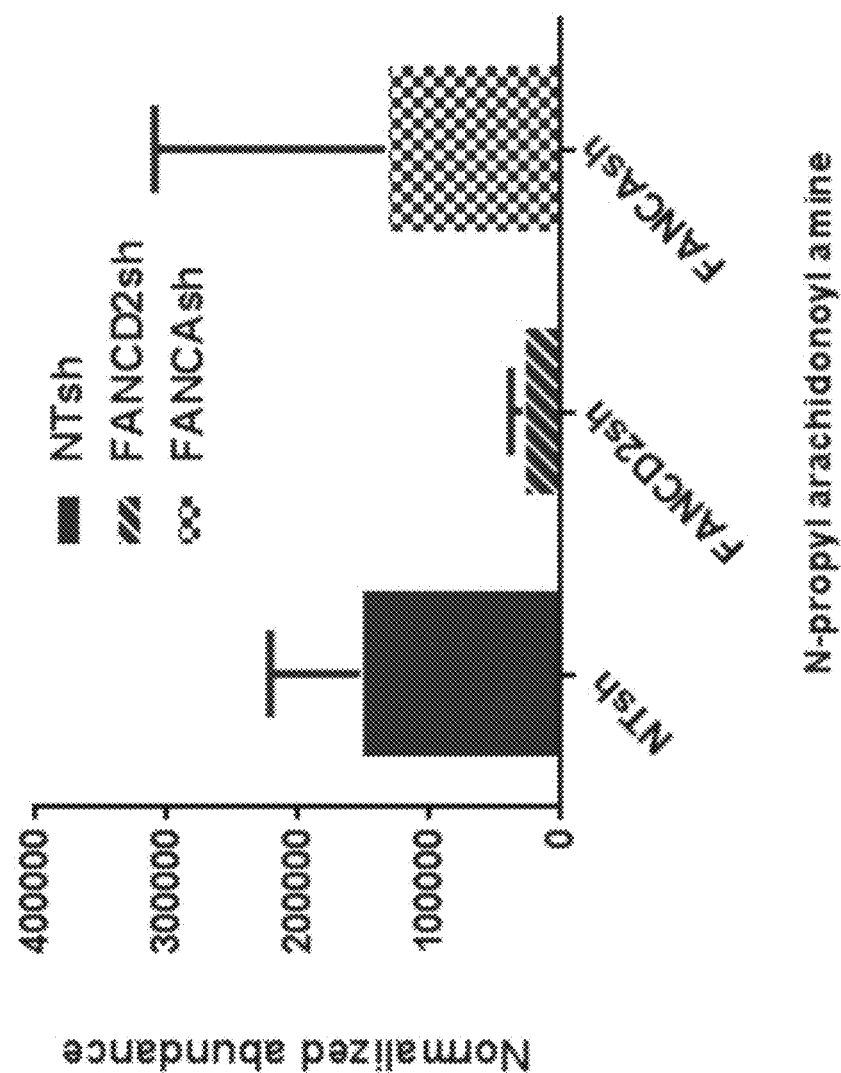
FIG. 11 shows ion intensity profile of N-propyl arachidonoyl amine in NTsh, FANCD2 mutation and FANCA mutation NIKS cells (n=4).
Figure 12:
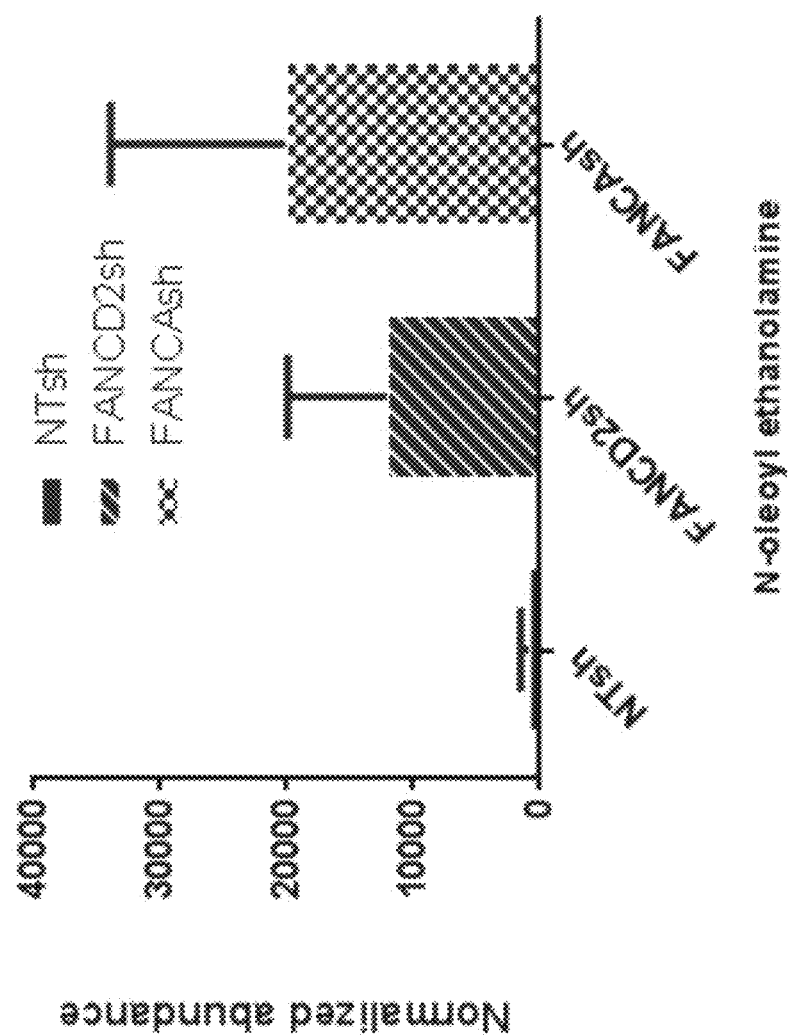
FIG. 12 shows ion intensity profile of N-oleoyl ethanolamine in NTsh, FANCD2 mutation and FANCA mutation NIKS cells (n=4).
Figure 13:
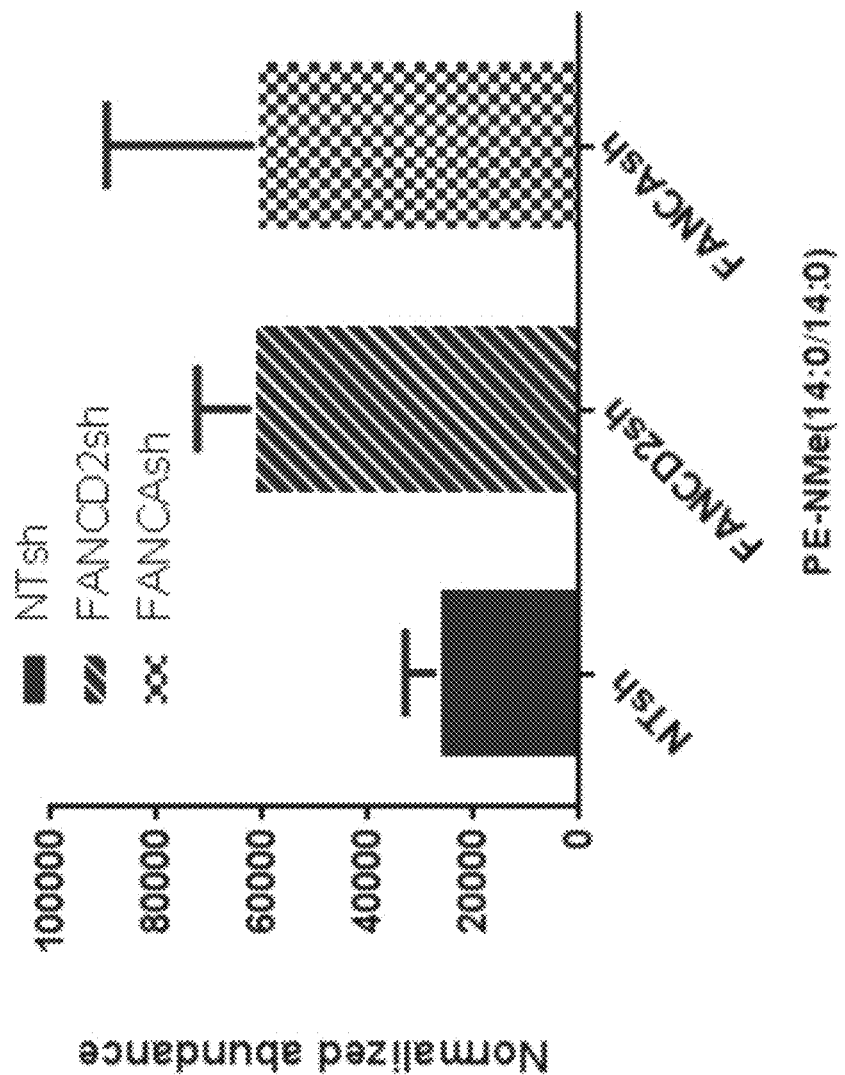
FIG. 13 shows ion intensity profile of PE-NMe (14:0/14:0) in NTsh, FANCD2 mutation and FANCA mutation NIKS cells (n=4).
Figure 14:
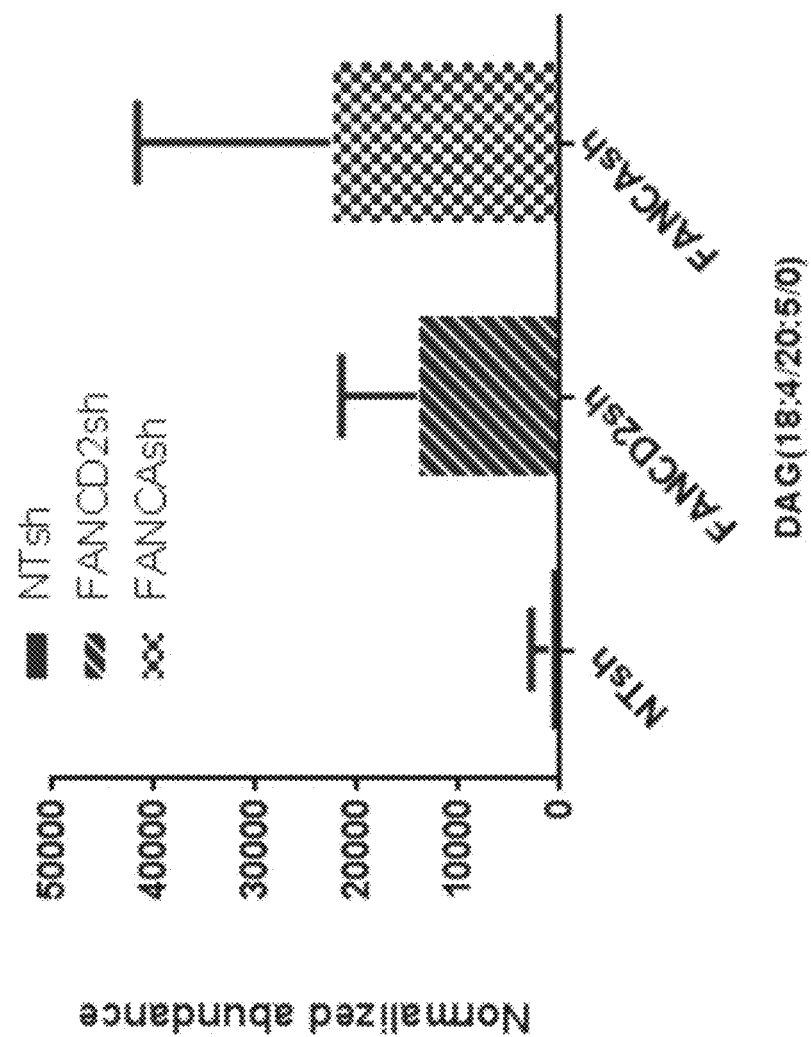
FIG. 14 shows ion intensity profile of DAG (18:4/20:5/0) in NTsh, FANCD2 mutation and FANCA mutation NIKS cells (n=4).
Figure 15:
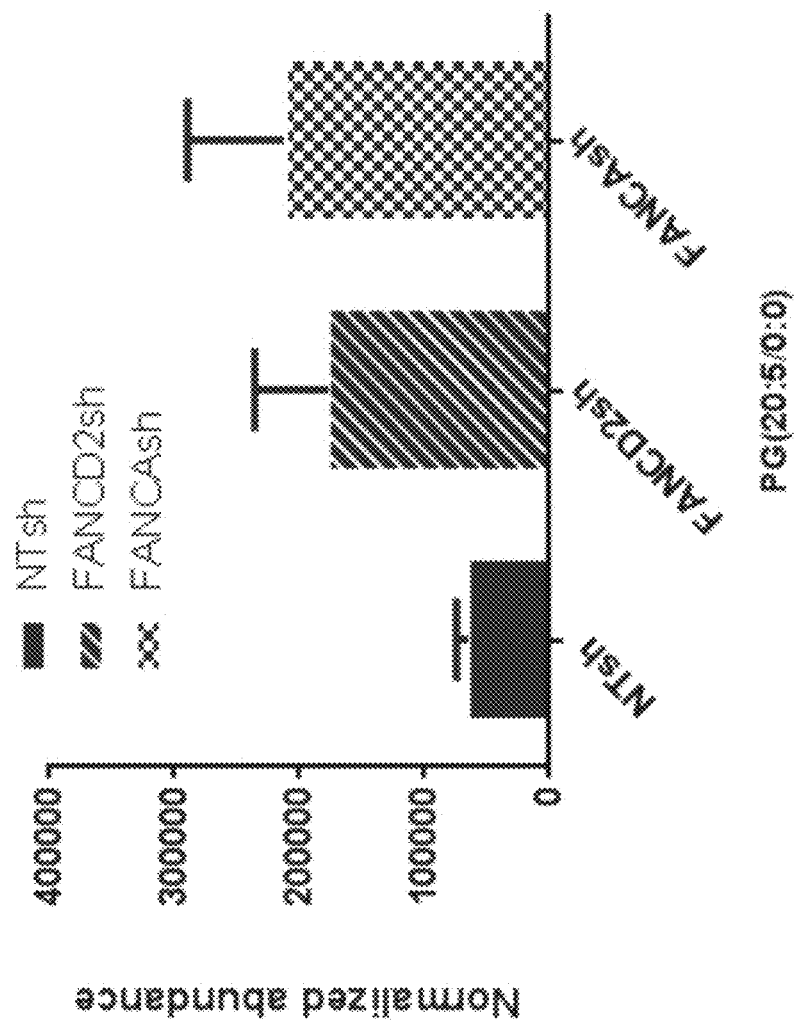
FIG. 15 shows ion intensity profile of phosphatidylglycerol (20:5/0:0) in NTsh, FANCD2 mutation and FANCA mutation NIKS cells (n=4).
Figure 16:
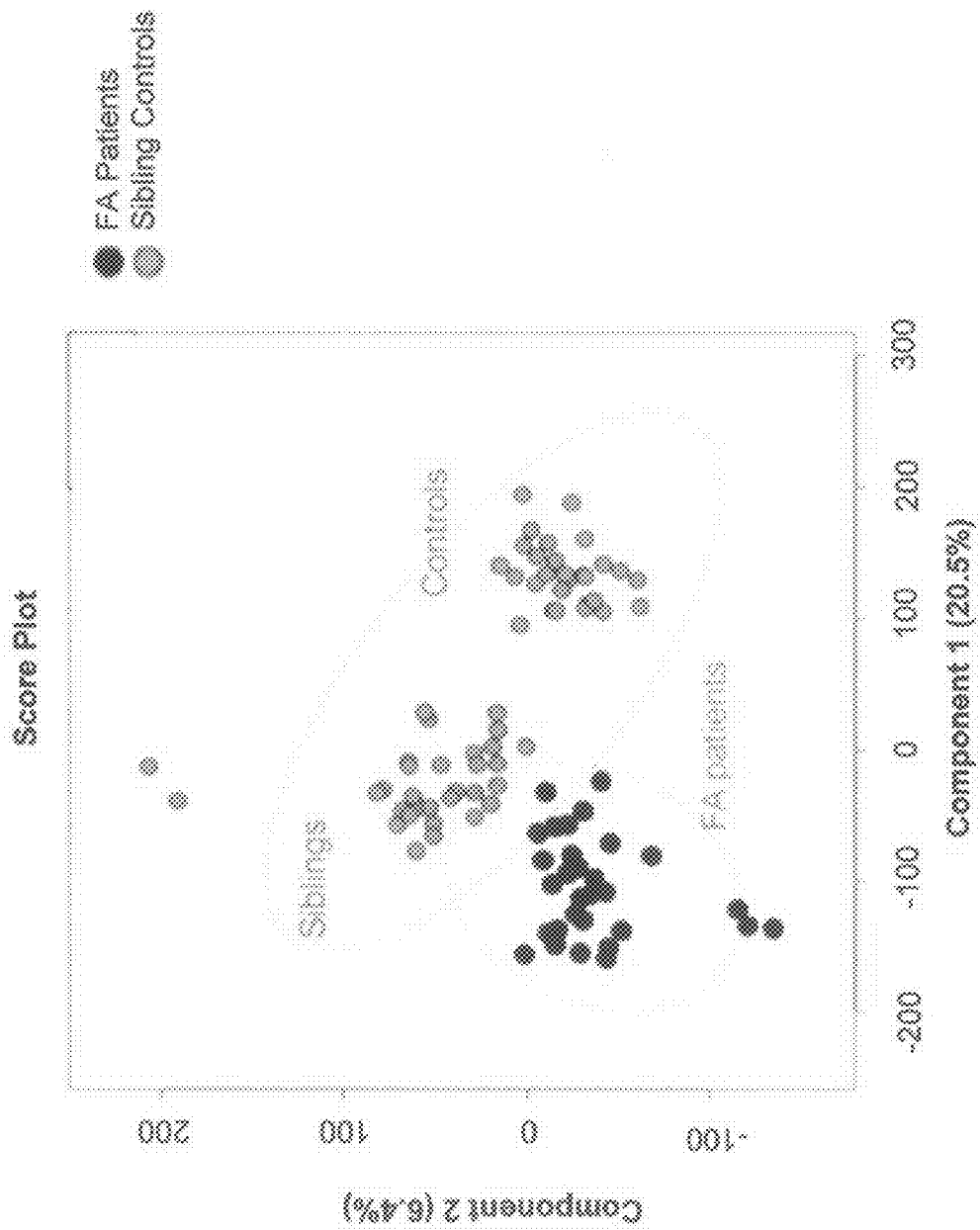
FIG. 16 shows two-dimensional PCA Score plot comparing urinary metabolic differences between individuals with FA (black), age/gender matched sibling controls (grey), and healthy controls (grey) using NMR spectroscopy. Clear separation of the groups is observed indicating that metabolic differences are present between the three groups. Circles indicate 95% confidence intervals for each group.
Figure 17:
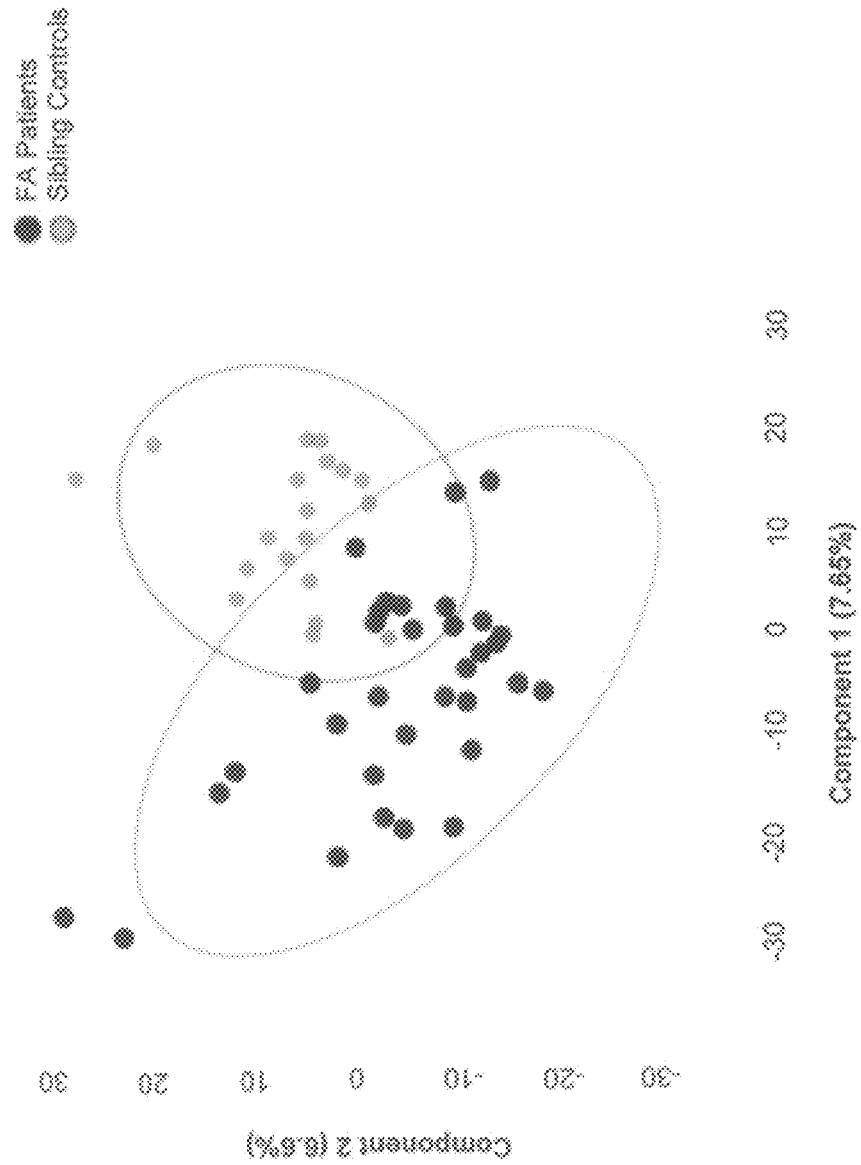
FIG. 17 shows two-dimensional PCA Score plot comparing the urinary metabolic profiles of only individuals with FA (black) and their matched siblings (grey). Clear separation is observed between the two groups. Circles indicate 95% confidence intervals.
Figure 18A:
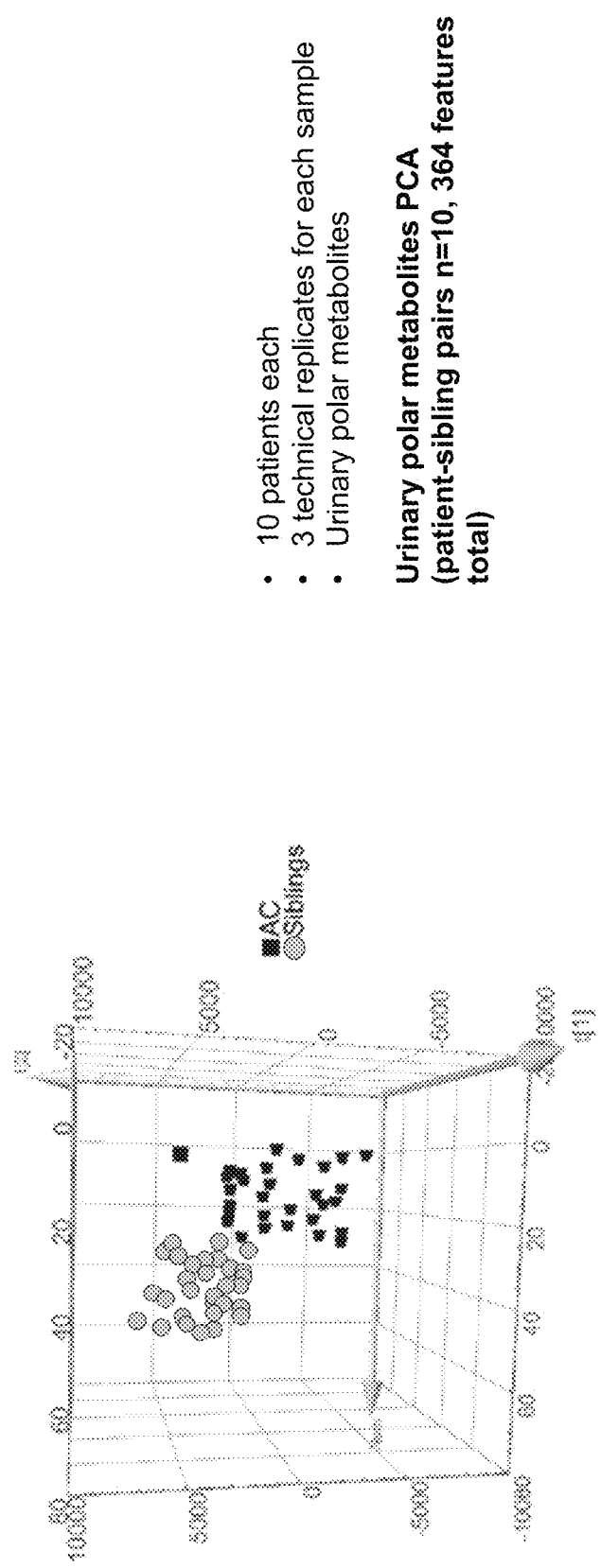
FIG. 18A shows 3-dimentional PCA Score plot comparing urinary metabolic differences between individuals with FA (black), age/gender matched sibling controls (grey), patient-sibling pairs n=10 (a) urinary polar metabolites PCA, with 364 features.
Figure 18B:
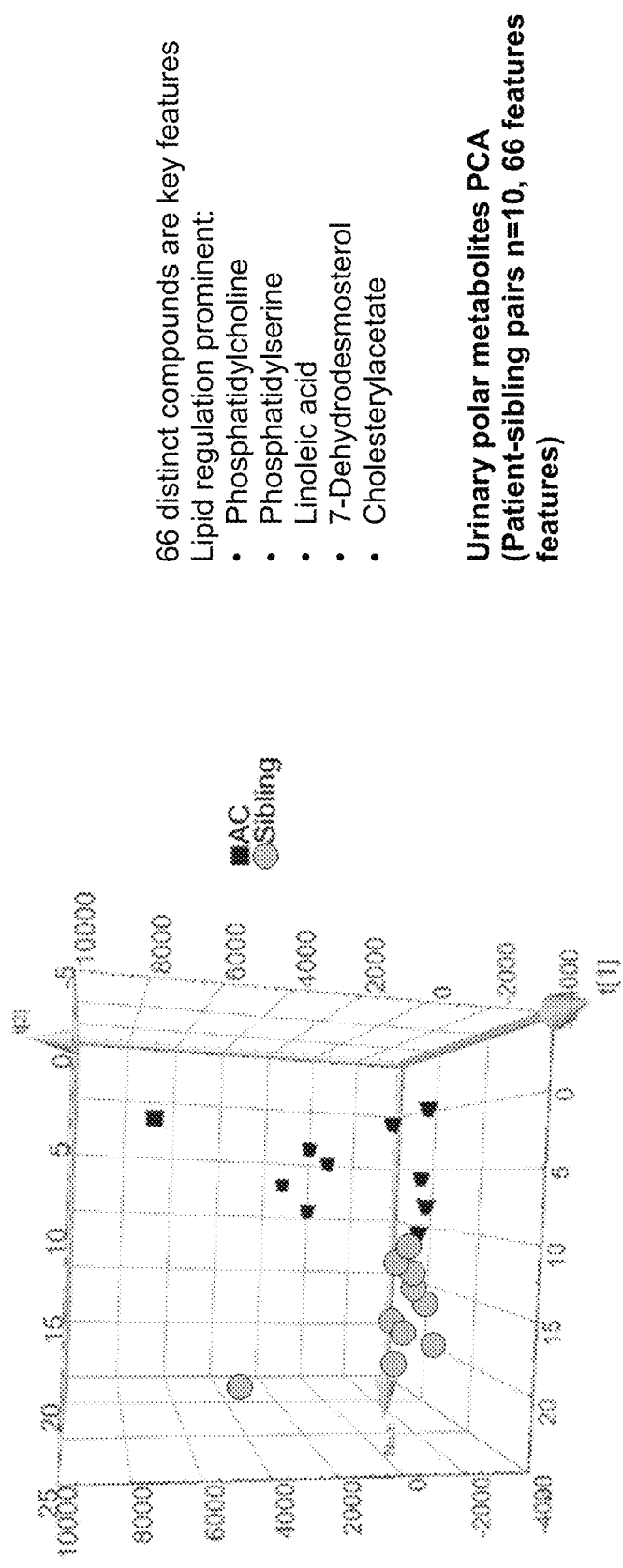
FIG. 18B shows urinary polar metabolites PCA with 66 features.
Figure 19:
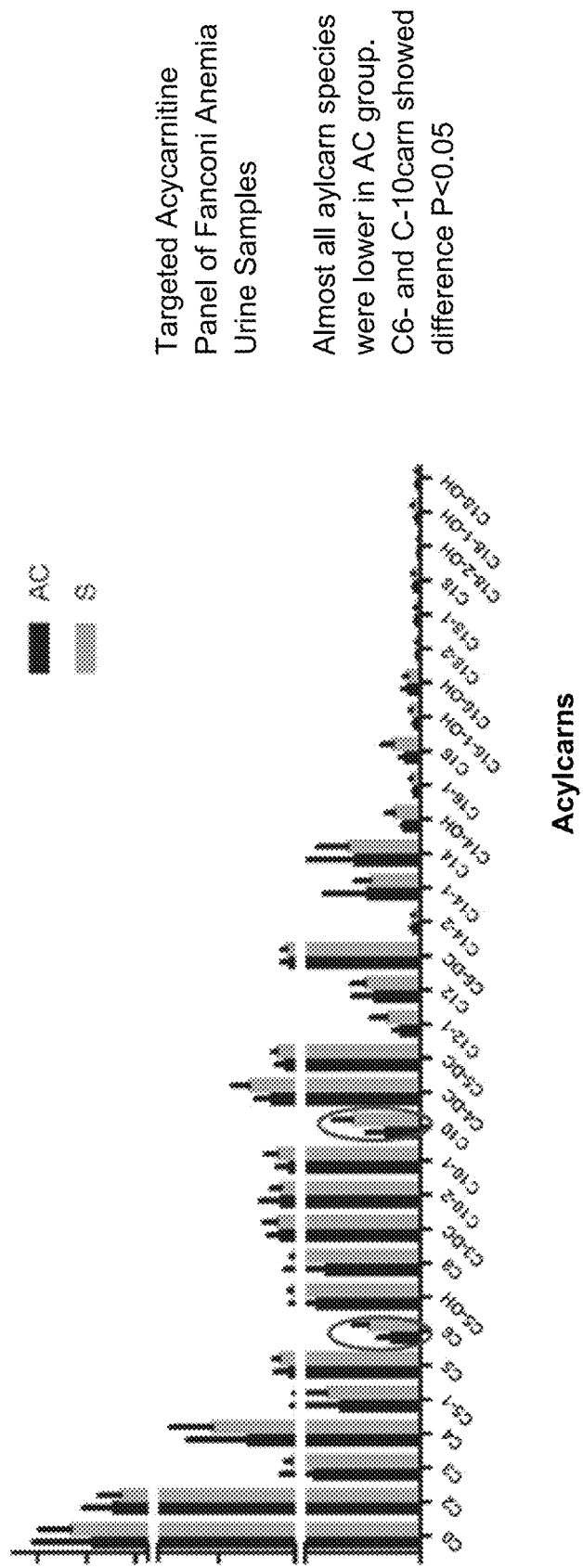
FIG. 19 shows targeted acylcarnitine panel of FA urine samples.

Rafts will be stained with H&E to assess overall morphology, BrdU for proliferation and cleaved caspase 3 for apoptosis. Portions of the rafts will be analyzed for GM3 levels by MS. Differentiation will be assessed (73) by IF of basal and differentiated cell markers: DeltaNp63 and keratin 14 (basal stem and progenitor cells); keratin 10, involucrin and loricrin (progressively differentiated cells). Hemidesmosome and desmosome components will be detected by IF, as described above. Overall morphology, including desmosome and hemidesmosome abnormalities, will be visualized by EM (as in FIGS. 1 and 7); pathologies will be evaluated and quantified. Abnormalities in raft integrity, differentiation and invasion into the underlying matrix will be quantified and related to GM3 levels.

Orthotopic xenografts will be generated by injecting tongues with FA-proficient and FA-deficient tumor cells. Mice will then be administered 200 ul of 5,000 mg/kg/d of NB-DNJ (or PBS) once a day by gavage. Mice will be sacrificed at the onset of morbidity, and GM3 repression confirmed in tongue and skin. Tumor incidence, growth and dissemination will be monitored by non-invasive in vivo bioluminescence imaging, as described. Tissues will be analyzed for proliferation, death, differentiation, adhesion and DNA-PK/Rac1 signaling, as previously described.

Correlation of FA skin pathologies, ganglioside levels, and barrier function by quantifying all three in skin specimens from FA patients. Skin punch biopsy specimens from FA patients and controls (Table 1) will be obtained. One half will be processed for EM and evaluated for skin integrity and pathology. The other half will be extracted for GM3 detection by MS. Since the availability of skin specimens is invasive and thus limited (~10 per year), these data will be used to make sample-size calculations for future studies, guided by logistical considerations. For noninvasive analyses of GM3 levels, skin surface keratinocytes will be collected using tape disks. Epidermal skin cells will be harvested during clinic or study visits using a published protocol. Three adherent circular D-Squame® tape disks (380 mm$^2$) will be placed sequentially on the same portion of intact skin for one minute, collected, and processed for targeted MS detection of gangliosides (as in FIG. 27). Skin pathology in patients will also be assessed by trans-epithelial water loss (TEWL) measurements on intact skin using a closed chamber VapoMete system (Delfin Technologies, Ltd, Finland). High rates of water loss indicate poor skin-barrier function (79). TEWL measurements will then be correlated with GM3 accumulation for each patient as compared to controls.

GM3 synthase protein levels are anticipated to be substantially reduced in St3Gal5sh compared to NTsh cells. If sufficient knockdown is not achieved, CRISPR/Cas technology will be employed for targeted St3Gal5 knockout (Addgene, Cambridge Mass.). NB-DNJ did not affect the growth of SCC1 or SCC47 cells, and St3Gal5 knockout mice are healthy and fertile (80). Therefore, it is expected GM3-inhibition will not be toxic. From data in FIGS. 27I and J, NB-DNJ are expected to diminish cellular motility and invasion triggered by FA loss. Repression of DNA-PK/Rac1 signaling and cellular reversal to a more epithelial phenotype may be observed. Conversely, GM3 upregulation may promote DNA-PK/Rac1 signaling and invasion, particularly in FA-proficient cells. Desmosome and hemidesmosome complexes may be regulated by GM3. However, while both DNA-PK/Rac1 signaling and GM3 accumulation promote invasion, they may do so through parallel pathways. Adhesion phenotypes may be uncoupled from motility. In this case, regulation and function of these individual FA-dependent phenotypes will be studied separately.

Based on GM3 inhibition data in FIG. 27I, J, FA-deficient rafts and tumors are expected to be more invasive compared to their FA-proficient counterparts, and GM3 inhibition is expected to reduce local and perhaps distal dissemination. GM3 inhibition might at least partially restore epidermal and/or tumor integrity. If GM3 inhibition is not achieve by NB-DNJ administration, drug activity will be enhanced by delivery of a liposome preparation (81). If tumor progression occurs despite efficient GM3 inhibition, NB-DNJ treatment will be combined with established procedures to administer the DNA-PK inhibitor NU7027 82, and/or Rac1 inhibitor (83) in HNSCC tumor bearing mice. Mice will be monitored by IVIS and analyzed as described above. Similar combination therapy will be carried out on organotypic rafts. Taken together, these results will explore the regulation and functional role of gangliosides in the FA-deficient cells models of human epidermis, toward development of lipid based prevention and treatment approaches for SCC.

In one embodiment, the invention provides a method of treating at least one condition of a gene instability disorder in an individual having a gene instability disorder characterized by increased NeuAC$\alpha$2-3Gal$\beta$1-4Glc$\beta$1-1ceramide (GM3) or their precursors (eg, lactosylceramide), or their metabolic products (eg, GD3, GM1). In one embodiment, the method administers a composition comprising a GM3 synthase inhibitor or inhibitors of the precursors (eg, glucosylceramide synthase inhibitor), or their metabolic products (eg, GM1) to treat at least one condition of the disorder.

In one embodiment, the invention provides a method of ameliorating at least one condition of a genetic instability disorder characterized by increased NeuAC$\alpha$2-3Gal$\beta$1-4Glc$\beta$1-1ceramide (GM3) or their precursors (eg, lactosylceramide), or their metabolic products (eg, GD3, GM1). In one embodiment, the method comprises administering a composition comprising a GM3 synthase inhibitor or inhibitors of the precursors (eg, glucosylceramide synthase inhibitor), or their metabolic products (eg, GM1) under conditions sufficient to decrease GM3 and ameliorate the condition.

In one embodiment, the GM3 synthase protein is inhibited using a pharmacological agent that inhibits the activity of the GM3 synthase protein. In one embodiment, the pharmacological agent is a GM3 synthase inhibitor, as is known in the art, such as NB-DNJ and Genz529468. In one embodiment, the activity of the GM3 synthase gene St3Gal5 is inhibited, e.g., knocked down or knocked out, to result in a decrease in the amount of GM3 synthase protein and a decrease in GM3 production. In one embodiment, the St3Gal5 gene is knocked down using RNAi using shRNA expressing lentiviruses. In one embodiment, the St3Gal5 gene is knocked out using CRISPR/Cas technology.

In one embodiment, the genetic instability disorder is selected from the group consisting of Fanconi Anemia (FA), ataxia telangiectasia (AT), AT-like disorder (ATLD), Nijmegen breakage syndrome (NBS), Werner's syndrome, Bloom's syndrome, Rothmund-Thompson syndrome, xeroderma pigmentosa (XP), and Cockayne's syndrome (CS). In one embodiment, the genetic instability disorder is FA.

In the methods described above, composition comprising the GM3 synthase inhibitor is administered orally, rectally, nasally, topically, parenterally, subcutaneously, intramuscularly, intravenously, transdermally, or a combination thereof.

In one embodiment, the condition treated and/or ameliorated is a skin abnormality and/or an abnormal cellular phenotype selected from diminished cellular adhesion, increased cellular migration, and/or increased cellular invasiveness of a cell. In one embodiment, administering the composition results in increased cellular adhesion, decreased cellular migration, and/or decreased cellular invasiveness compared to an individual not receiving the composition. While spontaneous blistering has never been reported in FA patients or mice, preliminary data demonstrate that skin of FA patients (vs controls) exhibits significantly reduced blistering time—that is, increased fragility. As shown in FIG. 36, a negative pressure cutaneous suction system (Electronic Diversities, Finksburg Md.) was applied to consented individuals in accordance with an approved IRB protocol. Time to blister formation was recorded as a measure of skin fragility, and FA patients (n=6) harbored significantly reduced blistering time compared to age- and gender-matched control subjects (n=9), p<0.0001). The method was performed as in Hatje et al., Blistering time as a parameter for the strength of dermoepidermal adhesion: a systematic review and meta-analysis, British Journal of Dermatology 2015, 172:323-30.

In one embodiment, the abnormal cellular phenotype is present in a cancerous or non-cancerous cell. In one embodiment, the cancerous cell is a squamous cell carcinoma (SCC) cell. In one embodiment, the SCC cell is a head and neck squamous cell carcinoma (HNSCC) cell. In one embodiment of the described method, administering the described composition results in a decrease in metastasis of the SCC cell compared to an individual not receiving the composition.

In one embodiment, the abnormal cellular phenotype is present in distinct types of skin cells such as keratinocytes, melanocytes, Merkel cells, and/or Langerhans cells. In one embodiment, the cell is a keratinocyte. In one embodiment of the described method, administering the described composition results in a decreased susceptibility to blistering and/or a decreased susceptibility to infectious agents passing through the skin compared to an individual not receiving the composition. In one embodiment, the described method treats and/or ameliorates a skin abnormality in the individual, where the skin abnormality is selected from an array of blistering disorders such as epidermolysis bullosa or barrier dysfunctions such as atopic dermatitis.

An untargeted metabolomics study of FA patient plasma yielded potential biomarkers to facilitate FA diagnosis and therapy monitoring.

FA is a recessive blood disorder characterized clinically by genomic instability, diverse congenital abnormalities, bone marrow failure and cancer predisposition. Treatment with androgens and hematopoietic (blood cell) growth factors can rescue bone marrow failure temporarily, but curative treatment requires a bone marrow transplant. Prevention is key, but prospective disease markers indicating the development of blood cancer originating from the genetic defect in DNA repair genes are yet to be identified. A clear and comprehensive understanding of FA a cancer prone disease, at a system-wide level and data extrapolation to the multitude of pediatric cancers is crucial for prognosis and development of effective therapies.

Mass spectrometry-based untargeted metabolomics/lipidomics was performed on a Xevo G2-S Q-TOF mass spectrometer interfaced with the ACQUITY UPLC system (Waters, Milford Mass. USA). FA patient plasma and control plasma were extracted with various solvent systems to obtain a complete metabolome and subjected to ultra-high performance liquid chromatography-mass spectrometry (UPLC-MS) platform. Univariate and multivariate analyses were used in selection of biomarkers from generated metabolomics data. Key metabolites were identified by database searching and confirmation with authentic standard. Quantitative assays for these biomarkers were developed to provide accurate concentrations of these metabolites to relate them to physiological and disease conditions. Putative biomarkers were assessed by receiver operator characteristic (ROC) curve analysis for their performance in early diagnosis of FA.

A MS-based global metabolomics study from FA plasma (10 µL) revealed the existence of several metabolite candidates that together comprise the FA signature. Principal component analysis, a multivariate statistical technique analyzing the interrelationship among thousands of metabolites to cluster data and to define group differences, clearly shows that several metabolites in the blood of FA patients (n=7) are uniquely different from those of age, gender-matched health controls (n=7). Tentative markers elevated in FA patient blood include potent, bioactive lipid species which were previously reported highly relevant in various cancers. Quantitative analysis of these lipid species were employed to validate results from untargeted comparative analysis. Based on area under ROC curve (AUC), a few sensitive and specific markers were presented in blood, which could be potentially used in clinical application.

As shown in FIG. 31, mass spectrometry based untargeted metabolomics/lipidomics study of FA patient plasma along with age, gender matched controls showed clear separation by multivariate analysis, principle component analysis, where paired principle component analysis (PCA) plot based on 436 compounds acquired through MS metabolomics platform. Altered lipid class in FA include phospholipids, sphingolipids and sterols. Particularly, lysophospholipid including lysophosphocholine (LPC), lysophosphoethanoamine (LPE), and lysophosphatidic acid (LPA) showed consistent significant accumulation in FA plasma compared to control group.

As shown in FIG. 32, an increased level of lysophosphatidylcholines in FA plasma, where data were based on quantitative analysis of each subspecies of lysophosphatidylcholines and T-test was done in pair wise fashion. Lysophospholipid include both ester bond and ether bond linked species. Chain length include 4:0/14:1/16:0/16:1/18:0/18:1/18:2/18:3/20:3/20:4/22:5/22:6. Accumulation of lysophospholipid is projected to have anti-apoptosis effect through LPA mediated LPA2 and G protein activation.

In one embodiment, the method provides for directed differentiation of FA inducible pluripotent stem cells (iPSCs) into keratinocyte lineages and 3D epidermis. This provides a model to study inherited diseases of the skin, including FA.

Solid tumors in Fanconi Anemia, squamous cell carcinomas of the head and neck, anogenital tract, and skin are most common in FA. The cells of origin for these cancers are mucosal or cutaneous keratinocytes, and the tissue of origin is the epidermis. Epidermis is the first defense against the external environment and is a barrier to mechanical, chemical, temperature, and infectious insults. Thirteen percent of FA individuals self-report skin SCC. A schematic of skin epidermis is shown in FIG. 37.

FA is a developmental disease. Universal cellular sensitivity to DNA crosslinkers is a hallmark of FA. Clinical consequences of FA are organ specific, eg. BM and epidermis. These originate in the FA context during embryonic development. Mouse models do not fully recapitulate the range of FA phenotypes; thus human models are necessary. As shown in FIG. 38, Left, are the 3 germ layers (ectoderm, mesoderm, endoderm) from which all organs derive. For FA, the same pathway and DNA repair defect occurs in all cells and organs. It is unclear why blood stem cell population exhaust, intestinal tissue is sustained and normal, and skin/mucosa is sustained but highly cancer prone.

Pluripotent stem cells can model organ-specific responses of FA. FA loss impairs iPSC reprogramming and the model provides an inducible FA pathway control. Generation of an FA-inducible iPSC model system is adapted from the description by Chlon et al, 2016 (Stem Cell Reports. 2016 Jan. 12; 6(1): 44-54), and is shown in FIGS. 39 and 40.

These iPSC lines were differentiated into skin +/− dox and thus +/− a functional FA pathway. Generation of iPSC-derived keratinocyte lineages and 3D epidermis. To model the developmental consequences of FA loss, we created iPSC lines from FANCA-deficient patients. Like embryonic stem cells, iPSCs have unlimited proliferative and differentiation potential; however, they differ in that they are generated from an individual's somatic cells. We and others have reported that somatic cells from FA patients are resistant to reprogramming. To circumvent this, we designed a conditional system (cFA-iPSC), in which the FANCA gene product is expressed in the presence of doxycyclin (DOX) throughout reprogramming and iPSC culture, until DOX is withdrawn. We rigorously validated conditional control of FANCA expression, and demonstrated that the FA pathway is essential for iPSC self-renewal. A few laboratories have recently differentiated iPSCs into keratinocyte lineages. To generate FA-proficient (DOX+) and FA-deficient (DOX−) epidermal stem and progenitor cells (ESPCs) from the cFA-iPSCs, we adopted elements from 2 published protocols (See FIG. 41A). Our resulting model of cutaneous epidermis is of ectodermal origin. Generation of endoderm-derived mucosa from pluripotent stem cells has not yet been achieved in the field.

In contrast to iPSCs, ESPCs did not require a functional FA pathway, and the resulting DOX+ and DOX− cultures were morphologically indistinguishable (FIG. 41A). As expected, both were still repressed for FANCA, and thus FANCD2 monoubiquitination and focus formation in the presence of γH2AX-marked DNA damage (FIGS. 41B and D, bottom panel). Monolayer cultures of DOX− or DOX+ ESPCs proliferated normally based on EdU and Ki67 staining (FIG. 41C and data not shown), and expressed 2 basal keratinocyte markers: ΔN-p63 mRNA (not shown) and K14 protein (FIG. 41D, top panel). DOX− or DOX+ ESPCs both formed stratified, differentiated epidermis in organotypic raft cultures (FIG. 41F).

Directed differentiation of human iPSCs into three dimensional epidermis is possible and provides a new model to study the earliest developmental causes of SCC. FA loss diminishes epidermal ultrastructure and integrity. This model provides a platform for testing preventive approaches that are lipid-based related to signaling. Diminished adhesion can present an inherent or exposure-specific risk. FA loss of function in epidermis impairs tissue structure and function, and stimulates stem cell exposure to exogenous stress (chemical, physical, infectious), as schemtatically shown in FIG. 42.

Each of the references described in the specification and the following references is expressly incorporated by reference herein in its entirety:

de Araujo et al: Fanconi's anemia: clinical and radiographic oral manifestations. Oral diseases 2007, 13:291-5.

De Kerviler et al: The clinical and radiological features of Fanconi's anaemia. Clinical radiology 2000, 55:340-5.

Karalis et al.: Millington GW: Dermatological manifestations of inherited cancer syndromes in children. The British journal of dermatology 2011, 164:245-56.

Tischkowitz et al.: Fanconi anaemia and leukaemia—clinical and molecular aspects. British journal of haematology 2004, 126:176-91.

Kennedy et al.: The Fanconi Anemia/BRCA pathway: new faces in the crowd. Genes & development 2005, 19:2925-40.

Kee et al.: Molecular pathogenesis and clinical management of Fanconi anemia. The Journal of clinical investigation 2012, 122:3799-806.

Kim et al.: Regulation of multiple DNA repair pathways by the Fanconi anemia protein SLX4. Blood 2013, 121:54-63.

Alter: Fanconi's anemia and malignancies. American journal of hematology 1996, 53:99-110.

Rosenberg et al: Cancer risks in Fanconi anemia: findings from the German Fanconi Anemia Registry. Haematologica 2008, 93:511-7.

Rosenberg et al.: Cancer incidence in persons with Fanconi anemia. Blood 2003, 101:822-6.

Kutler et al.: A 20-year perspective on the International Fanconi Anemia Registry (IFAR). Blood 2003, 101:1249-56.

Bosch et al.: The causal relation between human papillomavirus and cervical cancer. Journal of clinical pathology 2002, 55:244-65.

Fakhry, et al.: Clinical implications of human papillomavirus in head and neck cancers. Journal of clinical oncology: official journal of the American Society of Clinical Oncology 2006, 24:2606-11.

Park et al.: High incidence of HPV-associated head and neck cancers in FA deficient mice is associated with E7's induction of DNA damage through its inactivation of pocket proteins. PloS one 2013, 8:e75056.

Hoskins et al.: Fanconi anemia deficiency stimulates HPV-associated hyperplastic growth in organotypic epithelial raft culture. Oncogene 2009, 28:674-85.

Wu, et al.: Cancer stem cells are enriched in Fanconi anemia head and neck squamous cell carcinomas. International journal of oncology 2014, 45:2365-72.

Gammon et al.: Stem cell characteristics of cell sub-populations in cell lines derived from head and neck cancers of Fanconi anemia patients. Journal of oral pathology & medicine: official publication of the International Association of Oral Pathologists and the American Academy of Oral Pathology 2011, 40:143-52.

Alpi et al.: Mechanistic insight into site-restricted monoubiquitination of FANCD2 by Ube2t, FANCL, and FANCI. Molecular cell 2008, 32:767-77.

Machida et al.: UBE2T is the E2 in the Fanconi anemia pathway and undergoes negative autoregulation. Molecular cell 2006, 23:589-96.

Meetei et al.: A novel ubiquitin ligase is deficient in Fanconi anemia. Nature genetics 2003, 35:165-70.

Smogorzewska et al.: Identification of the FANCI protein, a monoubiquitinated FANCD2 paralog required for DNA repair. Cell 2007, 129:289-301.

Taniguchi et al.: S-phase-specific interaction of the Fanconi anemia protein, FANCD2, with BRCA1 and RAD51. Blood 2002, 100:2414-20.

Zhang et al.: Mechanism and regulation of incisions during DNA interstrand cross-link repair. DNA repair 2014, 19:135-42.

Alter et al.: Cancer in Fanconi anemia. Blood 2003, 101: 2072.

Kutler et al.: High incidence of head and neck squamous cell carcinoma in patients with Fanconi anemia. Archives of otolaryngology—head & neck surgery 2003, 129:106-12.

Alter: Cancer in Fanconi anemia, 1927-2001. Cancer 2003, 97:425-40.

Adamo et al.: Preventing nonhomologous end joining suppresses DNA repair defects of Fanconi anemia. Molecular cell 2010, 39:25-35.

Pace et al.: Ku70 corrupts DNA repair in the absence of the Fanconi anemia pathway. Science 2010, 329:219-23.

Parkin et al.: Fifty years of cancer incidence: CI5 I-IX. International journal of cancer Journal international du cancer 2010, 127:2918-27.

Gillison: Current topics in the epidemiology of oral cavity and oropharyngeal cancers. Head & neck 2007, 29:779-92.

Lacko et al.: Genetic susceptibility to head and neck squamous cell carcinoma. International journal of radiation oncology, biology, physics 2014, 89:38-48.

Corry et al.: Optimising the therapeutic ratio in head and neck cancer. Lancet Oncol, 11:287-91.

Romick-Rosendale et al.: The Fanconi anemia pathway: repairing the link between DNA damage and squamous cell carcinoma. Mutation research 2013, 743-744:78-88.

Stransky et al: The mutational landscape of head and neck squamous cell carcinoma. Science 2011, 333:1157-60.

Smith et al.: Inactivation of the tumor suppressor genes causing the hereditary syndromes predisposing to head and neck cancer via promoter hypermethylation in sporadic head and neck cancers. ORL; journal for oto-rhino-laryngology and its related specialties 2010, 72:44-50.

Wreesmann et al.: Downregulation of Fanconi anemia genes in sporadic head and neck squamous cell carcinoma. ORL; journal for oto-rhino-laryngology and its related specialties 2007, 69:218-25.

Rossman et al.: GEF means go: turning on RHO GTPases with guanine nucleotide-exchange factors. Nature reviews Molecular cell biology 2005, 6:167-80.

del Pozo et al.: Integrins regulate Rac targeting by internalization of membrane domains. Science 2004, 303:839-42.

Michaely et al.: Polarized distribution of endogenous Rac1 and RhoA at the cell surface. The Journal of biological chemistry 1999, 274:21430-6.

Moissoglu et al.: Regulation of Rac1 translocation and activation by membrane domains and their boundaries. Journal of cell science 2014, 127:2565-76.

Hoskins et al.: Coordinate regulation of Fanconi anemia gene expression occurs through the Rb/E2F pathway. Oncogene 2008, 27:4798-808.

Chandra et al.: A rapid method for retrovirus-mediated identification of complementation groups in Fanconi anemia patients. Molecular therapy: the journal of the American Society of Gene Therapy 2005, 12:976-84.

Hanenberg et al.: Phenotypic correction of primary Fanconi anemia T cells with retroviral vectors as a diagnostic tool. Exp Hematol 2002, 30:410-20.

Nakahara et al.: Human papillomavirus type 16 E1circumflexE4 contributes to multiple facets of the papillomavirus life cycle. Journal of virology 2005, 79:13150-65.

Chen et al.: Cell cycle dependence of DNA-dependent protein kinase phosphorylation in response to DNA double strand breaks. The Journal of biological chemistry 2005, 280:14709-15.

Etienne-Manneville et al.: Rho GTPases in cell biology. Nature 2002, 420:629-35.

Evers et al.: Rho family proteins in cell adhesion and cell migration. European journal of cancer 2000, 36:1269-74.

Caron et al.: Identification of two distinct mechanisms of phagocytosis controlled by different Rho GTPases. Science 1998, 282:1717-21.

Nassar et al.: Structure-function based design of small molecule inhibitors targeting Rho family GTPases. Current topics in medicinal chemistry 2006, 6:1109-16.

Gao et al.: Rational design and characterization of a Rac GTPase-specific small molecule inhibitor. Proceedings of the National Academy of Sciences of the United States of America 2004, 101:7618-23.

Lombardi, et al.: Acquisition of Relative Interstrand Crosslinker Resistance and PARP Inhibitor Sensitivity in Fanconi Anemia Head and Neck Cancers. Clinical cancer research: an official journal of the American Association for Cancer Research 2015.

Schurr et al.: Clinical Evaluation of NIKS-Based Bioengineered Skin Substitute Tissue in Complex Skin Defects: Phase I/IIa Clinical Trial Results. Advances in wound care 2012, 1:95-103.

Piboonniyom et al.: Abrogation of the retinoblastoma tumor suppressor checkpoint during keratinocyte immortalization is not sufficient for induction of centrosome-mediated genomic instability. Cancer research 2003, 63:476-83.

Chan et al.: Autophosphorylation of the DNA-dependent protein kinase catalytic subunit is required for rejoining of DNA double-strand breaks. Genes & development 2002, 16:2333-8.

Douglas et al.: The DNA-dependent protein kinase catalytic subunit is phosphorylated in vivo on threonine 3950, a highly conserved amino acid in the protein kinase domain. Molecular and cellular biology 2007, 27:1581-91.

Wong et al.: A role of DNA-PK for the metabolic gene regulation in response to insulin. Cell 2009, 136:1056-72.

Guo et al.: Rac1 controls Schwann cell myelination through cAMP and NF2/merlin. The Journal of neuroscience: the official journal of the Society for Neuroscience 2012, 32:17251-61.

Giangreco et al.: Necl2 regulates epidermal adhesion and wound repair. Development 2009, 136:3505-14.

Morrison et al.: Targeting the human papillomavirus E6 and E7 oncogenes through expression of the bovine papillomavirus type 1 E2 protein stimulates cellular motility. Journal of virology 2011, 85:10487-98.

Privette et al.: The human DEK oncogene stimulates beta-catenin signaling, invasion and mammosphere formation in breast cancer. Oncogene 2011, 30:2741-52.

Hattersley et al.: Lipid composition of membrane rafts, isolated with and without detergent, from the spleen of a mouse model of Gaucher disease. Biochemical and biophysical research communications 2013, 442:62-7.

Meetei et al.: A multiprotein nuclear complex connects Fanconi anemia and Bloom syndrome. Mol Cell Biol 2003, 23:3417-26.

Singh et al.: BLAP18/RMI2, a novel OB-fold-containing protein, is an essential component of the Bloom helicase-double Holliday junction dissolvasome. Genes Dev 2008, 22:2856-68.

Tu et al.: DNA-dependent protein kinase catalytic subunit (DNA-PKcs)-SIN1 association mediates ultraviolet B (UVB)-induced Akt Ser-473 phosphorylation and skin cell survival. Molecular cancer 2013, 12:172.

Zhu et al.: An EGFR/PI3K/AKT axis promotes accumulation of the Rac1-GEF Tiam1 that is critical in EGFR-driven tumorigenesis. Oncogene 2015.

Goodpaster et al.: Statistical significance analysis of nuclear magnetic resonance-based metabonomics data. Analytical biochemistry 2010, 401:134-43.

Romick-Rosendale et al.: Identification of urinary metabolites that distinguish membranous lupus nephritis from proliferative lupus nephritis and focal segmental glomerulosclerosis. Arthritis research & therapy 2011, 13:R199.

Romick-Rosendale et al.: NMR-based metabonomics analysis of mouse urine and fecal extracts following oral treatment with the broad-spectrum antibiotic enrofloxacin (Baytril). Magnetic resonance in chemistry: MRC 2009, 47 Suppl 1:S36-46.

Romick-Rosendale et al.: The Fanconi anemia pathway: Repairing the link between DNA damage and squamous cell carcinoma. Mutat Res 2013.

Janich et al.: GM1 and GM3 gangliosides highlight distinct lipid microdomains within the apical domain of epithelial cells. FEBS letters 2007, 581:1783-7.

Wang et al.: Ganglioside GM3 depletion reverses impaired wound healing in diabetic mice by activating IGF-1 and insulin receptors. The Journal of investigative dermatology 2014, 134:1446-55.

Bolot et al.: Analysis of glycosphingolipids of human head and neck carcinomas with comparison to normal tissue. Biochemistry and molecular biology international 1998, 46:125-35.

Portoukalian et al.: Tumor size-dependent elevations of serum gangliosides in patients with head and neck carcinomas. Biochemistry international 1989, 18:759-65.

Platt et al.: Extensive glycosphingolipid depletion in the liver and lymphoid organs of mice treated with N-butyldeoxynojirimycin. The Journal of biological chemistry 1997, 272:19365-72.

Hoskins et al.: The fanconi anemia pathway limits human papillomavirus replication. Journal of virology 2012, 86:8131-8.

Nietupski et al.: Iminosugar-based inhibitors of glucosylceramide synthase prolong survival but paradoxically increase brain glucosylceramide levels in Niemann-Pick C mice. Molecular genetics and metabolism 2012, 105:621-8.

Huang et al.: Human GM3 Synthase Attenuates Taxol-Triggered Apoptosis Associated with Down regulation of Caspase-3 in Ovarian Cancer Cells. Journal of cancer therapy 2012, 3:504-10.

Resnik et al.: Desmosome assembly and cell-cell adhesion are membrane raft-dependent processes. The Journal of biological chemistry 2011, 286:1499-507.

Broussard et al.: Desmosome regulation and signaling in disease. Cell and tissue research 2015.

Osmani et al.: Remodeling of keratin-coupled cell adhesion complexes. Current opinion in cell biology 2015, 32:30-8.

Nikolovski et al.: Barrier function and water-holding and transport properties of infant stratum corneum are different from adult and continue to develop through the first year of life. The Journal of investigative dermatology 2008, 128:1728-36.

Yamashita et al.: Enhanced insulin sensitivity in mice lacking ganglioside GM3. Proceedings of the National Academy of Sciences of the United States of America 2003, 100:3445-9.

Miller et al.: Liposome-mediated delivery of iminosugars enhances efficacy against dengue virus in vivo. Antimicrobial agents and chemotherapy 2012, 56:6379-86.

Li et al.: Protein phosphatase 2A and DNA-dependent protein kinase are involved in mediating rapamycin-induced Akt phosphorylation. The Journal of biological chemistry 2013, 288:13215-24.

Milsom et al.: Fanca−/− hematopoietic stem cells demonstrate a mobilization defect which can be overcome by administration of the Rac inhibitor NSC23766. Haematologica 2009, 94:1011-5.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims.

What is claimed is:

1. A method of treating at least one condition of a gene instability disorder in an individual having a gene instability disorder characterized by increased NeuAC$\alpha$2-3Gal$\beta$1-4Glc$\beta$1-1ceramide (GM3), increased GM3 precursor, or increased GM3 metabolic product, the method comprising the step of administering a composition comprising an iminosugar-based GM3 synthase inhibitor selected from the group consisting of NB-DNJ and Genz529468 to treat the at least one condition, where the at least one condition is a skin abnormality or an abnormal cellular phenotype selected from the group consisting of diminished cellular adhesion, increased cellular migration, increased cellular invasiveness, and combinations thereof, where the gene instability disorder is selected from the group consisting of Fanconi Anemia (FA), ataxia telangiectasia (AT), AT-like disorder (ATLD), Nijmegen breakage syndrome (NBS), Werner's syndrome, Bloom's syndrome, Rothmund-Thompson syndrome, xeroderma pigmentosa (XP), Cockayne's syndrome (CS), and combinations thereof.

2. The method of claim 1 where the genetic instability disorder is Fanconi Anemia (FA).

3. The method of claim 1 where the composition is administered by a route selected from the group consisting of orally, rectally, nasally, topically, parenterally, subcutaneously, intramuscularly, intravenously, transdermally, or a combination thereof.

4. The method of claim 1 where administering the composition results in increased cellular adhesion, decreased cellular migration, decreased cellular invasiveness, and/or decreased blistering compared to an individual not receiving the composition.

5. The method of claim 1 where the cell exhibiting the abnormal cellular phenotype is cancerous or non-cancerous.

6. The method of claim 5 where the cancerous cell is a squamous cell carcinoma (SCC) cell.

7. The method of claim 6 where the SCC cell is a head and neck squamous cell carcinoma (HNSCC) cell.

8. The method of claim 6 where administering the composition results in a decrease in metastasis of the SCC cell compared to an individual not receiving the composition.

9. The method of claim 1 where the cell exhibiting the abnormal cellular phenotype is a skin cell selected from the group consisting of keratinocytes, melanocytes, Merkel cells, Langerhans cells, and combinations thereof.

10. The method of claim 1 wherein the cell exhibiting the abnormal cellular phenotype is a keratinocyte.

11. The method of claim 9 where administering the composition results in a decreased susceptibility to blistering and/or a decreased susceptibility to infectious agents passing through the skin compared to an individual not receiving the composition.

12. A method of ameliorating at least one condition of a genetic instability disorder characterized by increased NeuAC$\alpha$2-3Gal$\beta$1-4Glc$\beta$1-1ceramide (GM3), the method comprising administering a composition comprising a GM3 synthase inhibitor selected from the group consisting of NB-DNJ and Genz529468 under conditions sufficient to decrease GM3 and ameliorate the condition, where the at least one condition is a skin abnormality or an abnormal cellular phenotype selected from the group consisting of diminished cellular adhesion, increased cellular migration, increased cellular invasiveness, and combinations thereof, where the gene instability disorder is selected from the group consisting of Fanconi Anemia (FA), ataxia telangiectasia (AT), AT-like disorder (ATLD), Nijmegen breakage syndrome (NBS), Werner's syndrome, Bloom's syndrome, Rothmund-Thompson syndrome, xeroderma pigmentosa (XP), Cockayne's syndrome (CS), and combinations thereof.

* * * * *